(12) United States Patent
Chavez et al.

(10) Patent No.: US 8,563,603 B2
(45) Date of Patent: Oct. 22, 2013

(54) POLYCYCLIC COMPOUNDS AND METHODS RELATED THERETO

(75) Inventors: Kathryn J. Chavez, Pueblo, CO (US); Eloy Rodriguez, Ithaca, NY (US); Frank Schroeder, Ithaca, NY (US); James A. Flanders, Ithaca, NY (US)

(73) Assignee: Cornell University, Ithaca, NY (US)

( * ) Notice: Subject to any disclaimer, the term of this patent is extended or adjusted under 35 U.S.C. 154(b) by 168 days.

(21) Appl. No.: 13/125,581

(22) PCT Filed: Oct. 22, 2009

(86) PCT No.: PCT/US2009/061739
§ 371 (c)(1),
(2), (4) Date: Apr. 22, 2011

(87) PCT Pub. No.: WO2010/048452
PCT Pub. Date: Apr. 29, 2010

(65) Prior Publication Data
US 2011/0275708 A1    Nov. 10, 2011

Related U.S. Application Data

(60) Provisional application No. 61/107,603, filed on Oct. 22, 2008.

(51) Int. Cl.
*A01N 43/12* (2006.01)
*A61K 31/34* (2006.01)
*C07D 311/96* (2006.01)
*C07D 307/94* (2006.01)

(52) U.S. Cl.
USPC .......................... 514/462; 549/331; 549/345

(58) Field of Classification Search
None
See application file for complete search history.

(56) References Cited

U.S. PATENT DOCUMENTS

2005/0119231 A1    6/2005    Ellsworth et al.

OTHER PUBLICATIONS

Trahanovsky, W. S., et al., "Preparation of Furanoradialene by the Flash Vaccum Pyrolysis of Diesters of 3,4-Bis (hydroxymethyl)-2,5-dimethylfuran", J. Am. Chem. Soc., 106:8197-8201 (1984).
English language translation of Notification of First Office Action dated Aug. 14, 2012 and English language translation of Search Report for Chinese Application No. 2009801521893.

*Primary Examiner* — Bong-Sook Baek
(74) *Attorney, Agent, or Firm* — Scully, Scott, Murphy & Presser, P.C.

(57) ABSTRACT

The invention relates to a novel compound of formula I or pharmaceutically acceptable salts thereof as well as pharmaceutical, nutraceutical, and botanical drug compositions and therapeutic methods related thereto. In certain embodiments, the compounds are used for the treatment of abnormal cell growth, hyperproliferative disorders, and inflammatory diseases in mammals. In other embodiments, the invention encompasses methods to isolate and synthesize the compounds.

16 Claims, 27 Drawing Sheets

| (ppm) | SKBR-3 | BT-20 | MD-MDA-468 | MD-MDA-453 | MD-MDA-231 |
|---|---|---|---|---|---|
| 1000 | +++ | +++ | +++ | +++ | +++ |
| 500 | +++ | +++ | +++ | +++ | +++ |
| 250 | +++ | +++ | +++ | +++ | +++ |
| 125 | +++ | +++ | +++ | +++ | +++ |
| 62.5 | ++ | ++ | +++ | ++ | +++ |
| 61.3 | ++ | ++ | + | ++ | ++ |
| 15.6 | - | ++ | - | ++ | - |
| 7.8 | - | - | - | - | - |

FIGURE 19

| (ppm) | CaLu-6 | | HCT-116 | | HT-29 | | Hela | | MCF-7 | |
|---|---|---|---|---|---|---|---|---|---|---|
| | wood | bark | wood | bark | wood | bark | wood | bark | wood | bark |
| 1000 | +++ | +++ | +++ | +++ | +++ | +++ | +++ | +++ | +++ | +++ |
| 500 | +++ | +++ | +++ | +++ | + | +++ | +++ | +++ | +++ | +++ |
| 250 | +++ | +++ | ++ | +++ | - | ++ | ++ | +++ | ++ | +++ |
| 125 | + | + | + | - | - | + | - | ++ | ++ | +++ |
| 62.5 | - | - | - | - | - | - | - | - | + | +++ |
| 31.3 | - | - | - | - | - | - | - | - | - | - |
| 15.6 | - | - | - | - | - | - | - | - | - | - |
| 7.8 | - | - | - | - | - | - | - | - | - | - |

FIGURE 23

A. Fractions from the heartwood of *Guaiacum sanctum* L.

| ppm | 1 | 2 | 3 | 4 | 5 | 6 | 7 | Cpt | 5-FU | DMSO |
|---|---|---|---|---|---|---|---|---|---|---|
| 1000 | ++++ | ++++ | ++++ | ++++ | ++++ | ++++ | ++++ | ++++ | +++ | ++++ |
| 500 | ++++ | +++ | +++ | +++ | +++ | ++++ | ++++ | ++++/++++ | +++ | +++ |
| 250 | ++ | ++ | ++ | +++/++ | ++ | ++++ | ++++ | ++ | +++ | + |
| 125 | - | + | + | ++ | ++ | ++ | +++ | + | +++ | - |
| 62.5 | - | - | - | + | ++ | - | ++ | + | +++ | - |
| 31.25 | - | - | - | + | + | - | + | - | +++ | - |
| 15.625 | - | - | - | - | - | - | - | - | ++ | - |
| 7.8125 | - | - | - | - | - | - | - | - | ++ | - |

B. Fractions from the heartwood of *Guaiacum officinale* L.

| ppm | 1 | 2 | 3 | 4 | 5 | 6 | 7 | Cpt | 5-FU | DMSO |
|---|---|---|---|---|---|---|---|---|---|---|
| 1000 | +++++ | +++++ | +++++ | +++ | +++++ | +++++ | +++++ | +++++ | +++ | ++++ |
| 500 | +++++ | +++ | +++ | ++ | +++++ | +++++ | ++++ | ++++ | +++ | +++ |
| 250 | - | ++ | ++ | + | ++++ | ++++ | ++ | ++ | +++ | + |
| 125 | - | - | - | - | ++ | ++++ | + | + | +++ | - |
| 62.5 | - | - | - | - | + | +++ | - | - | +++ | - |
| 31.25 | - | - | - | - | - | + | - | - | ++ | - |
| 15.625 | - | - | - | - | - | - | - | - | - | - |
| 7.8125 | - | - | - | - | - | - | - | - | - | - |

FIGURE 27

POLYCYCLIC COMPOUNDS AND METHODS RELATED THERETO

RELATED APPLICATIONS

This application is claiming benefit of U.S. Ser. No. 61/107,603 filed on Oct. 22, 2008, the contents of which are incorporated herein by reference.

GOVERNMENT SUPPORT

This invention was made with Government support under Grant Nos. MIRT/NIHT37TW0007, awarded by the National Institutes of Health. The government has certain rights in the invention.

BACKGROUND

Plant-derived secondary metabolites such as taxol or camptothecin are among the most effective chemotherapeutic agents used in cancer treatment. Interestingly, long-lived tree species from various parts of the world have yielded many of the most interesting drug leads. For example, yew trees (*Taxus* spp.) are the source of the taxanes, a group of structurally unique diterpenes, whereas camptothecin, a quinoline alkaloid, was identified from the bark of the Southeast Asian "Happy tree", *Camptotheca acuminata*.

From a phytochemical point of view, the resin of *Guaiacum officinale* L. and to a lesser extent *Guaiacum sanctum* L. has been the subject of many investigations since the early nineteenth century. The resin is purported to contain a number of grouped constituents; resin acids, which are reported to constitute 18-25% of the wood, a number of miscellaneous constituents found in smaller quantities; oils such as guaiol and bulesol, vanillin, terpenes, and quiaicsaponins, and a variety of lignans.

The resin and heartwood of *Guaiacum* is of particular interest because of its strong association with lignan compounds. Lignans have considerable biological diversity and several have been previously isolated from the heartwood of *Guaiacum sanctum* L. and *Guaiacum officinale* L. Guaiaretic acid, dihydroguaiaretic acid, nordihydroguaiaretic acid, guaiacic and α and β guaiaconic acids, have shown some antioxidant activity, with the latter having been reported as a treatment for liver disorders. Furoguaiacidin specifically, has been reported as a 5-lipoxygenase inhibitor and aldose reductase inhibitor and has been successful in the treatment of inflammation, thrombosis, allergies, asthma.

Excluding skin cancer, breast cancer is the most common malignancy among women; accounting for nearly 1 in 3 cancers diagnosed in women (American Cancer Society, 2006). In 2007, an estimated 178,480 new cases of invasive breast cancer were expected to be diagnosed among women and approximately 40,460 women were expected to die from it (American Cancer Society, 2007). The overall breast cancer mortality rate has been declining as a result of awareness, early detection through screening and improved treatment regimens available in the early clinical stages of the disease (NIH, 2003). However, treatment for advanced breast cancer remains at best palliative, with prolongation of survival rather than curative. Survival rates in patients with advanced breast cancer vary with the heterogeneity of the disease, but virtually all will relapse (National Cancer Institute, 2003 and American Cancer Society, 2007). It is evident that cytotoxic therapies for the treatment of advanced breast cancer still remain unsatisfactory. Therefore, the need for new drug development and more effective therapies for advanced breast cancer remain.

FIELD OF THE INVENTION

The invention pertains to the field of heterocyclic compounds. More particularly, the invention pertains to novel lignan compounds and methods for their isolation, synthesis, and therapeutic use.

SUMMARY

In one embodiment, the present disclosure encompasses novel compounds having formula I, or pharmaceutically acceptable salts thereof,

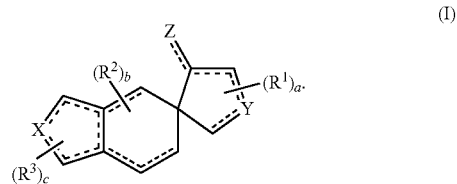

(I)

In certain embodiments, the present disclosure encompasses compositions of matter comprising compound I-a, compound I-b or mixtures of compounds I-a and I-b.

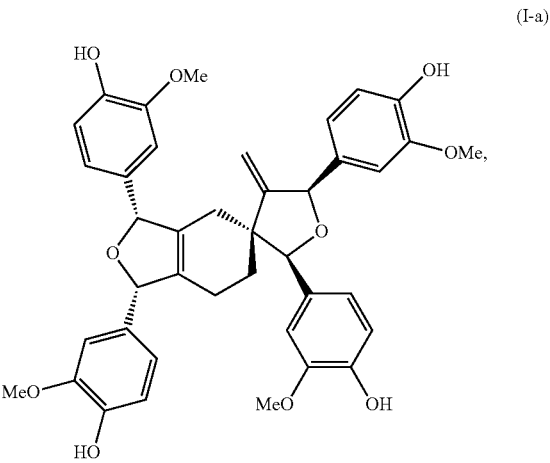

(I-a)

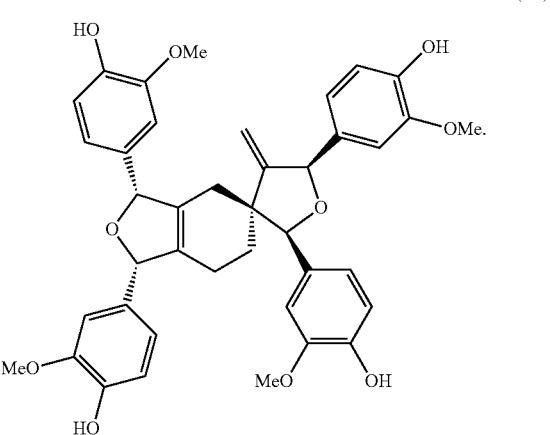

(I-b)

In certain embodiments, the present disclosure encompasses synthetic, or semi-synthetic derivatives derived from compounds I-a or I-b, or from mixtures of the two. In other embodiments, the present disclosure encompasses methods of producing such derivatives from compounds I-a or I-b.

In another embodiment, the present disclosure encompasses methods for the treatment of abnormal cell growth in a mammal comprising administering a therapeutically effective amount of one or more compounds of formulae I, I-a, or I-b, or a pharmaceutically effective salt thereof to a mammal in need of such treatment.

In another embodiment, the present disclosure encompasses methods for the treatment of a proliferative disorder in a mammal comprising administering a therapeutically effective amount of one or more compounds of formulae I, I-a, or I-b, or a pharmaceutically effective salt thereof to a mammal in need of such treatment.

In another embodiment, the present disclosure encompasses pharmaceutical formulations containing one or more compounds of formulae I, I-a, or I-b. In certain embodiments, these formulations include one or more additional therapeutic agents.

In another embodiment, the present disclosure encompasses nutraceutical compositions containing one or more compounds of formulae I, I-a, or I-b. In certain embodiments, these formulations include one or more additional constituents.

In other embodiments, the present disclosure encompasses botanical extracts containing one or more compounds of formula I. In certain embodiments, the botanical extracts are derived from plants belonging to the genus *Guaiacum*. In certain embodiments, the plant materials are processed to increase the concentration of compounds having formulae I, I-a, or I-b.

In another embodiment, the present disclosure encompasses methods of treating plant matter to yield products enriched in compounds having formulae I, I-a, or I-b.

In other embodiments, the present disclosure encompasses methods for synthesizing compounds of formula I. In certain embodiments, the methods of synthesis include the step of performing a Diels Alder cycloaddition reaction between two components as shown in Scheme I.

Scheme I

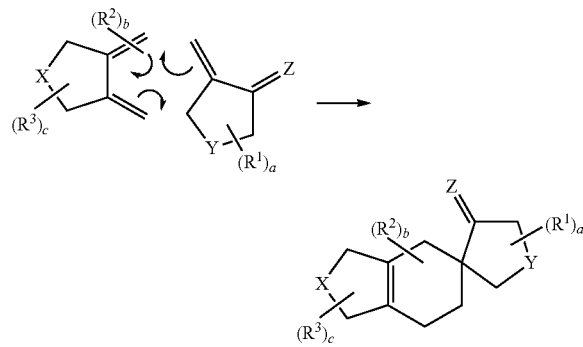

DEFINITIONS

Definitions of specific functional groups and chemical terms are described in more detail below. For purposes of this invention, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

Certain compounds of the present invention can comprise one or more asymmetric centers, and thus can exist in various stereoisomeric forms, e.g., enantiomers and/or diastereomers. Thus, inventive compounds and compositions thereof may be in the form of an individual enantiomer, diastereomer or geometric isomer, or may be in the form of a mixture of stereoisomers. In certain embodiments, the compounds of the invention are enantiopure compounds. In certain other embodiments, mixtures of enantiomers or diastereomers are provided.

Furthermore, certain compounds, as described herein may have one or more double bonds that can exist as either a Z or E isomer, unless otherwise indicated. The invention additionally encompasses the compounds as individual isomers substantially free of other isomers and alternatively, as mixtures of various isomers, e.g., racemic mixtures of enantiomers. In addition to the above-mentioned compounds per se, this invention also encompasses compositions comprising one or more compounds.

As used herein, the term "isomers" includes any and all geometric isomers and stereoisomers. For example, "isomers" include cis- and trans-isomers, E- and Z-isomers, R- and S-enantiomers, diastereomers, (D)-isomers, (L)-isomers, racemic mixtures thereof, and other mixtures thereof, as falling within the scope of the invention. For instance, a compound may, in some embodiments, be provided substantially free of one or more corresponding stereoisomers, and may also be referred to as "stereochemically enriched."

Where a particular enantiomer is preferred, it may, in some embodiments be provided substantially free of the opposite enantiomer, and may also be referred to as "optically enriched." "Optically enriched," as used herein, means that the compound is made up of a significantly greater proportion of one enantiomer. In certain embodiments the compound is made up of at least about 90% by weight of an enantiomer. In some embodiments the compound is made up of at least about 95%, 97%, 98%, 99%, 99.5%, 99.7%, 99.8%, or 99.9% by weight of an enantiomer. In some embodiments the enantiomeric excess of provided compounds is at least about 90%, 95%, 97%, 98%, 99%, 99.5%, 99.7%, 99.8%, or 99.9%. In some embodiments, enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

The terms "halo" and "halogen" as used herein refer to an atom selected from fluorine (fluoro, —F), chlorine (chloro, —Cl), bromine (bromo, —Br), and iodine (iodo, —I).

The term "aliphatic" or "aliphatic group", as used herein, when used alone or in combination, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-30 carbon atoms. In certain embodiments, aliphatic groups contain 1-12 carbon atoms. In certain embodiments, aliphatic groups contain 1-8 carbon atoms. In certain embodiments, aliphatic groups contain 1-6 carbon atoms. In some embodiments, aliphatic groups contain 1-5 carbon atoms, in some embodiments, aliphatic groups contain 1-4 carbon atoms, in yet other embodiments aliphatic groups contain 1-3 carbon atoms, and in yet other embodiments aliphatic groups contain 1-2 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "heteroaliphatic" refers to an aliphatic group as defined herein wherein 1-4 carbon atoms are replaced with 1-4 heteroatoms, respectively, selected from nitrogen, oxygen and sulfur.

The term "unsaturated", as used herein, means that a moiety has one or more double or triple bonds, but is not aromatic.

The terms "cycloaliphatic", "carbocycle", or "carbocyclic", used alone or as part of a larger moiety, refer to a saturated or partially unsaturated cyclic aliphatic monocyclic, bicyclic, or polycyclic ring systems, as described herein, having from 3 to 12 members, wherein the ring atoms are all carbon atoms and wherein the aliphatic ring system is optionally substituted as defined above and described herein. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloalkyl has 3-6 carbons. The terms "cycloaliphatic", "carbocycle" or "carbocyclic" also include aliphatic rings that are fused to one or more aromatic or nonaromatic rings, such as decahydronaphthyl or tetrahydronaphthyl, where the radical or point of attachment is on the aliphatic ring. In some embodiments, a carbocyclic groups is bicyclic. In some embodiments, a carbocyclic group is tricyclic. In some embodiments, a carbocyclic group is polycyclic.

The term "alkyl," as used herein, refers to saturated, straight- or branched-chain hydrocarbon radicals derived from an aliphatic moiety containing between one and six carbon atoms by removal of a single hydrogen atom. Unless otherwise specified, alkyl groups contain 1-12 carbon atoms. In certain embodiments, alkyl groups contain 1-8 carbon atoms. In certain embodiments, alkyl groups contain 1-6 carbon atoms. In some embodiments, alkyl groups contain 1-5 carbon atoms, in some embodiments, alkyl groups contain 1-4 carbon atoms, in yet other embodiments alkyl groups contain 1-3 carbon atoms, and in yet other embodiments alkyl groups contain 1-2 carbon atoms. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like.

The term "alkenyl," as used herein, denotes a monovalent group derived from a straight- or branched-chain aliphatic moiety having at least one carbon-carbon double bond by the removal of a single hydrogen atom. Unless otherwise specified, alkenyl groups contain 2-12 carbon atoms. In certain embodiments, alkenyl groups contain 2-8 carbon atoms. In certain embodiments, alkenyl groups contain 2-6 carbon atoms. In some embodiments, alkenyl groups contain 2-5 carbon atoms, in some embodiments, alkenyl groups contain 2-4 carbon atoms, in yet other embodiments alkenyl groups contain 2-3 carbon atoms, and in yet other embodiments alkenyl groups contain 2 carbon atoms. Alkenyl groups include, for example, ethenyl, propenyl, butenyl, 1-methyl-2-buten-1-yl, and the like.

The term "alkynyl," as used herein, refers to a monovalent group derived from a straight- or branched-chain aliphatic moiety having at least one carbon-carbon triple bond by the removal of a single hydrogen atom. Unless otherwise specified, alkynyl groups contain 2-12 carbon atoms. In certain embodiments, alkynyl groups contain 2-8 carbon atoms. In certain embodiments, alkynyl groups contain 2-6 carbon atoms. In some embodiments, alkynyl groups contain 2-5 carbon atoms, in some embodiments, alkynyl groups contain 2-4 carbon atoms, in yet other embodiments alkynyl groups contain 2-3 carbon atoms, and in yet other embodiments alkynyl groups contain 2 carbon atoms. Representative alkynyl groups include, but are not limited to, ethynyl, 2-propynyl (propargyl), 1-propynyl, and the like.

The term "carbocycle" and "carbocyclic ring" as used herein, refers to monocyclic and polycyclic moieties wherein the rings contain only carbon atoms. Unless otherwise specified, carbocycles may be saturated, partially unsaturated or aromatic, and contain 3 to 20 carbon atoms. Representative carbocyles include cyclopropane, cyclobutane, cyclopentane, cyclohexane, bicyclo[2,2,1]heptane, norbornene, phenyl, cyclohexene, naphthalene, spiro[4.5]decane.

The term acyl group refers to a moiety wherein an acyl group is attached to another moiety, e.g.,

wherein E is an aliphatic group, carbocyclic group, aryl or heterocyclic group, including heteroaryl group, as these groups are as defined herein.

The term "aryl" used alone or as part of a larger moiety as in "aralkyl", "aralkoxy", or "aryloxyalkyl", refers to monocyclic and polycyclic ring systems having a total of five to 20 ring members, wherein at least one ring in the system is aromatic and wherein each ring in the system contains three to twelve ring members. The term "aryl" may be used interchangeably with the term "aryl ring". In certain embodiments of the present invention, "aryl" refers to an aromatic ring system which includes, but is not limited to, phenyl, biphenyl, naphthyl, anthracyl and the like, which may bear one or more substituents. Also included within the scope of the term "aryl", as it is used herein, is a group in which an aromatic ring is fused to one or more additional rings, such as benzofuranyl, indanyl, phthalimidyl, naphthimidyl, phenantriidinyl, or tetrahydronaphthyl, and the like.

The terms "heteroaryl" and "heteroar-", used alone or as part of a larger moiety, e.g., "heteroaralkyl", or "heteroaralkoxy", refer to groups having 5 to 14 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, benzofuranyl and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3 (4H)-one. A heteroaryl group may be mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 5- to 7-membered monocyclic or 7-14-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

In some chemical structures herein, substituents are shown attached to a bond which crosses a bond in a ring of the depicted molecule. This means that one or more of the substituents may be attached to the ring at any available position (usually in place of a hydrogen atom of the parent ring structure). In cases where an atom of a ring so substituted has two substitutable positions, two groups may be present on the same ring atom. When more than one substituent is present, each is defined independently of the others, and each may have a different structure. In certain cases where the substituent shown crossing a bond of the ring is —R, this has the same meaning as if the ring were said to be "optionally substituted" as described in the preceding paragraph.

Suitable monovalent substituents on a substitutable carbon atom of an "optionally substituted" group are independently halogen; $-(CH_2)_{0-4}R^\circ$; $-(CH_2)_{0-4}OR^\circ$; $-O-(CH_2)_{0-4}C(O)OR^\circ$; $-(CH_2)_{0-4}-CH(OR^\circ)_2$; $-(CH_2)_{0-4}SR^\circ$; $-(CH_2)_{0-4}Ph$, which may be substituted with $R^\circ$; $-(CH_2)_{0-4}O(CH_2)_{0-1}Ph$ which may be substituted with $R^\circ$; $-CH=CHPh$, which may be substituted with $R^\circ$; $-NO_2$; $-CN$; $-N_3$; $-(CH_2)_{0-4}N(R^\circ)_2$; $-(CH_2)_{0-4}N(R^\circ)C(O)R^\circ$; $-N(R^\circ)C(S)R^\circ$; $-(CH_2)_{0-4}N(R^\circ)C(O)NR^\circ_2$; $-N(R^\circ)C(S)NR^\circ_2$; $-(CH_2)_{0-4}N(R^\circ)C(O)OR^\circ$; $-N(R^\circ)N(R^\circ)C(O)R^\circ$; $-N(R^\circ)N(R^\circ)C(O)NR^\circ_2$; $-N(R^\circ)N(R^\circ)C(O)OR^\circ$; $-(CH_2)_{0-4}C(O)R^\circ$; $-C(S)R^\circ$; $-(CH_2)_{0-4}C(O)OR^\circ$; $-(CH_2)_{0-4}C(O)N(R^\circ)_2$; $-(CH_2)_{0-4}C(O)SR^\circ$; $-(CH_2)_{0-4}C(O)OSiR^\circ_3$; $-(CH_2)_{0-4}OC(O)R^\circ$; $-OC(O)(CH_2)_{0-4}SR-$, $SC(S)SR^\circ$; $-(CH_2)_{0-4}SC(O)R^\circ$; $-(CH_2)_{0-4}C(O)NR^\circ_2$; $-C(S)NR^\circ_2$; $-C(S)SR^\circ$; $-SC(S)SR^\circ$, $-(CH_2)_{0-4}OC(O)NR^\circ_2$; $-C(O)N(OR^\circ)R^\circ$; $-C(O)C(O)R^\circ$; $-C(O)CH_2C(O)R^\circ$; $-C(NOR^\circ)R^\circ$; $-(CH_2)_{0-4}SSR^\circ$; $-(CH_2)_{0-4}S(O)_2R^\circ$; $-(CH_2)_{0-4}S(O)_2OR^\circ$; $-(CH_2)_{0-4}OS(O)_2R^\circ$; $-S(O)_2NR^\circ_2$; $-(CH_2)_{0-4}S(O)R^\circ$; $-N(R^\circ)S(O)_2NR^\circ_2$; $-N(R^\circ)S(O)_2R^\circ$; $-N(OR^\circ)R^\circ$; $-C(NH)NR^\circ_2$; $-P(O)_2R^\circ$; $-P(O)R^\circ_2$; $-OP(O)R^\circ_2$; $-OP(O)(OR^\circ)_2$; $SiR^\circ_3$; $-(C_{1-4}$ straight or branched)alkylene)O$-N(R^\circ)_2$; or $-(C_{1-4}$ straight or branched)alkylene)C(O)O$-N(R^\circ)_2$, wherein each $R^\circ$ may be substituted as defined below and is independently hydrogen, $C_{1-8}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or polycyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, $-(CH_2)_{0-2}R^\bullet$, -(haloR$^\bullet$), $-(CH_2)_{0-2}OH$, $-(CH_2)_{0-2}OR^\bullet$, $-(CH_2)_{0-2}CH(OR^\bullet)_2$; $-O(haloR^\bullet)$, $-CN$, $-N_3$, $-(CH_2)_{0-2}C(O)R^\bullet$, $-(CH_2)_{0-2}C(O)OH$, $-(CH_2)_{0-2}C(O)OR^\bullet$, $-(CH_2)_{0-4}C(O)N(R^\circ)_2$; $-(CH_2)_{0-2}SR^\bullet$, $-(CH_2)_{0-2}SH$, $-(CH_2)_{0-2}NH_2$, $-(CH_2)_{0-2}NHR^\bullet$, $-(CH_2)_{0-2}NR^\bullet_2$, $-NO_2$, $-SiR^\bullet_3$, $-OSiR^\bullet_3$, $-C(O)SR^\bullet$, $-(C_{1-4}$ straight or branched alkylene)C(O)OR$^\bullet$, or $-SSR^\bullet$ wherein each $R^\bullet$ is unsubstituted or where preceded by "halo" is substituted only with one or more halogens, and is independently selected from $C_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R$^\circ$ include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger$$_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger$$_2$, —C(S)NR$^\dagger$$_2$, —C(NH)NR$^\dagger$$_2$, or —N(R)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

BRIEF DESCRIPTION OF THE DRAWINGS

FIG. 19 shows the cytotoxity profiles of extracts from *Guaiacum scanctum* bark against human breast cell cancer lines SKBR-3, BT-20, MB-MDA-468, MB-MDA-453, and MB-MDA-231 as assessed by Alamar Blue Assay. +++=good activity, ++=moderate activity, +=slight activity, and –=no activity.

FIG. 23 shows the cytotoxity profiles of extracts from the bark and wood of *Guaiacum scanctum* against human cancer lines Calu-6, HCT-116, Hela, and MFC-7, as assessed by Alamar Blue Assay. +++=good activity, ++=moderate activity, +=slight activity, and –=no activity.

FIG. 27 indicates the relative cytotoxic activity in cell line MD-MBA 231 of fractions from the heartwood of *Guaiacum sanctum* L (FIG. 27A) and cytotoxic activity for cell lines MB-MDA-468, SKBR-3 and MCF-7 of fractions from the heartwood of *Guaiacum officinale* L (FIG. 27B).

DETAILED DESCRIPTION OF EMBODIMENTS OF THE INVENTION

Figure 1:
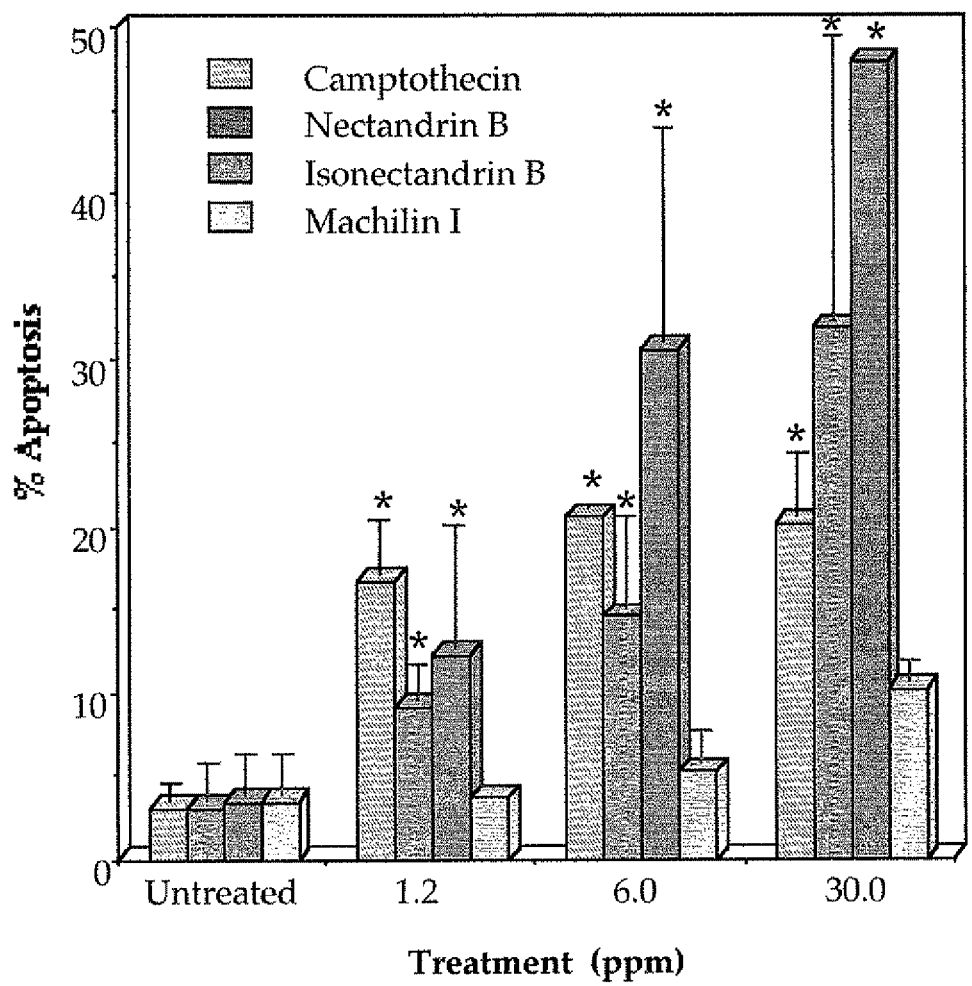
FIG. 1 shows the effect of nectandrin B, isonectandrin B and machilin I on the induction of early stage apoptosis in human breast cancer cell line MD-MBA 231. Cells were exposed at various doses for 24 hr. Analysis was determined by FACS, Annexin V_FITC and PI staining. DNA topoisomerase 1 inhibitor camptothecin was used as a positive control. Treatment means with an * are statistically different from the control group at the 5% level according to Fisher's Projected LSD (SuperANOVA 1989).

In certain embodiments, the present disclosure encompasses novel compounds having formula I, or a pharmaceutically acceptable salt thereof,

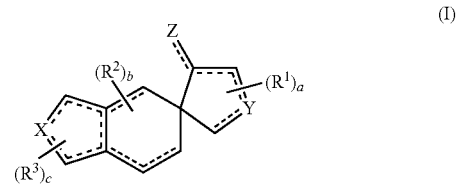

(I)

wherein,
X is a divalent moiety selected from: —O—; —S(O)$_x$—; —N(R$^y$)—; —CH$_2$O—; —OCH$_2$—; —C(O)O—; —OC(O)—; —CH$_2$N(R$^y$)—; —C(O)N(R$^y$)—; —N(R$^y$)CH$_2$—; —NR$^y$C(O)—; and —(CR$^y$)$_2$—;
Y is a divalent moiety selected from: —O—; —S(O)$_x$—; —N(R$^y$)—; —CH$_2$O—; —OCH$_2$—; —C(O)(O)—, —OC(O)—; —CH$_2$N(R$^y$)—; —C(O)N(R)— and —N(R$^y$)CH$_2$—; —NR$^y$C(O)—; and —C(R$^y$)$_2$—;

Z is selected from: =C(R$^4$)$_2$; =O; =NR$^y$; =NOR$^z$; =NN(R$^y$)$_2$;
—N(R$^y$)$_2$; —OR$^z$; —S(O)$_x$R$^y$; C$_{1-20}$ aliphatic; C$_{1-20}$ heteroaliphatic having 1-4 heteroatoms independently selected from the group consisting of nitrogen, oxygen, and sulfur; 6- to 14-membered aryl; 5- to 14-membered heteroaryl having 1-4 heteroatoms independently selected from nitrogen, oxygen, or sulfur; and 4-7-membered heterocyclic having 1-3 heteroatoms independently selected from the group consisting of nitrogen, oxygen, and sulfur;

each R$^1$, may be the same or different, each R$^2$ may be the same or different, and each R$^3$ may be the same or different and, at each occurrence are independently halogen; CN; —S(O)$_x$R$^y$—; —NR$^y$C(O)R$^y$; —OC(O)R$^y$; —CO$_2$R$^y$; NCO; —N$_3$; —OR$^z$; —OC(O)N(R$^y$)$_2$; N(R)$_2$; —NR$^y$C(O)R$^y$ and —NR$^y$C(O)OR$^y$; or an optionally substituted group selected from the group consisting of C$_{1-20}$ aliphatic; C$_{1-20}$ heteroaliphatic having 1-4 heteroatoms independently selected from the group consisting of nitrogen, oxygen and sulfur; 6-14-membered aryl; 5 to 14 membered heteroaryl having 1-4 heteroatoms independently selected from nitrogen, oxygen and sulfur and 4- to 7-membered heterocyclic having 1-3 heteroatoms independently selected from nitrogen, oxygen and sulfur, where two or more adjacent R$^1$, R$^2$ and R$^3$ groups can be taken together with any intervening atoms to form an optionally substituted, saturated, partially unsaturated or aromatic 5 to 12 membered ring containing 0 to 4 heteroatoms and where two R$^1$, R$^2$ or R$^3$ groups attached to the same carbon may be taken together to form a moiety selected from =O, =NOR$^z$, =NN(R$^y$)$_2$, =C(R$^y$)$_2$ and an optionally substituted, saturated partially unsaturated 3 to 8-membered spirocyclic ring containing 0 to 4 heteroatoms selected from nitrogen, oxygen and sulfur;

R$^4$ is, at each occurrence, independently selected from: hydrogen; or an optionally substituted moiety selected from C$_{1-20}$ aliphatic; C$_{1-20}$ heteroaliphatic having 1-4 heteroatoms; 6- to 14-membered aryl; 5- to 10-membered heteroaryl; and 4- to 7-membered heterocyclic, where two R$^4$ groups may be taken together to form a moiety selected from the group consisting of: =O; =NOR$^z$; =NN(R$^y$)$_2$; =C(R$^y$)$_2$; and an optionally substituted, saturated or partially unsaturated 3- to 8-membered spirocyclic ring containing 0 to 4 heteroatoms, R$^y$ is at each occurrence, independently selected from the group consisting of: hydrogen and an optionally substituted C$_{1-12}$ aliphatic group, R$^z$ is at each occurrence, independently selected from: hydrogen, an optionally substituted C$_{1-12}$ aliphatic, an optionally substituted C$_{2-20}$ acyl group,

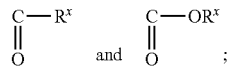

and, R$^x$ is hydrogen or an optionally substituted moiety selected from C$_{1-20}$ aliphatic; C$_{1-20}$ heteroaliphatic having 1-4 heteroatoms; 6- to 14-membered aryl; 5- to 10-membered heteroaryl; and 4- to 7-membered heterocyclic;

x is 0, 1, or 2,
a is 0, 1, 2, 3, 4, or 5,
b is 0, 1, 2, 3, 4, 5, 6, 7, or 8,
c is 0, 1, 2, 3, 4, 5, or 6, and
---- represents an optionally substituted bond that is either a single bond or a double bond.

In the formula I hereinabove, it is understood from the definition of Z that it may be bonded to the ring with a single bond or double bond. Z is bonded to the ring with a double bond when it is defined as =C(R$^4$)$_2$; =O, =NR$^y$; =NOR$^{-z}$ or =NN(R$^y$)$_z$; for all other definitions of Z, Z is bonded to the ring by a single bond. Y and X in the definition are bonded to the adjacent carbon ring atom by a double bond when they are =N—; otherwise the bonds to X and Y are single bonds.

As defined hereinabove, the term "wherein two or more adjacent R$^1$, R$^2$ and R$^3$ groups can be taken together with any intervening atoms to form a optionally substituted saturated, partially unsaturated or aromatic 5 to 12-membered ring containing 0 to 4 heteroatoms "signifies that any two R$^1$'s, R$^2$'s, R$^3$'s or R$^1$ and R$^2$ or R$^2$ and R$^3$ groups may be taken together with any intervening atoms to form a ring which is cycloaliphatic or aromatic, or heterocyclic, including heteroaromatic. Thus, for example, two R$^1$ groups may be taken together, or an R$^1$ and R$^2$ group can be taken together.

By "partially unsaturated" it is meant that it is not aromatic, but it contains multiple carbon carbon double or triple bonds or carbon-nitrogen double bonds in the ring.

In formula I, it is understood that the valances of each carbon atom is 4, each nitrogen atom is 3 and each oxygen atom s 2. Further, it is understood that the ring atoms do not have two double bonds in succession, i.e., no one ring atom, except sulfur has more than 1 double bond bonded to the same ring atom in any one position. For example, if X is =N, the other bond attached to X in the ring must be a single bond.

Moreover, it is to be noted that the substituents on the ring are (R$^1$)a, (R$^2$)b and (R$^3$)c, wherein a is 0-5, b is 0-8 and c is 0-6. It is to be understood that (R$_1$)$_o$ is a hydrogen, (R$^2$)o is hydrogen and (R$^3$)$_o$ is hydrogen. Moreover, the definition of X includes S(O)x, when x is 0-2. When x is 0, in this embodiment, X is S.

In an embodiment, one of X and Y is not N(R$^y$), CHN(R$^y$), N(R$^y$)CH$_2$ or C(R$^y$)$_2$ and one of R$^1$, R$^2$ and R$^3$ is not =O or =C(R$^y$)$_2$.

In another embodiment X is a divalent moiety selected from: —O—; —S(O)$_x$—; —CH$_2$O—; —OCH$_2$—; —C(O)O—; —OC(O)—; —CH$_2$N(R$^y$)—; —C(O)N(R$^y$)—; and —N(R$^y$)C(O)—;

Y is a divalent moiety selected from: —O—; —S(O)$_x$—; —N(R$^y$)—; —CH$_2$O—; —OCH$_2$—; —C(O)O—; —OC(O)—; —CH$_2$N(R$^y$)—; —C(O)N(R$^y$)—; —N(R$^y$)CH$_2$—; and —N(R$^y$)C(O)—; and —C(R$^y$)$_2$—, Z is selected from: =C(R$^4$)$_2$; =O; =NR$^y$; =NOR$^z$; =NN(R$^y$)$_2$;
—N(R$^y$)$_2$; —OR$^z$; —S(O)$_x$R$^y$; C$_{1-20}$ aliphatic; C$_{1-20}$ heteroaliphatic having 1-4 heteroatoms independently selected from the group consisting of nitrogen, oxygen, and sulfur; 6- to 14-membered aryl; 5- to 14-membered heteroaryl having 1-4 heteroatoms independently selected from nitrogen, oxygen, or sulfur; and 4-7-membered heterocyclic having 1-3 heteroatoms independently selected from the group consisting of nitrogen, oxygen, and sulfur, R$^1$, R$^2$, and R$^3$, are, at each occurrence independently selected from the group consisting of: halogen; —CN; —S(O)$_x$R$^y$; —NR$^y$C(O)R$^y$; —OC(O)R$^y$; —CO$_2$R$^y$; —NCO; —N$_3$; —OR$^z$; —OC(O)N(R$^y$)$_2$; —N(R$^y$)$_2$; —NR$^y$C(O)R$^y$; and —NR$^y$C(O)OR$^y$; or an optionally substituted group selected from the group consisting of C$_{1-20}$ aliphatic; C$_{1-20}$ heteroaliphatic having 1-4 heteroatoms independently selected from the group consisting of nitrogen, oxygen, and sulfur; 6- to 14-membered aryl; 5- to 14-membered heteroaryl having 1-4 heteroatoms independently selected from nitrogen, oxygen, or sulfur;

and 4- to 7-membered heterocyclic having 1-3 heteroatoms independently selected from the group consisting of nitrogen, oxygen, and sulfur, where two or more adjacent $R^1$, $R^2$ and $R^3$ groups can be taken together with any intervening atoms to form an optionally substituted saturated, partially unsaturated, or aromatic 5- to 12-membered ring containing 0 to 4 heteroatoms; and where two $R^1$, $R^2$ or $R^3$ groups attached to the same carbon atom may be taken together to form a moiety selected from the group consisting of: =O; =$NOR^z$; =$NN(R^y)_2$; =$C(R^y)_2$ and an optionally substituted, saturated or partially unsaturated 3-8 membered spirocyclic ring containing 0 to 4 heteroatoms, $R^4$ is, at each occurrence, independently selected from: hydrogen; or an optionally substituted moiety selected from the group consisting of $C_{1-20}$ aliphatic; $C_{1-20}$ heteroaliphatic having 1-4 heteroatoms; 6- to 14-membered aryl; 5- to 10-membered heteroaryl; and 4- to 7-membered heterocyclic, where two $R^4$ groups may be taken together to form a moiety selected from the group consisting of: =$NOR^z$; =$NN(R^y)_2$; and an optionally substituted, saturated or partially unsaturated 3- to 8-membered spirocyclic ring containing 0 to 4 heteroatoms, $R^y$ is at each occurrence, independently selected from: hydrogen and an optionally substituted $C_{1-12}$ aliphatic group, $R^z$ is at each occurrence, independently selected from: hydrogen, an optionally substituted $C_{1-12}$ aliphatic, an optionally substituted $C_{2-20}$ acyl group,

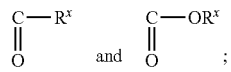

$R^x$ is hydrogen or an optionally substituted moiety selected from $C_{1-20}$ aliphatic; $C_{1-20}$ heteroaliphatic having 1-4 heteroatoms; 6- to 14-membered aryl; 5- to 10-membered heteroaryl; and 4- to 7-membered heterocyclic;

x is 0, 1, or 2,
a is 0, 1, 2, 3, 4, or 5,
b is 0, 1, 2, 3, 4, 5, 6, 7, or 8,
c is 0, 1, 2, 3, 4, 5, or 6, and
---- represents an optionally substituted bond that is either a single bond or a double bond.

In still another embodiment, X is a divalent moiety selected from: —O—; —$S(O)_x$—; —$N(R^y)$—; —$CH_2O$—; —$OCH_2$—; —C(O)O—; —OC(O)—; —$CH_2N(R^y)$—; —$C(O)N(R^y)$—; —$N(R^y)CH_2$—; —$N(R^y)C(O)$—; and —$C(R^y)_2$—, Y is a divalent moiety selected: —O—; —$S(O)_x$—; —$CH_2O$—; —$OCH_2$—; —C(O)O—; —OC(O)—; —$C(O)N(R^y)$—; and —$N(R^y)C(O)$—;

Z is selected from =$C(R^4)_2$; =O; =$NR^y$; =$NOR^z$; =$NN(R^y)_2$;
—$N(R^y)_2$; —$OR^z$; —$S(O)_xR^y$; $C_{1-20}$ aliphatic; $C_{1-20}$ heteroaliphatic having 1-4 heteroatoms independently selected from the group consisting of nitrogen, oxygen, and sulfur; 6- to 14-membered aryl; 5- to 14-membered heteroaryl having 1-4 heteroatoms independently selected from nitrogen, oxygen, or sulfur; and 4-7-membered heterocyclic having 1-3 heteroatoms independently selected from the group consisting of nitrogen, oxygen, and sulfur, $R^1$, $R^2$, and $R^3$, are, at each occurrence independently selected from: halogen; —CN; —$S(O)_xR^y$; —$NR^yC(O)R^y$; —$OC(O)R^y$; —$CO_2R^y$; —NCO; —$N_3$; —$OR^z$; —$OC(O)N(R^y)_2$; —$N(R^y)_2$; —$NR^yC(O)R^y$; and —$NR^yC(O)OR^y$; or an optionally substituted group selected from the group consisting of $C_{1-20}$ aliphatic; $C_{1-20}$ heteroaliphatic having 1-4 heteroatoms independently selected from the group consisting of nitrogen, oxygen, and sulfur; 6- to 14-membered aryl; 5- to 14-membered heteroaryl having 1-4 heteroatoms independently selected from nitrogen, oxygen, or sulfur; and 4- to 7-membered heterocyclic having 1-3 heteroatoms independently selected from the group consisting of nitrogen, oxygen, and sulfur, where two or more adjacent $R^1$, $R^2$ and $R^3$ groups can be taken together with any intervening atoms to form an optionally substituted saturated, partially unsaturated, or aromatic 5- to 12-membered ring containing 0 to 4 heteroatoms; and where two $R^1$, $R^2$ or $R^3$ groups attached to the same carbon atom may be taken together to form a moiety selected from the group consisting of: =$NOR^z$; =$NN(R^y)_2$ and an optionally substituted, saturated or partially unsaturated 3-8 membered spirocyclic ring containing 0 to 4 heteroatoms, $R^4$ is, at each occurrence, independently selected from the group consisting of: hydrogen; or an optionally substituted moiety selected from the group consisting of $C_{1-20}$ aliphatic; $C_{1-20}$ heteroaliphatic having 1-4 heteroatoms; 6- to 14-membered aryl; 5- to 10-membered heteroaryl; and 4- to 7-membered heterocyclic, where two $R^4$ groups may be taken together to form a moiety selected from the group consisting of: =O; =$NOR^z$; =$NN(R^y)_2$; =$C(R^y)_2$; and an optionally substituted, saturated or partially unsaturated 3- to 8-membered spirocyclic ring containing 0 to 4 heteroatoms, $R^y$ is at each occurrence, independently selected from the group consisting of: hydrogen and an optionally substituted $C_{1-12}$ aliphatic group, $R^z$ is at each occurrence, independently selected from the group consisting of: hydrogen, an optionally substituted $C_{1-12}$ aliphatic, an optionally substituted $C_{2-20}$ acyl group,

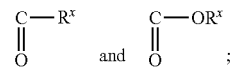

$R^x$ is hydrogen or an optionally substituted moiety selected from $C_{1-20}$ aliphatic; $C_{1-20}$ heteroaliphatic having 1-4 heteroatoms; 6- to 14-membered aryl; 5- to 10-membered heteroaryl; and 4- to 7-membered heterocyclic;

x is 0, 1, or 2,
a is 0, 1, 2, 3, 4, or 5,
b is 0, 1, 2, 3, 4, 5, 6, 7, or 8,
c is 0, 1, 2, 3, 4, 5, or 6, and
---- represents an optionally substituted bond that is either a single bond or a double bond.

In another embodiment, X is a divalent moiety selected from the group consisting of: —O—; —$S(O)_x$—; —$CH_2O$—; —$OCH_2$—; —C(O)O—; —OC(O)—; —$CH_2N(R^y)$—; —$C(O)N(R^y)$—; and —$N(R^y)C(O)$—;

Y is a divalent moiety selected from the group consisting of —O—; —$S(O)_x$—; —$CH_2O$—; —$OCH_2$—; —C(O)O—; —OC(O)—; —$CH_2N(R^y)$—; —$C(O)N(R^y)$—; and —$N(R^y)C(O)$—;

Z is selected from the group consisting of =$C(R^4)_2$; =O; =$NR^y$; =$NOR^z$; =$NN(R^y)_2$; —$N(R^y)_2$; —$OR^z$; —$S(O)_xR^y$; $C_{1-20}$ aliphatic; $C_{1-20}$ heteroaliphatic having 1-4 heteroatoms independently selected from the group consisting of nitrogen, oxygen, and sulfur; 6- to 14-membered aryl; 5- to 14-membered heteroaryl having 1-4 heteroatoms independently selected from nitrogen, oxygen, or sulfur; and 4-7-membered heterocyclic having 1-3 heteroatoms independently selected from the group consisting of nitrogen, oxygen, and sulfur, $R^1$, $R^2$, and $R^3$, are, at each occurrence independently selected from the group consisting of: halogen; —CN; —S(O)$_x$R$^y$; —NR$^y$C(O)R$^y$; —OC(O)R$^y$; —CO$_2$R$^y$; —NCO; —N$_3$; —OR$^z$; —OC(O)N(R$^y$)$_2$; —N(R$^y$)$_2$; —NR$^y$C(O)R$^y$; and —NR$^y$C(O)OR$^y$; or an optionally substituted group selected from the group consisting of C$_{1-20}$ aliphatic; C$_{1-20}$ heteroaliphatic having 1-4 heteroatoms independently selected from the group consisting of nitrogen, oxygen, and sulfur; 6- to 14-membered aryl; 5- to 14-membered heteroaryl having 1-4 heteroatoms independently selected from nitrogen, oxygen, or sulfur; and 4- to 7-membered heterocyclic having 1-3 heteroatoms independently selected from the group consisting of nitrogen, oxygen, and sulfur, where two or more adjacent $R^1$, $R^2$ and $R^3$ groups can be taken together with any intervening atoms to form an optionally substituted saturated, partially unsaturated, or aromatic 5- to 12-membered ring containing 0 to 4 heteroatoms; and where two $R^1$, $R^2$ or $R^3$ groups attached to the same carbon atom may be taken together to form a moiety selected from the group consisting of: =NOR$^z$; =NN(R$^y$)$_2$; and an optionally substituted, saturated or partially unsaturated 3-8 membered spirocyclic ring containing 0 to 4 heteroatoms, $R^4$ is, at each occurrence, independently selected from the group consisting of: hydrogen; or an optionally substituted moiety selected from the group consisting of C$_{1-20}$ aliphatic; C$_{1-20}$ heteroaliphatic having 1-4 heteroatoms; 6- to 14-membered aryl; 5- to 10-membered heteroaryl; and 4- to 7-membered heterocyclic, where two $R^4$ groups may be taken together to form a moiety selected from the group consisting of: =O; =NOR$^z$; =NN(R$^y$)$_2$; =C(R$^y$)$_2$; and an optionally substituted, saturated or partially unsaturated 3- to 8-membered spirocyclic ring containing 0 to 4 heteroatoms, $R^y$ is at each occurrence, independently selected from the group consisting of hydrogen and an optionally substituted C$_{1-12}$ aliphatic group, $R^z$ is at each occurrence, independently selected from the group consisting of: hydrogen, an optionally substituted C$_{1-12}$ aliphatic, an optionally substituted C$_{2-20}$ acyl group

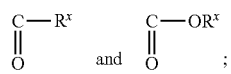

$R^X$ is hydrogen or an optionally substituted moiety selected from C$_{1-20}$ aliphatic; C$_{1-20}$ heteroaliphatic having 1-4 heteroatoms; 6- to 14-membered aryl; 5- to 10-membered heteroaryl; and 4- to 7-membered heterocyclic x is 0, 1, or 2, a is 0, 1, 2, 3, 4, or 5, b is 0, 1, 2, 3, 4, 5, 6, 7, or 8, c is 0, 1, 2, 3, 4, 5, or 6, and ---- represents an optionally substituted bond that is either a single bond or a double bond.

In another embodiment,

X is a divalent moiety selected from the group consisting of: —O—; —S(O)$_x$—; —N(R$^y$)—; —CH$_2$O—; —OCH$_2$—; —CH$_2$N(R$^y$)—; or —N(R$^y$)CH$_2$—;

Y is a divalent moiety selected from the group consisting of: —O—; —S(O)$_x$—; —N(R$^y$)—; —CH$_2$O—; —OCH$_2$—; —CH$_2$N(R$^y$)—; or —N(R$^y$)CH$_2$—;

Z is selected from the group consisting of =C(R$^4$)$_2$; =O; =NR$^y$; =NOR$^z$; =NN(R$^y$)$_2$; —N(R$^y$)$_2$; —OR$^z$; —S(O)$_x$R$^y$; C$_{1-20}$ aliphatic; C$_{1-20}$ heteroaliphatic having 1-4 heteroatoms independently selected from the group consisting of nitrogen, oxygen, and sulfur; 6- to 14-membered aryl; 5- to 14-membered heteroaryl having 1-4 heteroatoms independently selected from nitrogen, oxygen, or sulfur; and 4-7-membered heterocyclic having 1-3 heteroatoms independently selected from the group consisting of nitrogen, oxygen, and sulfur, each $R^1$, may be the same or different, each $R^2$ may be the same or different, and each $R^3$ may be the same or different and are, at each occurrence independently optionally substituted 6- to 14-membered aryl;

$R^4$ is, at each occurrence, independently selected from the group consisting of: hydrogen; or an optionally substituted moiety selected from the group consisting of C$_{1-20}$ aliphatic; C$_{1-20}$ heteroaliphatic having 1-4 heteroatoms; 6- to 14-membered aryl; 5- to 10-membered heteroaryl; and 4- to 7-membered heterocyclic, where two $R^4$ groups may be taken together to form a moiety selected from the group consisting of: =O; =NOR$^z$; =NN(R$^y$)$_2$; =C(R$^y$)$_2$; and an optionally substituted, saturated or partially unsaturated 3- to 8-membered spirocyclic ring containing 0 to 4 heteroatoms, $R^y$ is at each occurrence, independently selected from the group consisting of: hydrogen and an optionally substituted C$_{1-12}$ aliphatic group, $R^z$ is at each occurrence, independently selected from the group consisting of: hydrogen, an optionally substituted C$_{1-12}$ aliphatic, and an optionally substituted C$_{2-20}$ acyl group;

x is 0, 1, or 2, a is 0, 1, 2, 3, 4, or 5, b is 0, 1, 2, 3, 4, 5, 6, 7, or 8, c is 0, 1, 2, 3, 4, 5, or 6, and ---- represents an optionally substituted bond that is either a single bond or a double bond.

In another embodiment, X and Y are independently O, S(O)$_n$, CH$_2$O or OCH$_2$.

In another embodiment one of X and Y is O.

In another embodiment, both X and Y are O.

In certain embodiments, the present invention encompasses compounds of formula II:

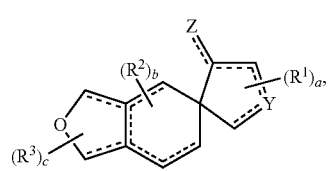

wherein, Y, Z, $R^1$, $R^2$, $R^3$, a, b, and c are as defined above.

In certain embodiments, the present invention encompasses compounds of formula III:

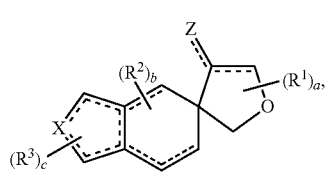

wherein, X, Z, $R^1$, $R^2$, $R^3$, a, b, and c are as defined above.

In certain embodiments, the present invention encompasses compounds of formula IV:

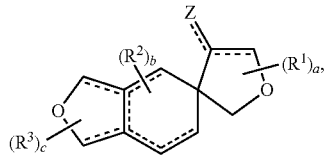

wherein, Z, $R^1$, $R^2$, $R^3$, a, b, and c are as defined above.

In certain embodiments, the present invention encompasses compounds of formula V:

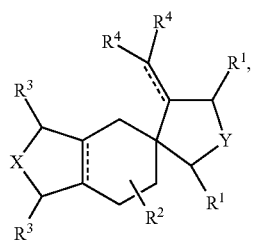

wherein, X, Y, $R^1$, $R^2$, $R^4$ and $R^3$ are as defined above. In certain embodiments, the present invention encompasses compounds of formula VI:

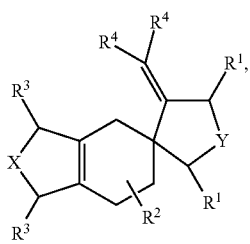

wherein, X, Y, $R^1$, $R^2$, $R^3$, and $R^4$ are as defined above.

In certain embodiments, the present invention encompasses compounds of formula VII:

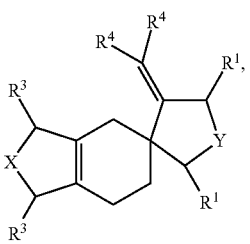

wherein, X, Y, $R^1$, $R^3$, and $R^4$ are as defined above.

In certain embodiments, the present invention encompasses compounds of formula VIII:

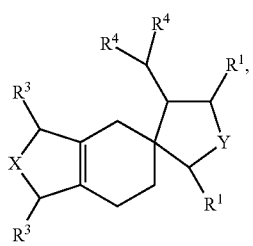

wherein, X, Y, $R^1$, $R^3$, and $R^4$ are as defined above.

In certain embodiments, the present invention encompasses compounds of formula IX:

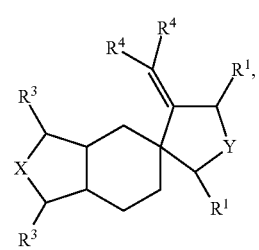

wherein, X, Y, $R^1$, $R^3$, and $R^4$ are as defined above.

In certain embodiments, the present invention encompasses compounds of formula X:

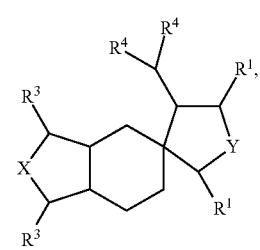

wherein, X, Y, $R^1$, $R^3$, and $R^4$ are as defined above.

In certain embodiments, the present invention encompasses compounds of formula XI:

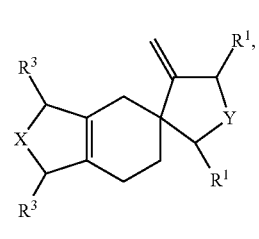

wherein, X, Y, $R^1$, and $R^3$, are as defined above.

In certain embodiments, the present invention encompasses compounds of formula XII:

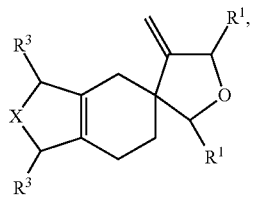

(XII)

wherein, X, $R^1$, and $R^3$ are as defined above.

In certain embodiments, the present invention encompasses compounds of formula XIII:

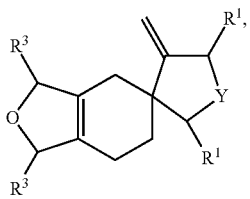

(XIII)

wherein, Y, $R^1$, and $R^3$ are as defined above.

In certain embodiments, the present invention encompasses compounds of formula XIV:

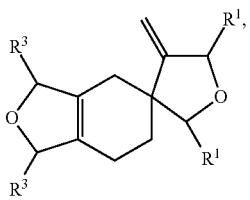

(XIV)

wherein, $R^1$, and $R^3$ are as defined above.

In certain embodiments, the present invention encompasses compounds of formula XIVa:

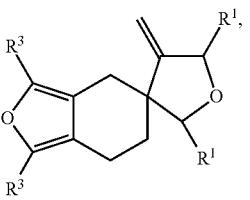

(XIVa)

wherein, $R^1$, and $R^3$ are as defined above.

In certain embodiments, the present invention encompasses compounds of formula XIVb:

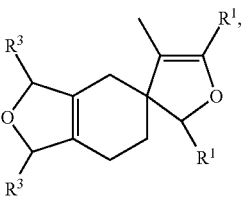

(XIVb)

wherein, $R^1$, and $R^3$ are as defined above.

In certain embodiments, the present invention encompasses compounds of formula XIVc:

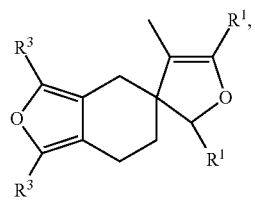

(XIVc)

wherein, $R^1$, and $R^3$ are as defined above.

In certain embodiments, the present invention encompasses compounds of formula XV:

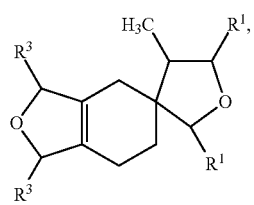

(XV)

wherein, $R^1$, and $R^3$ are as defined above.

In certain embodiments, the present invention encompasses compounds of formula XVI:

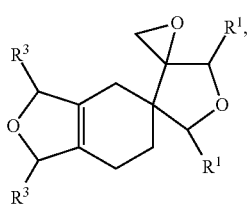

(XVI)

wherein, $R^1$, and $R^3$ are as defined above.

In certain embodiments, the present invention encompasses compounds of formula XVII:

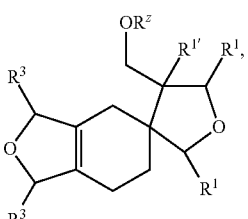

(XVII)

wherein, $R^1$, $R^3$, and $R^z$ are as defined above and $R^{1'}$ is selected from the group consisting of —H and —$OR^z$, $R^z$ is H, optionally substituted $C_{1-12}$ aliphatic, optionally substituted $C_{2-20}$ acyl group or a hydroxy protecting group.

In certain embodiments, the present invention encompasses compounds of formula XVIII:

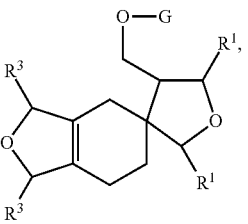

(XVIII)

wherein, $R^1$ and $R^3$ are as defined above and G represents a carbohydrate moiety, including, but not limited to saccharide or polysaccharide moieties.

In certain embodiments, G is selected from the group consisting of: hexoses such as D-glucose, D-mannose, D-xylose, D-galactose, vancosamine, 3-desmethyl-vancosamine, 3-epi-vancosamine, 4-epi-vancosamine, acosamine, actinosamine, desosamine, daunosamine, 3-epi-daunosamine, ristosamine, N-methyl-D-glucamine, D-glucuronic acid, N-acetyl-D-glucosamine, N-acetyl-D-galactosamine, sialyic acid, iduronic acid, L-fucose, and the like; pentoses such as D-ribose or D-arabinose; ketoses such as D-ribulose or D-fructose; disaccharides such as 2-O-(α-L-vancosaminyl)-β-D-glucopyranose, 2-O-(3-desmethyl α L-vancosaminyl)-β-D-glucopyranose, sucrose, lactose, or maltose; derivatives such as acetals, amines, acylated, sulfated and phosphorylated sugars; oligosaccharides having from 2 to 10 saccharide units.

In certain embodiments, the present invention encompasses compounds of formula XIX:

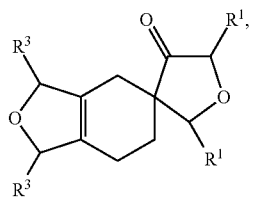

(XIX)

wherein, $R^1$ and $R^3$ are as defined above.

In certain embodiments, the present invention encompasses compounds of formula XIXa:

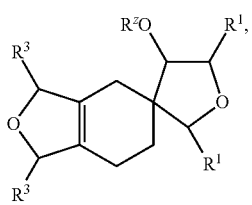

(XIXa)

wherein $R^1$, $R^3$, and $R^z$ are as defined above.

In certain embodiments, the present invention encompasses compounds of formula XIXb:

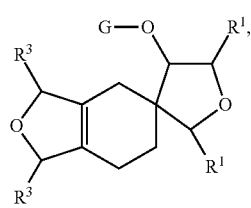

(XIXb)

wherein $R^1$, $R^3$, and G are as defined above.

In certain embodiments, the present invention encompasses compounds of formula XIXc:

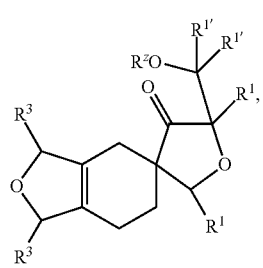

(XIXc)

wherein, $R^1$, $R^3$, and Rz are as defined above, and $R^{1'}$ is —H, or an optionally substituted moiety selected from $C_{1-20}$ aliphatic, $C_{1-20}$ heteroaliphatic, 6- to 14-membered aryl, and 5- to 14-membered heteroaryl.

In certain embodiments, the present invention encompasses compounds of formula XX:

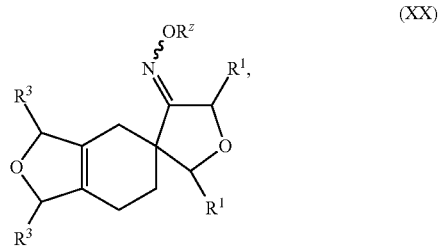

(XX)

wherein $R^1$, $R^3$, and $R^z$ are as defined above.

In the above formula, each $R^1$ may be the same or different from another $R^1$, $R^2$ or $R^3$, each $R^2$ may be the same or different from another $R^2$, $R^1$ or $R^3$, and each $R^3$ may be the same or different from each $R^3$, $R^1$ or $R^2$.

In certain embodiments where the compounds of the invention have any of formulae V through XX above, each $R^1$ is independently selected from the group consisting of 6- to 14-membered aryl; 5 to 14 membered heteroaryl having 1-4 heteroatoms independently selected from nitrogen, oxygen and sulfur; and 4-7 membered heterocyclic having 1-3 heteroatoms independently selected from nitrogen, oxygen and sulfur.

In another embodiment, $R^1$ is optionally substituted phenyl.

In certain embodiments where the compounds of the invention have any of formulae V through XX above, each $R^3$ is independently selected from the group consisting of $C_{1-20}$ aliphatic; $C_{1-20}$ heteroaliphatic having 1-4 heteroatoms; 6- to 14-membered aryl; 5 to 14 membered heteroaryl having 1-4 heteroatoms independently selected from nitrogen, oxygen and sulfur; and 4-7 membered heterocyclic having 1-3 hetereoatoms independently selected from nitrogen, oxygen and sulfur.

In another embodiment, $R^3$ is optionally substituted phenyl.

In certain embodiments where the compounds of the invention have any of formulae V through XX above, each $R^1$, and $R^3$ are independently optionally substituted 6 to 14 membered aryl group.

In certain embodiments where the compounds of the invention have any of formulae V through XX above, each $R^1$ and $R^3$ independently has a structure:

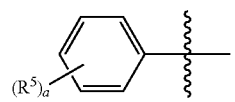

wherein:
$R^5$ is, at each occurrence, a moiety independently selected from the group consisting of: halogen; —CN; —CO$_2$R$^y$; —C(O)N(R$^y$)$_2$; —C(S)OR$^y$; —C(S)N(R$^y$)$_2$; —N(R$^y$)$_2$; —NR$^y$C(O)R$^y$; —NR$^y$C(O)OR$^y$; —NR$^y$C(O)N(R$^y$)$_2$; —NR$^y$C(S)R$^y$; —NR$^y$C(S)N(R$^y$)$_2$; —N(R$^y$)SO$_2$R$^y$; —NO$_2$; —NCO; —N$_3$; —OR$^z$; —OC(O)R$^y$; —OC(S) R$^y$; —OSO$_2$R$^y$; —OC(O)N(R$^y$)$_2$; —OC(O)OR$^y$; —S(O)$_x$R$^y$; and —S(O)$_2$N(R$^y$)$_2$; or an optionally substituted group selected from the group consisting of $C_{1-20}$ aliphatic; $C_{1-20}$ heteroaliphatic having 1-4 heteroatoms independently selected from the group consisting of nitrogen, oxygen, and sulfur; 6- to 14-membered aryl; 5- to 14-membered heteroaryl; and 3- to 7-membered heterocyclic, where two or more $R^5$ groups can be taken together with their intervening atoms to form an optionally substituted saturated, partially unsaturated, or aromatic 4- to 12-membered ring containing 0 to 4 heteroatoms, and a is 0, 1, 2, 3, 4, or 5.

$R^y$ is at each occurrence independently selected from hydrogen and an optionally substituted $C_{1-12}$ aliphatic group; and $R^z$ is at each occurrence, independently selected from hydrogen optionally substituted $C_{1-12}$ aliphatic, optionally substituted $C_{6-14}$ aryl, or optionally substituted $C_{2-20}$ acyl group.

In certain embodiments $R^5$ is —$OR^z$ at each occurrence.

In certain embodiments where the compounds of the invention have any of formulae V through XX above, each $R^1$ and $R^3$ independently has a structure:

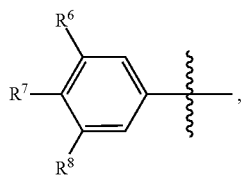

wherein $R^6$, $R^7$, and $R^8$ are each independently selected from the group consisting of: hydrogen, and —$OR^{z1}$, where $R^{z1}$ is $R^z$ as defined above or where two $R^z$ groups can optionally be taken together with their intervening atoms to form an optionally substituted ring.

In certain embodiments where the compounds of the invention have any of formulae V through XX above, each $R^1$ and $R^3$ is independently selected from the group consisting of:

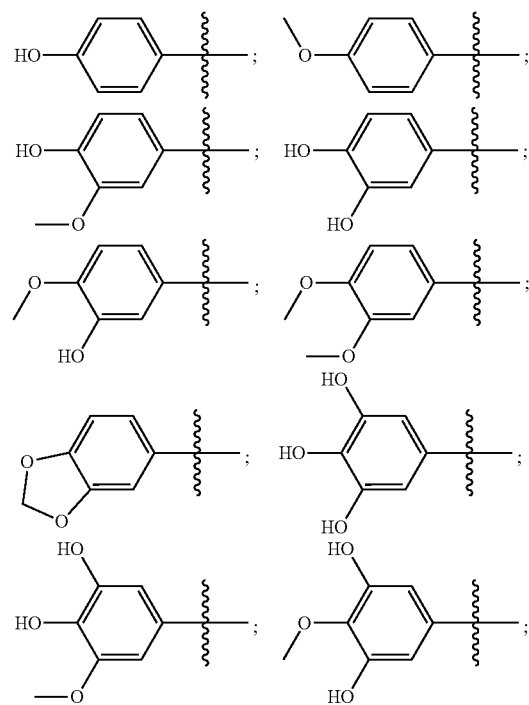

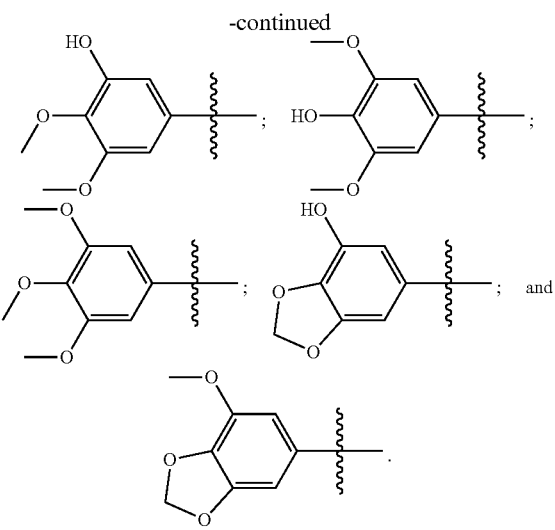

In certain embodiments where the compounds of the invention have any of formulae V through XX above, each $R^1$ and $R^3$ independently has the structure:

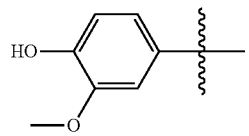

In certain embodiments where the compounds of the invention have any of formulae V through XX above, the compounds have the relative stereochemistry shown in structure (a) below:

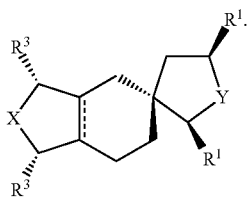

(a)

In other embodiments where the compounds of the invention have any of formulae V through XX above, the compounds have the relative stereochemistry shown in structure (b) below:

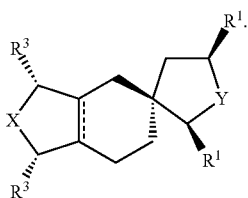

(b)

In certain embodiments, the present invention encompasses compounds of formula XXI-a or XXI-b:

(XXI-a)

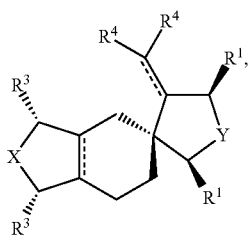

(XXI-b)

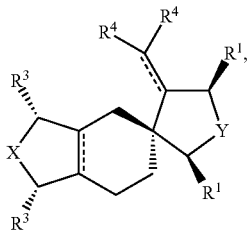

wherein, X, Y, R$^1$, R$^3$, and R$^4$ are as defined above.

In certain embodiments, the present invention encompasses compounds of formula XXII-a or XXII-b:

(XXII-a)

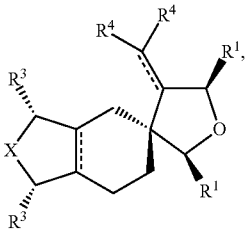

(XXII-b)

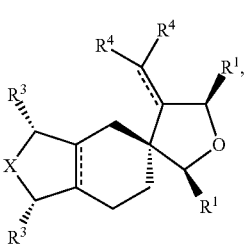

wherein, X, R$^1$, R$^3$, and R$^4$ are as defined above.

In certain embodiments, the present invention encompasses compounds of formula XXIII-a or XXIII-b.

(XXIII-a)

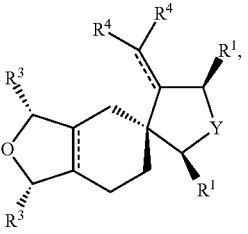

(XXIII-a)

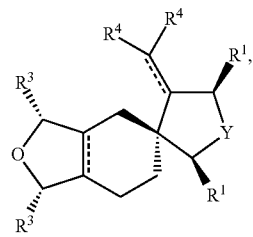

wherein, Y, R$^1$, R$^3$, and R$^4$ are as defined above.

In certain embodiments, the present invention encompasses compounds of formula XXIV-a or XXIV-b:

(XXIV-b)

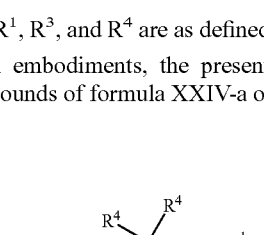

(XXIV-b)

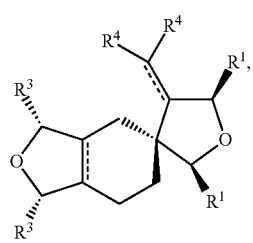

wherein R$^1$, R$^3$, and R$^4$ are as defined above.

In certain embodiments, the present invention encompasses compounds of formula XXV-a or XXV-b:

(XXV-a)

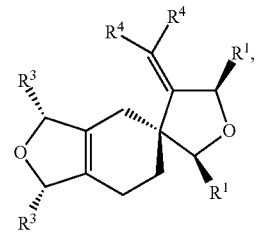

(XXV-b)

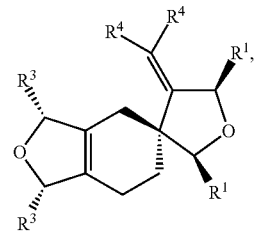

wherein R$^1$, R$^3$, and R$^4$ are as defined above.

In certain embodiments, the present invention encompasses compounds of formula XXVI-a or XXVI-b:

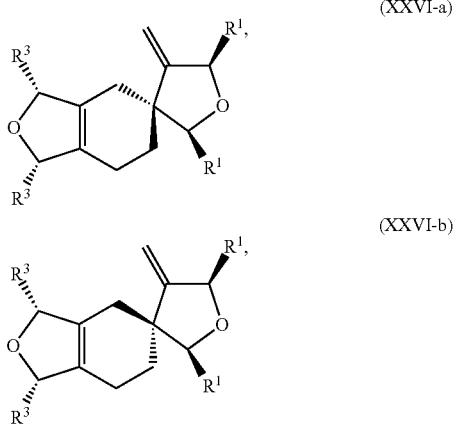

(XXVI-a)

(XXVI-b)

wherein $R^1$, and $R^3$ are as defined above.

In certain embodiments, the present invention encompasses synthetic or semisynthetic derivatives of the compounds described above. In certain embodiments, the present invention encompasses synthetic or semisynthetic derivatives of the compounds having formulae XXVI-a or XXVI-b. In a related embodiment, the present invention encompasses such methods of making such synthetic or semisynthetic derivatives.

The compounds of the present invention are prepared by art recognized techniques. For example, one method of preparing the compounds of the present invention is by performing cycloaddition under Diel Alder conditions as follows:

Scheme I

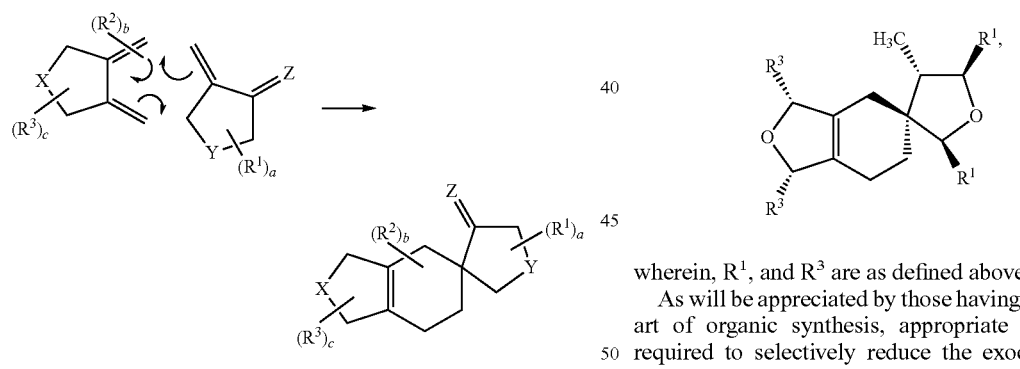

where $R^1$, $R^2$, $R^3$, X, Y, Z, a, b, and c are as defined hereinabove.

It is to be understood that the processes shown below are exemplary and even though X and Y may be indicated as O, the reactions hereinbelow can be performed as described wherein X and Y are as defined herein.

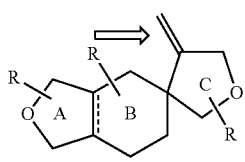

One class of semisynthetic derivatives encompassed by the present invention result from manipulation of the exocyclic double bond on ring C of the core ring system of any of the compounds above. In certain embodiments, such reactions are performed using compounds XXVI-a or XXVI-b, or mixtures thereof as starting materials.

It is to be understood herein, unless indicated to the contrary, the variable "R", as used herein refers to $R^1$, $R^2$ or $R^3$, as defined hereinabove.

In certain embodiments, this double bond can be hydrogenated (e.g. using hydrogen gas and a Pd catalyst) to yield derivatives XXVII-a through XXVII-d:

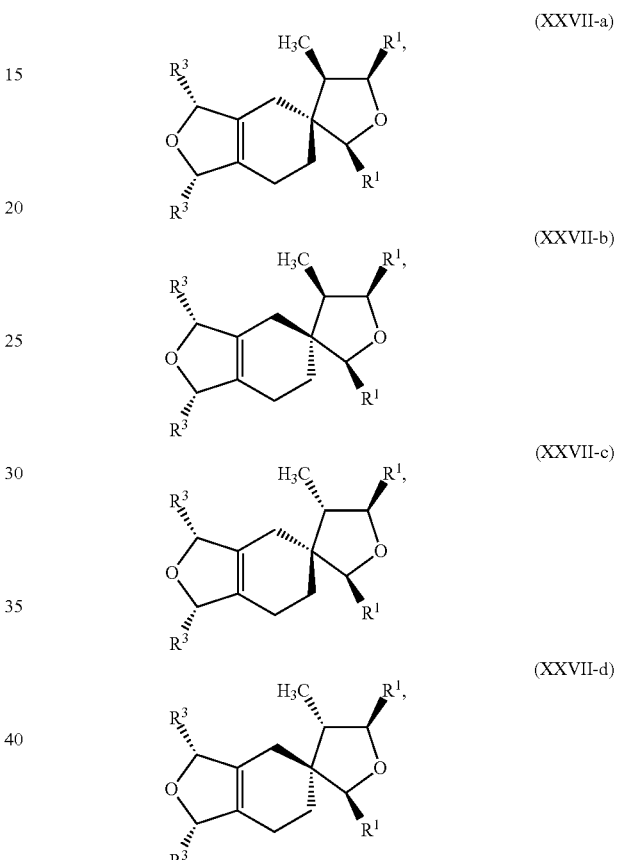

(XXVII-a)

(XXVII-b)

(XXVII-c)

(XXVII-d)

wherein, $R^1$, and $R^3$ are as defined above.

As will be appreciated by those having ordinary skill in the art of organic synthesis, appropriate conditions will be required to selectively reduce the exocyclic double bond while leaving the tetrasubstituted double bond between rings A and B unaffected, the selection of appropriate reagents and reaction conditions to affect the desired selectivity can be a matter of routine experimentation. Similarly, the stereochemistry of the resulting methyl group can be controlled by choosing appropriate catalysts and reaction conditions for the hydrogenation. Suitable techniques to achieve these selectivities may be found, for example, in: *Catalytic Hydrogenation-Techniques and Applications in Organic Synthesis* by R. L. Augustine, the entire content of which is hereby incorporated herein by reference. Alternatively, these compounds can be generated by alternate reaction sequences such as halogenation followed by hydrogenolysis.

In other embodiments, the exocyclic double bond can be oxidized.

In certain embodiments, the double bond is di-hydroxylated (e.g. with osmium tetroxide in the presence of an organic oxidant) to yield compounds of formulae XXIX-a through XXIX-d or mixtures of two or more of these:

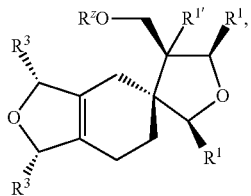
(XXIX-a)

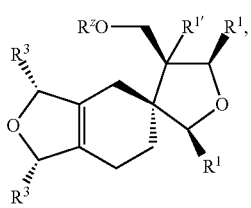
(XXIX-b)

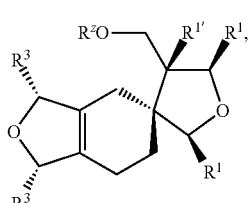
(XXIX-c)

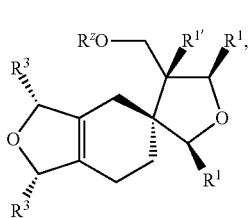
(XXIX-d)

where $R^z$ is H, $R^{1'}$ is OH, and $R^1$ and $R^3$ are as defined above.

It will be appreciated that the alcohols XXIX-a through XXIX-d can be further manipulated using reactions well known in the art to provide additional derivatives, for example they may be alkylated, acylated, glycosylated, dehydrated, phosphorylated, or sulfonylated to afford additional derivatives. Multistep schemes such allylation followed by Claisen rearrangement of the corresponding allyl ethers are also contemplated. These compounds and mixtures thereof and the methods to make them are specifically encompassed by the present disclosure.

Alternatively, compounds of the present invention can be obtained by oxidative cleavage of the exocyclic double bond to yield ketones having formulae XXX-a or XXX-b:

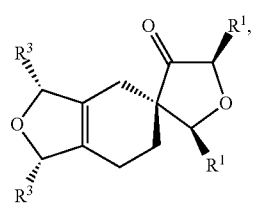
(XXX-a)

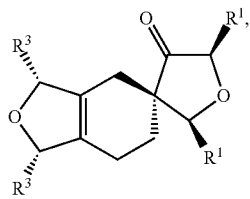
(XXX-b)

wherein $R^1$, and $R^3$ are as defined above.

This oxidative cleavage can be accomplished by a variety of methods known to the art including ozonolysis or dihydroxylation followed by oxidation (e.g. with periodate or lead tetraacetate).

In addition to their utility as therapeutic agents, ketones XXX-a and XXX-b are valuable intermediates for the synthesis of other compounds encompassed by the present invention. For example, ketones XXX-a and XXX-b can be converted to amines by reductive amination, to olefins by Wittig or other olefination reactions, to secondary alcohols by reduction, to oximes by condensation with hydroxylamines, to hydrazones by condensation with hydrazine, to tertiary alcohols by alkylation with organo magnesium or organo lithium compounds, or to ketals by reaction with diols. Alternatively, the ketone can be converted to an enolate and alkylation at an adjacent carbon can be affected.

In one such embodiment, the ketones XXX-a and XXX-b are reductively aminated (e.g. by reduction with $NaBH_3CN$ or $NaBH(OAc)_3$ in the presence of an amine $NH(R)_2$) to provide amines of formula XXXII-a, XXXII-b, XXXIII-a, or XXXIII-b or mixtures thereof:

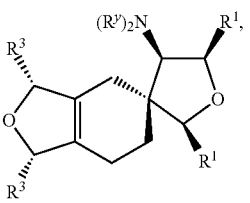
(XXXII-a)

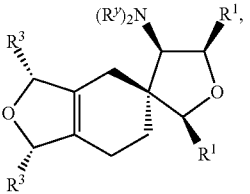
(XXXII-b)

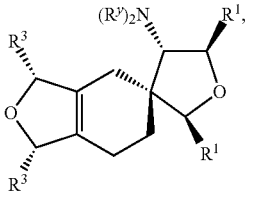
(XXXIII-a)

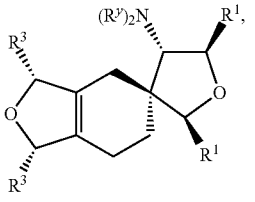
(XXXIII-b)

wherein $R^1$, $R^3$, and $R^y$ are as defined above.

It will be appreciated that the amines XXXIIa through XXXIIId can themselves be subjected to further reactions including, but not limited to: acylation, alkylation, quaternization, carbamoylation etc. to provide additional derivatives. These derivatives and the methods to produce them are specifically encompassed by the present invention.

In another embodiment, the ketones XXX-a and XXX-b are olefinated (e.g. by Wittig olefination with reagents of the form $Ph_3P=C(R^4)_2$) to yield compounds of formula XXV-a or XXV-b:

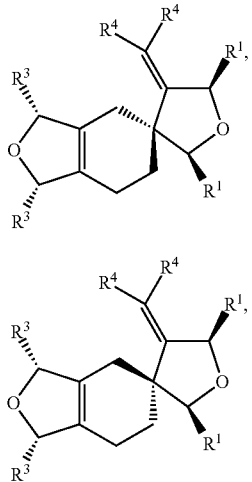

(XXV-a)

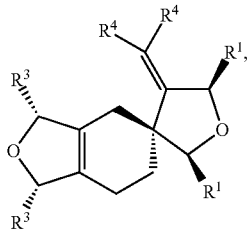

(XXV-b)

wherein $R^1$, $R^3$, and $R^4$ are as defined above, with the proviso that at least one $R^4$ is not —H.

It will be appreciated that the substituted alkenes XXVa and XXVb can be further manipulated (e.g. by hydrogenation, hydroboration, epoxidation, dihydroxylation etc.) and that the resulting derivatives and the methods to make them are specifically encompassed by the present invention.

In another embodiment, the ketones XXX-a and XXX-b are reacted with hydroxylamine derivatives $H_2N-OR^z$ to yield oxime derivatives of formula XXXI-a or XXXI-b:

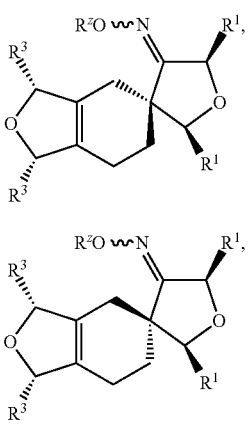

(XXXI-a)

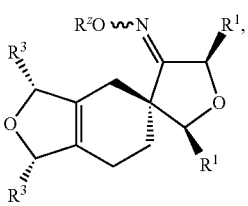

(XXXI-b)

wherein $R^1$, $R^3$, and $R^z$ are as defined above.

In another embodiment, the ketones XXX-a and/or XXX-b are reacted with an organometallic reagent (e.g. with $XMgR^m$, or $LiR^m$) to provide compounds of formula XXXIV-a through XXXIV-d or mixtures thereof:

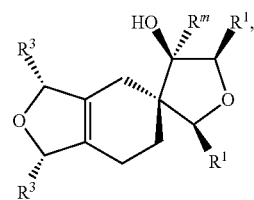

(XXXIV-a)

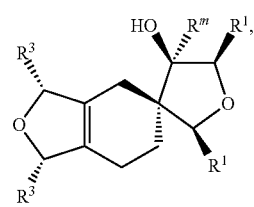

(XXXIV-b)

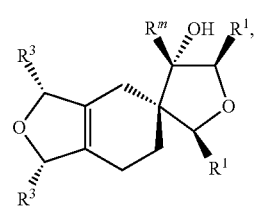

(XXXIV-c)

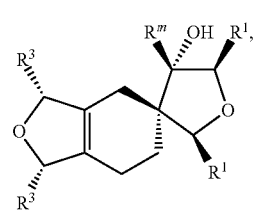

(XXXIV-d)

wherein $R^1$ and $R^3$ are as defined above, and $R^m$ is an optionally substituted $C_{1-20}$ aliphatic group or an optionally substituted $C_6$-$C_{14}$ aryl group or heteroaryl.

It will be appreciated that the alcohols XXXIV-a through XXXIV-d can be further manipulated using reactions well known in the art to provide additional derivatives, for example they may be alkylated, acylated, glycosylated, dehydrated, phosphorylated, or sulfonylated to afford additional derivatives. Multistep schemes such allylation followed by Claisen rearrangement of the corresponding allyl ethers are also contemplated. These compounds and mixtures thereof and the methods to make them are specifically encompassed by the present disclosure.

In another embodiment of the present disclosure, the ketones XXX-a and/or XXX-b are reduced to alcohols (e.g. with hydride reagents including, but not limited to $NaBH_4$, $LiBH_4$, $LiAlH_4$, L-selectride, D-selectride, diisobutylaluminium hydride or sodium bis(2-methoxyethoxy)aluminum hydride) to provide secondary alcohols of formula XXXV-a through XXXV-d or mixtures thereof:

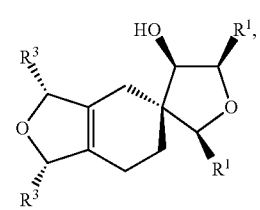

(XXXV-a)

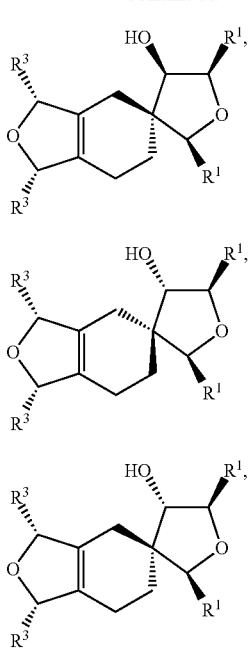

(XXXV-b)

(XXXV-c)

(XXXV-d)

wherein $R^1$ and $R^3$ are as defined above.

It will be appreciated that any of the alcohols XXXV-a through XXXV-d can be further manipulated using reactions well known in the art to provide additional derivatives, for example they may be alkylated, acylated, glycosylated, dehydrated, phosphorylated, or sulfonylated to afford additional derivatives. Multistep schemes such allylation followed by Claisen rearrangement of the corresponding allyl ethers are also contemplated. These derivatives and the methods to make them are specifically encompassed by the present invention.

In another embodiment of the present disclosure, the ketones XXX-a and/or XXX-b are converted to enolates (e.g. by treatment with LDA, or $R_2B$—Cl) and then subjected to Aldol reaction with carbonyl compounds of formula $R^dC(O)R^d$ to afford products of formula XXXVI-a or XXXVI-b or mixtures thereof:

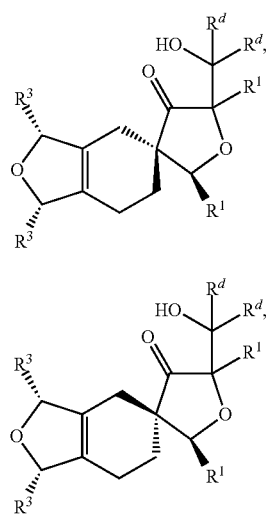

(XXXVI-a)

(XXXVI-b)

wherein $R^1$ and $R^3$ are as defined above, and each $R^d$ is independently —H, or an optionally substituted group selected $C_{1-20}$ aliphatic, $C_{1-20}$ heteroaliphatic, $C_{6-14}$ aryl, and 3- to 14-membered heterocyclic.

It will be appreciated that Aldol products XXXVI-a and XXXVI-b can be further manipulated using reactions well known in the art to provide additional derivatives, for example they may be alkylated, acylated, glycosylated, dehydrated, phosphorylated, or sulfonylated to afford additional derivatives. Multistep schemes such allylation followed by Claisen rearrangement of the corresponding allyl ethers are also contemplated. These derivatives and the methods to produce them are specifically encompassed by the present invention.

In certain embodiments, the alcohols XXXIV-a through XXXVI-b are glycosylated to provide compounds of where the hydrogen atom on the hydroxyl group is replaced by G, where G represents a carbohydrate moiety, including, but not limited to monosaccharide or polysaccharide moieties.

In certain embodiments, G is selected from the group consisting of: hexoses such as D-glucose, D-mannose, D-xylose, D-galactose, vancosamine, 3-desmethyl-vancosamine, 3-epi-vancosamine, 4-epi-vancosamine, acosamine, actinosamine, desosamine, daunosamine, 3-epi-daunosamine, ristosamine, N-methyl-D-glucamine, D-glucuronic acid, N-acetyl-D-glucosamine, N-acetyl-D-galactosamine, sialyic acid, iduroric acid, L-fucose, and the like; pentoses such as D-ribose or D-arabinose; ketoses such as D-ribulose or D-fructose; disaccharides such as 2-O-(α-L-vancosaminyl)-β-D-glucopyranose, 2-O-(3-desmethyl α L-vancosaminyl)-β-D-glucopyranose, sucrose, lactose, or maltose; derivatives such as acetals, amines, acylated, sulfated and phosphorylated sugars; oligosaccharides having from 2 to 10 saccharide units.

In still further embodiments of the present disclosure, the exocyclic alkene can be epoxidized to yield compounds of formulae XXVIII-a through XXVIII-d or mixtures of two or more of these. Epoxidation can be affected using reagents and methods well known in the art including but not limited to: reaction with peroxyacids such as meta-chloroperbenzoic acid (m-CPBA) and reaction with dioxiranes such as dimethyldioxirane (DMDO).

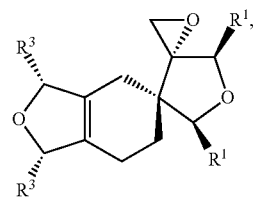

(XXVIII-a)

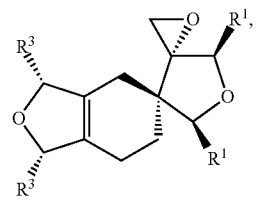

(XXVIII-b)

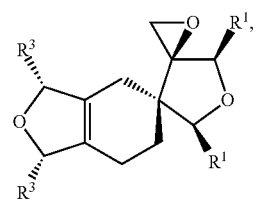

(XXVIII-c)

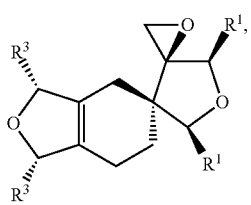
(XXVIII-d)

where R¹ and R³ are as defined above.

While epoxides XXVIII-a through XXVIII-d and mixtures thereof may have therapeutic utility, it will also be appreciated that they are useful synthetic intermediates that may be further derivatized. In one embodiment, epoxides XXVIII-a through XXVIII-d or mixtures thereof are derivatized by nucleophilic ring opening of the epoxide ring (e.g. by ring-opening with any suitable carbon-, oxygen-, nitrogen-, or sulfur-based nucleophile). These derivatives and methods are specifically encompassed by the present disclosure.

In other embodiments, the double bond between rings A and B of certain compounds of the present invention may be manipulated using reactions analogous to those described above. This may be done either prior to, or after manipulation of the exocyclic double bond of ring C.

In certain embodiments, the double bond between rings A and B is hydrogenated (e.g. using hydrogen gas and a Pd catalyst) to yield compounds of formulae XXXVII-a and/or XXXVII-b:

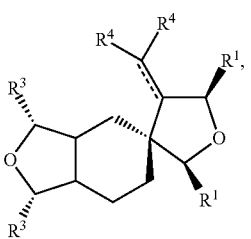
(XXXVII-a)

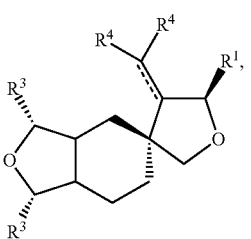
(XXXVII-b)

wherein, R¹, R³, and R⁴ are as defined above.

In other embodiments, the compounds of the present invention can be exhaustively hydrogenated (e.g. using hydrogen gas and a Pd catalyst) to reduce both alkene moieties yielding compounds of formulae XXXVIII-a or XXXVIII-b or mixtures thereof:

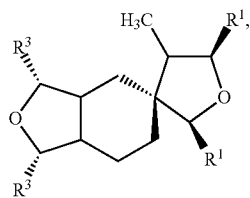
(XXXVIII-a)

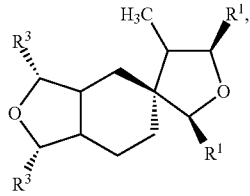
(XXXVIII-b)

wherein, R¹ and R³ are as defined above, and where one or both possible diastereomers are formed.

In other embodiments, the double bond between rings A and B is epoxidized to yield compounds of formulae XXXIX-a through XXXIX-d or mixtures of two or more of these. Epoxidation can be affected using reagents and methods well known in the art including but not limited to: reaction with peroxyacids such as meta-chloroperbenzoic acid (m-CPBA) and reaction with dioxiranes such as dimethyl-dioxirane (DMDO).

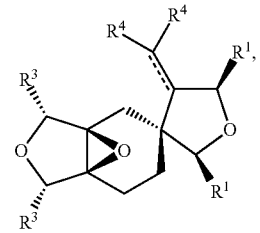
(XXXIX-a)

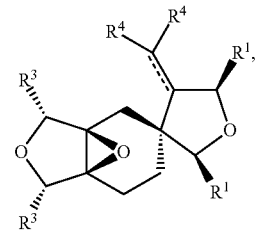
(XXXIX-b)

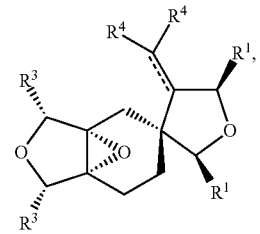
(XXXIX-a)

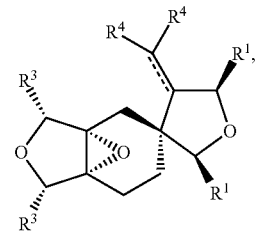
(XXXIX-b)

wherein, R¹, R³, and R⁴ are as defined above.

While epoxides XXXIX-a through XXXIX-d and mixtures thereof may have therapeutic utility, it will also be appreciated that they are useful synthetic intermediates that may be further derivatized. In one embodiment, epoxides XXXIX-a through XXXIX-d and mixtures thereof are derivatized by nucleophilic opening of the epoxide ring (e.g. by ring-opening with any suitable carbon-, oxygen-, nitrogen-, or sulfur-based nucleophile). These derivatives and methods are specifically encompassed by the present disclosure.

It is to be understood that the methods presented above to provide the synthetic semisynthetic derivatives described herein may require the selection of specific reagents and reaction conditions necessary to obtain reaction selectivity (e.g. reaction of one double bond in preference to another) or stereochemical selectivity (e.g. formation of one diastereomer in preference to another). Such experimental choices can be a matter of routine experimentation since the selectivity of a wide range of reagents and reaction conditions are known in the art.

It will also be understood, that while the manipulations are described above separately, they may be combined to yield compounds having two or more of the chemical modifications described. These compounds and the methods of making them are specifically encompassed by the present invention. Such schemes may obviously require thoughtful planning of the order of the reactions and use of appropriate functional group protection strategies. Such processes can be a matter of routine experimentation using the compounds, methods, and concepts described in the present disclosure.

In certain embodiments where the compounds of the invention have any of formulae XXI-a through XXXIX-b above, each $R^1$ is independently selected from the group consisting of $C_{1-20}$ aliphatic; $C_{1-20}$ heteroaliphatic having 1-4 heteroatoms; 6- to 14-membered aryl; 5- to 14-membered heteroaryl; and 3- to 7-membered heterocyclic.

In certain embodiments where the compounds of the invention have any of formulae XXI-a through XXXIX-b above, each $R^3$ is independently selected from the group consisting of $C_{1-20}$ aliphatic; $C_{1-20}$ heteroaliphatic having 1-4 heteroatoms; 6- to 14-membered aryl; 5- to 14-membered heteroaryl; and 3- to 7-membered heterocyclic.

In certain embodiments where the compounds of the invention have any of formulae XXI-a through XXXIX-b above, each $R^1$, and $R^3$ is independently selected from the group consisting of $C_{1-20}$ aliphatic; $C_{1-20}$ heteroaliphatic having 1-4 heteroatoms; 6- to 14-membered aryl; 5- to 14-membered heteroaryl; and 3- to 7-membered heterocyclic.

In certain embodiments where the compounds of the invention have any of formulae XXI-a through XXXIX-b above, each $R^1$ is independently is optionally substituted 6- to 14-membered aryl.

In certain embodiments where the compounds of the invention have any of formulae XXI-a through XXXIX-b above, each $R^3$ is independently is optionally substituted 6- to 14-membered aryl.

In certain embodiments where the compounds of the invention have any of formulae XXI-a through XXXIX-b above, each $R^1$ and $R^3$ independently has a structure:

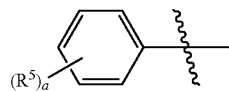

wherein:
$R^5$ at each occurrence is a moiety independently selected from the group consisting of: halogen; —CN; —$CO_2R^y$; —C(O)N($R^y$)$_2$; —C(S)O$R^y$; —C(S)N($R^y$)$_2$; —N($R^y$)$_2$; —N$R^y$C(O)$R^y$; —N$R^y$C(O)O$R^y$; —N$R^y$C(O)N($R^y$)$_2$; —N$R^y$C(S)$R^y$; —N$R^y$C(S)N($R^y$)$_2$; —N($R^y$)SO$_2R^y$; —NO$_2$; —NCO; —N$_3$; —O$R^z$; —OC(O)$R^y$; —OC(S)$R^y$; —OSO$_2R^y$; —OC(O)N($R^y$)$_2$; —OC(O)O$R^y$; —S(O)$_xR^y$; and —S(O)$_2$N($R^y$)$_2$; or an optionally substituted group selected from the group consisting of $C_{1-20}$ aliphatic; $C_{1-20}$ heteroaliphatic having 1-4 heteroatoms independently selected from the group consisting of nitrogen, oxygen, and sulfur; 6- to 14-membered aryl; 5- to 14-membered heteroaryl; and 3- to 7-membered heterocyclic, where two or more $R^5$ groups can be taken together with their intervening atoms to form an optionally substituted saturated, partially unsaturated, or aromatic 4- to 12-membered ring containing 0 to 4 heteroatoms, and a is 0, 1, 2, 3, 4, or 5.

In certain embodiments $R^5$ is —$OR^z$ at each occurrence.

In certain embodiments where the compounds of the invention have any of formulae XXI-a through XXXIX-b above, each $R^1$ and $R^3$ has a structure:

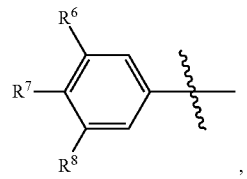

wherein $R^6$, $R^7$, and $R^8$ are each independently selected from the group consisting of: hydrogen, and —$OR^{z'}$, where $R^{z'}$ is as defined hereinabove.

In certain embodiments where the compounds of the invention have any of formulae XXI-a through XXXIX-b above, each $R^1$ and $R^3$ is independently selected from the group consisting of:

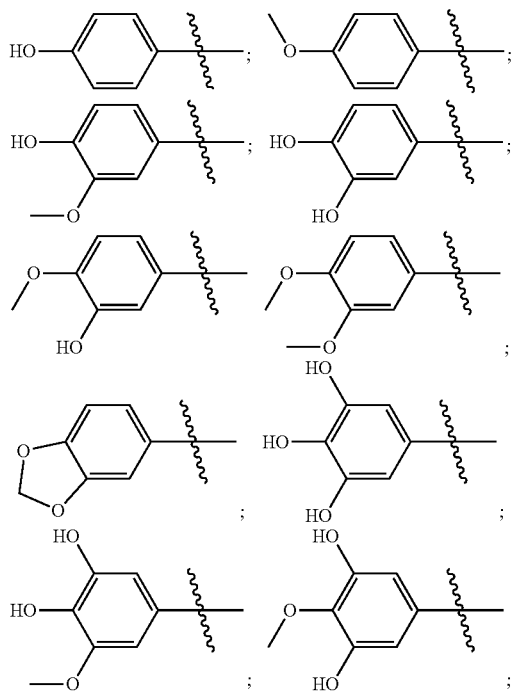

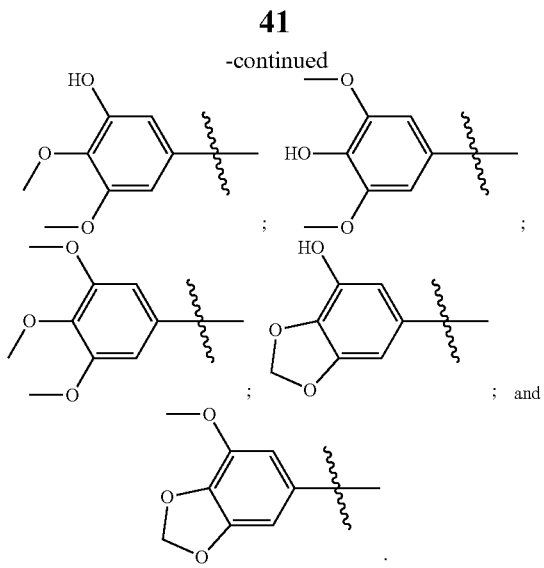

In certain embodiments where the compounds of the invention have any of formulae XXI-a through XXXIX-b above, each $R^1$ and $R^3$ has the structure:

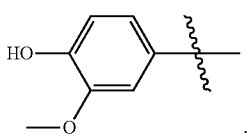

In many of the compounds described above, the substituents $R^1$ and $R^3$ comprise substituted phenyl rings. These rings present another attractive site for modification to produce additional molecules encompassed by the present invention. For example, the aryl rings of compounds I-a and I-b have the structure shown below and provide many possibilities for modification.

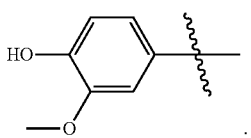 [SMILES: *c1ccc(O)c(OC)c1 ; "."]

In certain embodiments where the compounds of the invention have one or more $R^1$ or $R^3$ groups with the structure above, the phenolic hydroxyl group may be manipulated. Such hydroxyl group manipulations include, but are not limited to: alkylation, acylation, glycosylation, phosphorylation, or sulfonylation. Multistep reactions such as, for example, allylation followed by Claisen rearrangement of the corresponding allyl ethers are also encompassed. Representative examples of reactions that may be performed on any one or more $R^1$ or $R^3$ group are shown in Scheme 1.

Scheme 1

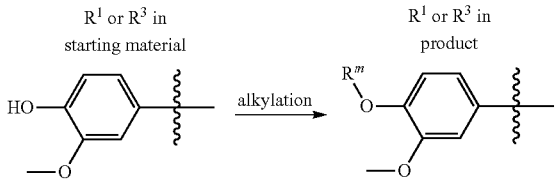

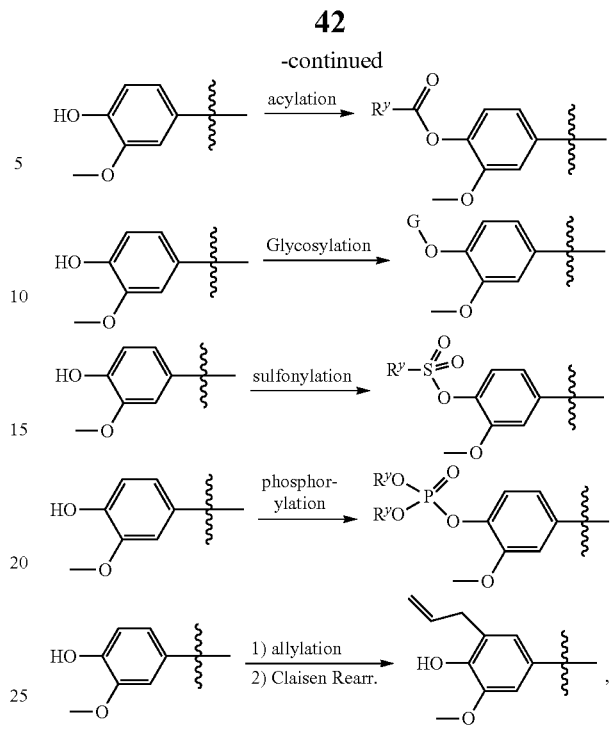

where
$R^m$, $R^y$ and G are as defined above.

In other embodiments, phenolic hydroxyl groups on any one or more of the $R^1$ or $R^3$ groups on compounds of the invention may be converted to derivatives suitable for aryl coupling reactions (e.g. Suzuki couplings, Stille couplings, Sonogashira couplings, Heck reactions, etc.). This may be accomplished, for example, by converting the phenolic hydroxyl group to a suitable leaving group such as a halide or triflate, or by converting the hydroxyl group to a boronate ester, as shown in Scheme 2.

Scheme 2

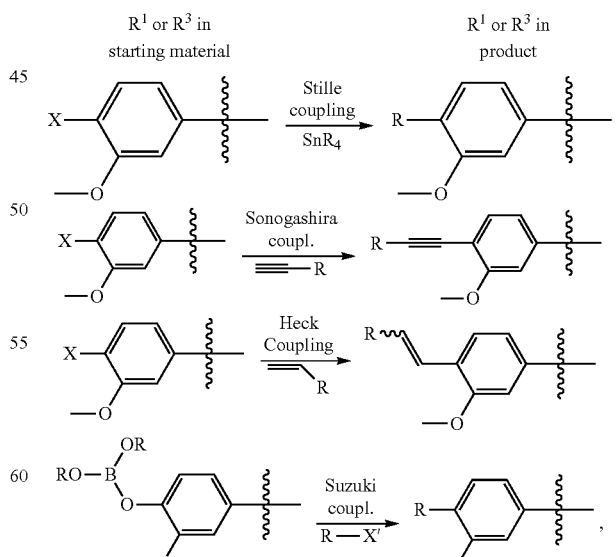

where X' is a halogen or sulfonate ester, and R is as defined above.

In another embodiment where the compounds of the invention have one or more $R^1$ or $R^3$ groups comprising phenyl rings bearing methoxy groups, one or more of the methoxy substituents may be demethylated (e.g. by reaction with $BBr_3$ or $(CH_3)_2BBr$). The resulting phenol may then be manipulated as described above, or the catecol may be converted to cyclic derivatives (e.g. by reaction with formaldehyde, phosgene, etc).

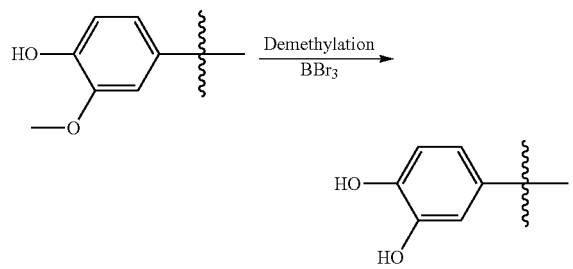

In certain embodiments, the phenolic hydroxyl group can first be protected (e.g. by silylation) followed by demethylation of the methoxyl substituent. This then allows any of the reactions described above for functionalization of the 4-hydroxy group to be applied to the 3-position of the aryl ring(s).

In still other embodiments, unsubstituted positions on aryl rings comprising one or more of the substituents $R^1$ or $R^3$ can be substituted. For example, the aryl rings can be subjected to conditions for electrophilic aromatic substitution, including, but not limited to nitration, sulfonation, halogenation, Friedel-Crafts acylation, or Friedel-Crafts alkylation.

Scheme 3

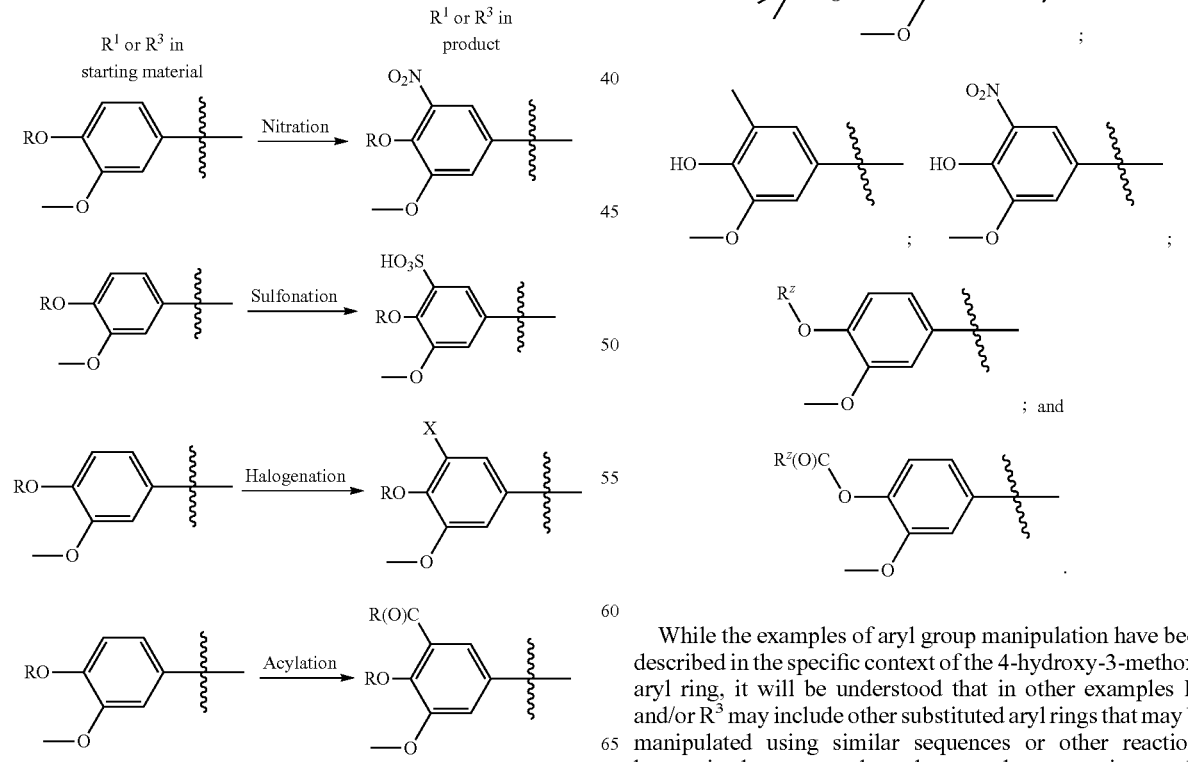

While it is not explicitly described in the reactions described hereinabove, it is to be understood that, to provide the derivatives described, it may be necessary in some cases to chemically protect (and subsequently de-protect) certain functional groups not involved in the transformations described. Such functional group protection schemes are well known to those skilled in the art of organic synthesis. Suitable functional group protection schemes are described, for example, in *Greene's Protective Groups in Organic Synthesis*, 4th Edition 2006 ISBN No. 978-0-471-69754-1, the entire content of which is hereby incorporated herein by reference.

In certain other embodiments, the present disclosure encompasses compounds of formulae V through XXXIII-b described hereinabove, where at least one $R^1$ or $R^3$ group is chosen from the group consisting of:

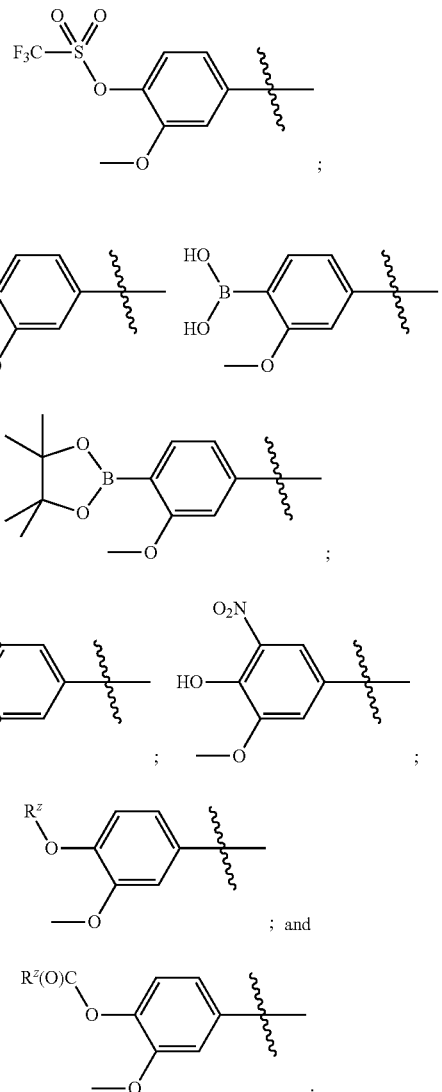

While the examples of aryl group manipulation have been described in the specific context of the 4-hydroxy-3-methoxy aryl ring, it will be understood that in other examples $R^1$ and/or $R^3$ may include other substituted aryl rings that may be manipulated using similar sequences or other reactions known in the art, or others that may be appropriate to the functionality present.

In certain embodiments, the present disclosure encompasses synthetic, or semi-synthetic derivatives derived from compounds I-a or I-b, or from mixtures of the two:

(I-a)

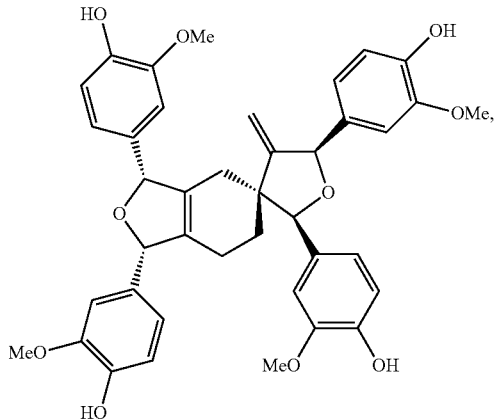

(I-b)

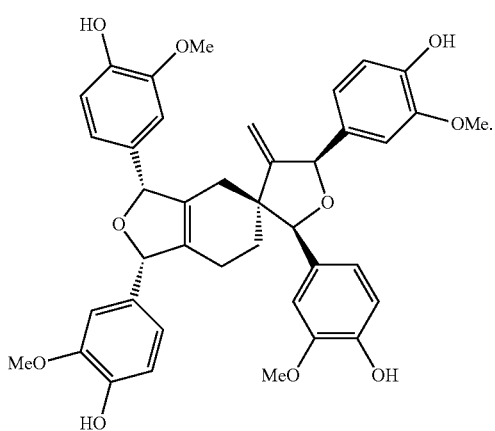

In other embodiments, the present disclosure encompasses methods of producing such derivatives from compounds I-a or I-b. Using the teachings and disclosures contained herein, it will be recognized by those having ordinary skill in the art of organic synthesis that compounds I-a and I-b present several sites suitable for chemical manipulation or derivatization to produce new derivatives. Such derivatives can have therapeutic advantages over parent compounds I-a and I-b. These advantages may include, but are not limited to: enhanced activity, bioavailability, selectivity or stability, or advantages related to lessened side effects, slower metabolism or altered tissue distributions. It is well known in the art how to measure these properties through appropriate in-vitro or in-vivo screening or through computational modeling. As such, it can be a matter of routine experimentation to identify the synthetic derivatives possessing the above described advantages.

In certain embodiments compounds of the present invention are the synthetic, or semi-synthetic derivatives resulting from chemical reactions of any of the compounds above. In certain embodiments, the invention encompasses synthetic or semi-synthetic derivatives of compounds I-a or I-b. Such reactions may include, but are not limited to: reduction, oxidation, alkylation, acylation, hydrogenation, halogenation, nitration, thermolysis, hydrolysis, epoxidation, dihydroxylation, hydroboration, amino hydroxylation, ozonolysis, aryl coupling reactions, solvolysis, cycloadditions, chemical rearrangements (including thermal or photochemical rearrangements), thermolysis, or photochemical reactions of compounds I-a or I-b, or mixtures of the two.

One class of semisynthetic derivatives encompassed by the

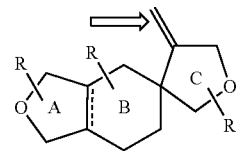

present invention result from manipulation of the exocyclic double bond on ring C of the core ring system of any of the compounds above. In certain embodiments, such reactions are performed using compounds I-a or I-b, or mixtures thereof as starting materials.

In certain embodiments, this double bond can be hydrogenated (e.g. using hydrogen gas and a Pd catalyst) to yield derivatives XL-a through XL-d:

(XL-a)

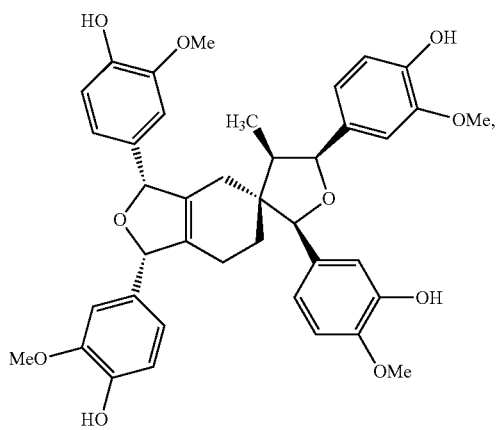

(XL-b)

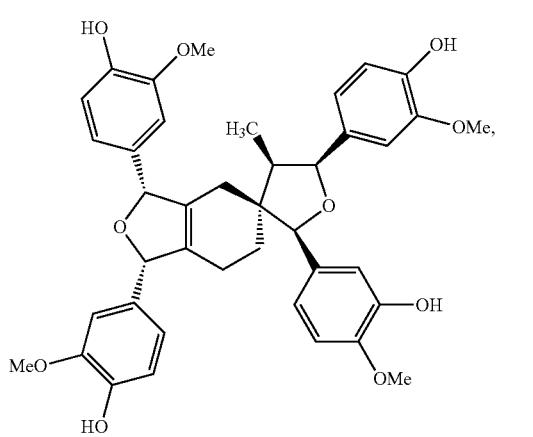

(XL-c)

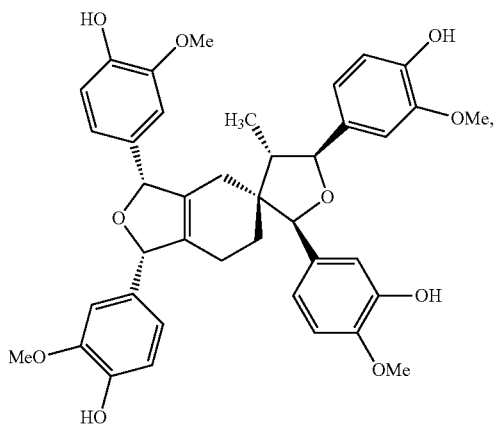

(XL-d)

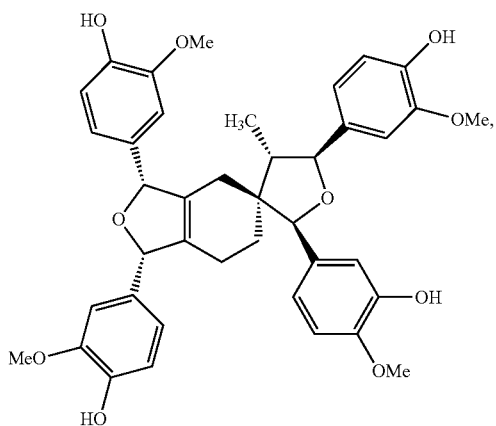

wherein, $R^1$, and $R^3$ are as defined above.

In an embodiment of a compound of Formula Ia to XL-d, $R^1$, $R^2$ and $R^3$ are independently selected form an optionally substituted moiety selected from $C_{1-20}$ aliphatic, $C_{1-20}$ heteroaliphatic having 1-4 heteroatoms independently selected from nitrogen, oxygen and sulfur; 6 to 14 membered aryl; 5 to 14 membered heteroaryl having 1-4 heteroatoms selected from nitrogen, oxygen and sulfur; and 4- to 7 membered heterocyclic having 1-3 heteroatoms selected from nitrogen, oxygen and sulfur.

In another embodiment of compounds of Formula I to XL-d, $R^1$ and $R^3$ are independently selected from an optionally substituted moiety selected from $C_{1-20}$ aliphatic; $C_{1-20}$ heteroaliphatic having 1-4 heteroatoms independently selected from nitrogen, oxygen and sulfur 6 to 14 membered aryl; 5 to 14 membered heteroaryl having 1-4 heteroatoms selected from nitrogen, oxygen and sulfur and 4 to 7-membered heterocyclic having 1-3 heteroatoms selected from nitrogen, oxygen and sulfur.

In another embodiment, $R^1$ and $R^3$ are independently optionally substituted 6 to 14 membered aryl.

In another embodiment of a compound of Formula I-XLd, $R^1$ and $R^3$ are independently optionally substituted phenyl.

In another embodiment, $R^1$ and $R^3$ are independently

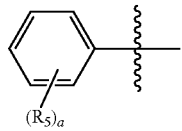

where $R^5$ and a are as defined above.

As will be appreciated by those having ordinary skill in the art of organic synthesis, appropriate conditions will be required to selectively reduce the exocyclic double bond while leaving the tetrasubstituted double bond between rings A and B unaffected, the selection of appropriate reagents and reaction conditions to affect the desired selectivity can be a matter of routine experimentation. Similarly, the stereochemistry of the resulting methyl group can be controlled by choosing appropriate catalysts and reaction conditions for the hydrogenation. Suitable techniques to achieve these selectivities may be found, for example, in: *Catalytic Hydrogenation-Techniques and Applications in Organic Synthesis* by R. L. Augustine, the entire content of which is hereby incorporated herein by reference. Alternatively, these compounds can be generated by alternate reaction sequences such as halogenation followed by hydrogenolysis.

In other embodiments, the exocyclic double bond can be oxidized.

In certain embodiments, the double bond is di-hydroxylated (e.g. with osmium tetroxide in the presence of an organic oxidant) to yield compounds of formulae XLI-a through XLI-d or mixtures of two or more of these:

(XLI-a)

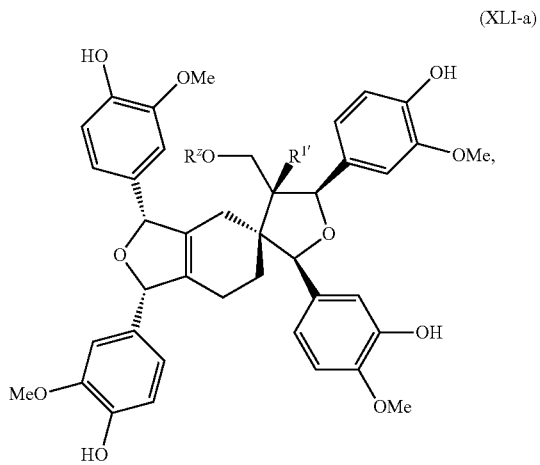

(XLI-b)

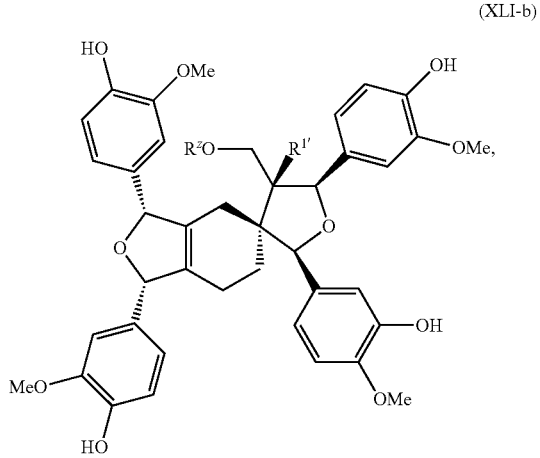

(XLI-c)
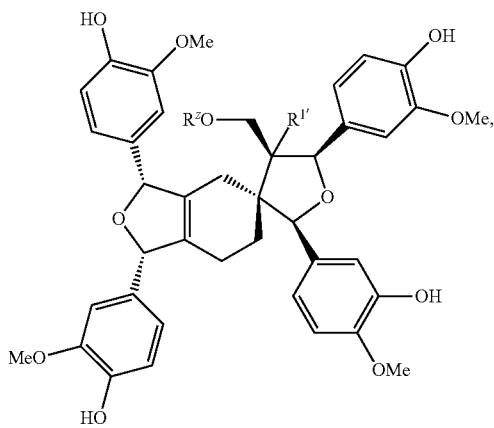

(XLII-a)
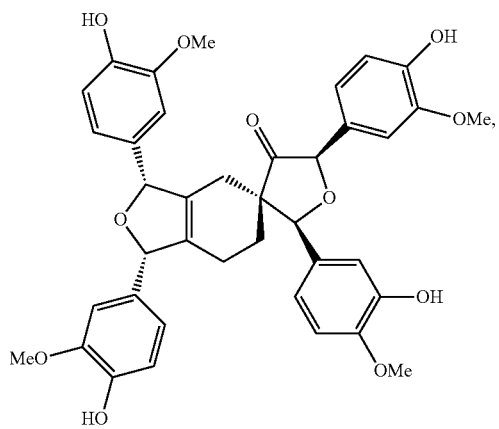

(XLI-d)
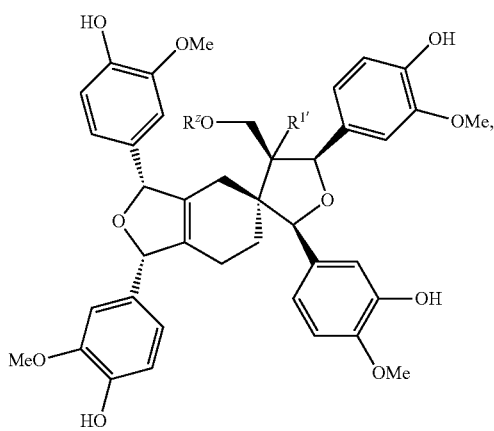

(XLII-b)
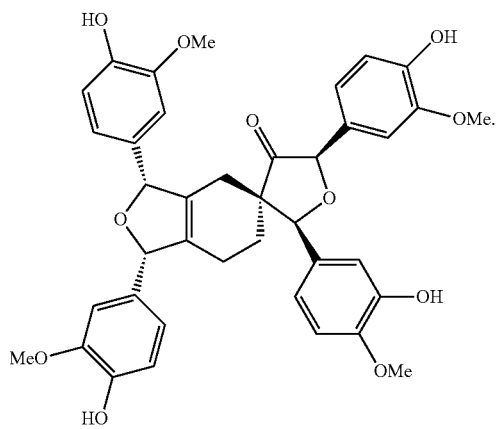

where $R^z$ is H, $R^{1'}$ is OH, and $R^1$ and $R^3$ are as defined above.

It will be appreciated that the alcohols XLI-a through XLI-d can, with appropriate protection of the phenolic hydroxyl groups, be further manipulated using reactions well known in the art to provide further derivatives, for example they may be alkylated, acylated, glycosylated, dehydrated, phosphorylated, or sulfonylated to afford additional derivatives. Multistep schemes such allylation followed by Claisen rearrangement of the corresponding allyl ethers are also contemplated. These compounds and mixtures thereof and the methods to make them are specifically encompassed by the present disclosure.

Alternatively, compounds of the present invention can be obtained by oxidative cleavage of the exocyclic double bond of compounds I-a or I-b to yield ketones having formulae XLII-a or XLII-b:

This oxidative cleavage can be accomplished by a variety of methods known to the art including ozonolysis, or dihydroxylation followed by oxidation (e.g. with periodate or lead tetraacetate).

Ketones XLII-a and XLII-b are valuable intermediates for the synthesis of other compounds encompassed by the present invention. For example, ketones XLII-a and XLII-b can be converted to amines by reductive amination, to olefins by Wittig or other olefination reactions, to secondary alcohols by reduction, to oximes by condensation with hydroxylamines, to hydrazones by condensation with hydrazine, or to tertiary alcohols by alkylation with organo magnesium or organo lithium compounds. Alternatively, the ketone can be converted to an enolate and alkylation at an adjacent carbon can be affected.

In one embodiment, the ketones XLII-a and XLII-b are reductively aminated (e.g. by reduction with $NaBH_3CN$ or $NaBH(OAc)_3$ in the presence of an amine $NH(R^y)_2$) to provide amines of formula XXXII-a, XXXIII-a, or XXXIII-b or mixtures thereof:

(XLIII-a)

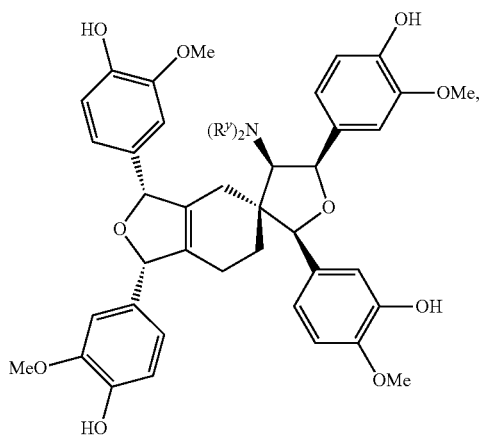

(XLIII-b)

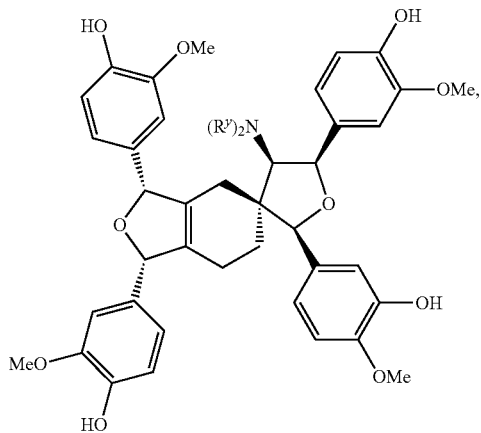

(XLIII-c)

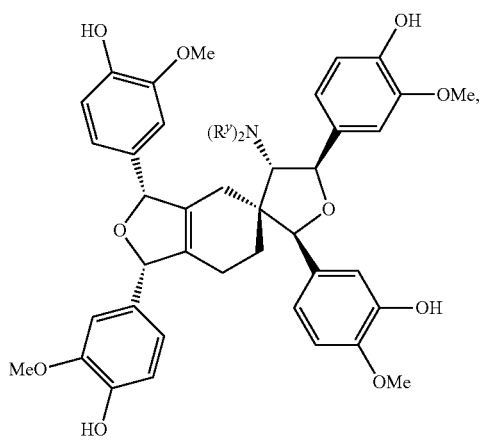

-continued (XLIII-d)

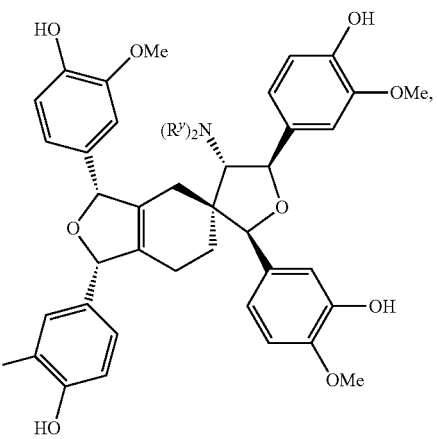

wherein $R^y$ is as defined above.

It will be appreciated that the amines XLIIIa through XLIIId can be subjected to further reactions including, but not limited to: acylation, alkylation, quaternization, carbamoylation etc. to provide additional derivatives. These derivatives and the methods to produce them are specifically encompassed by the present invention.

In another embodiment, the ketones XLII-a and XLII-b can be olefinated (e.g. by Wittig olefination with reagents of the form $Ph_3P\!\!=\!\!C(R^4)_2$) to yield compounds of formula XLIV-a or XLIV-b:

(XLIV-a)

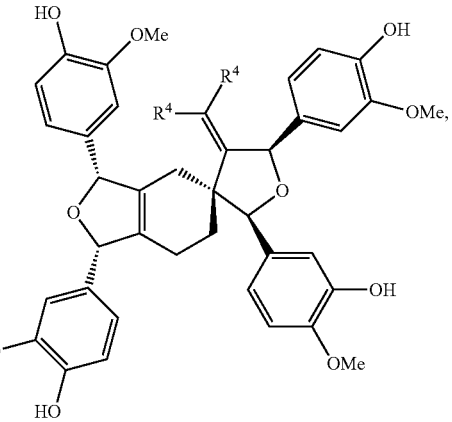

(XLIV-b)

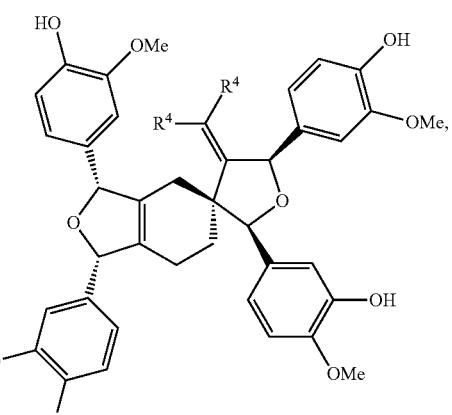

wherein $R^4$ is as defined above, with the proviso that at least one $R^4$ is not —H.

It will be appreciated that the substituted alkenes XLIVa and XLIVb can be further manipulated (e.g. by hydrogenation, hydroboration, epoxidation, dihydroxylation etc.) and that the resulting derivatives and the methods to make them are specifically encompassed by the present invention.

In another embodiment, the ketones XLII-a and XLII-b are reacted with hydroxylamine derivatives $H_2N$—$OR^z$ to yield oxime derivatives of formula XLV-a or XLV-b:

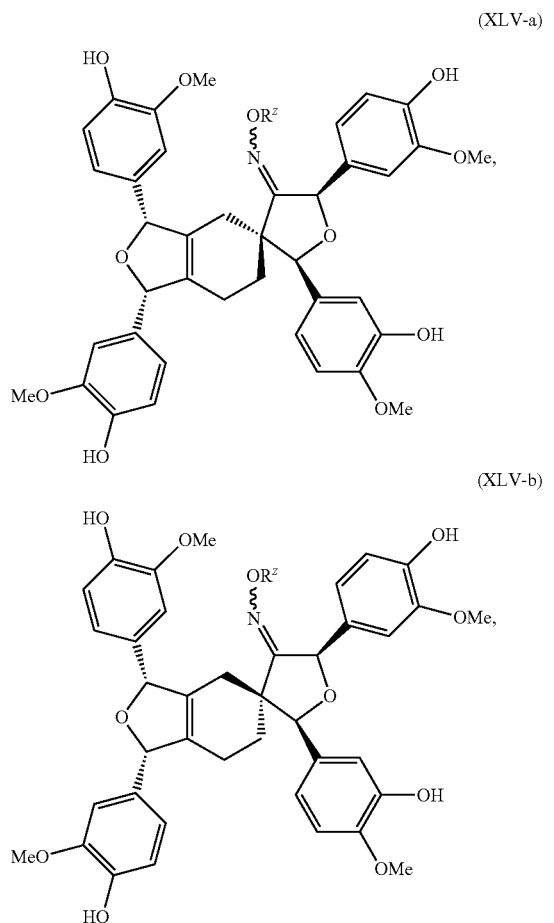

wherein IV is as defined above.

In another embodiment, the ketones XLII-a and/or XLII-b are reacted with an organometallic reagent (e.g. with $XMgR^m$, or $LiR^m$) to provide compounds of formula XXXIV-a through XXXIV-d or mixtures thereof:

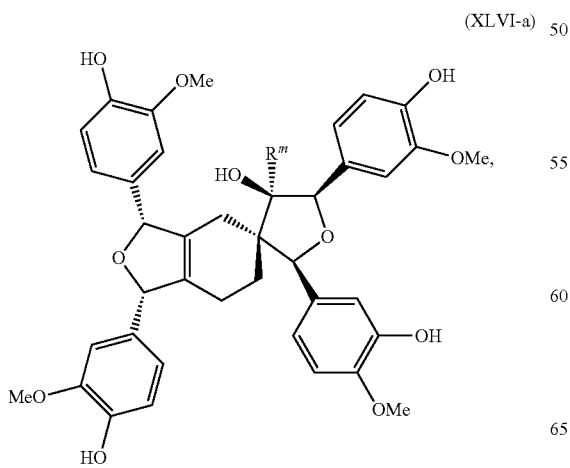

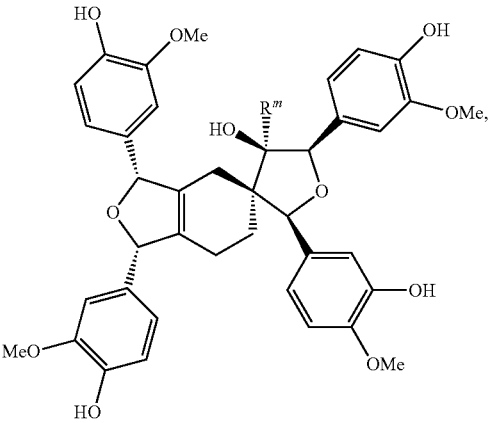

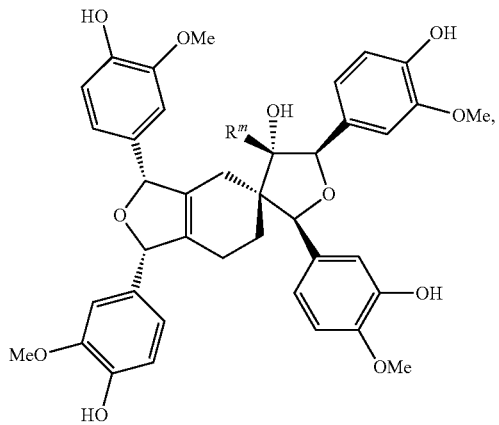

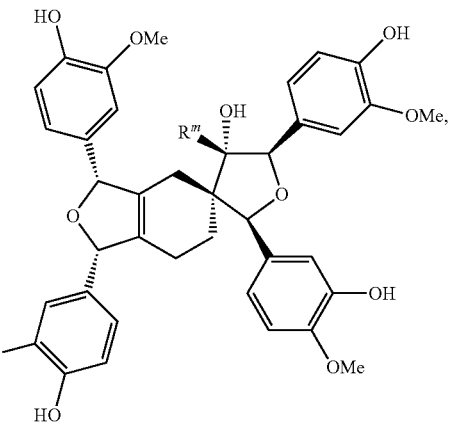

wherein $R^m$ is an optionally substituted $C_1$-$C_{20}$ aliphatic group or an optionally substituted $C_6$-$C_{14}$ aryl group.

It will be appreciated that the alcohols XLVI-a through XLVI-d can, with appropriate protection of the phenolic hydroxyl groups, be further manipulated using reactions well known in the art to provide further derivatives, for example they may be alkylated, acylated, glycosylated, dehydrated, phosphorylated, or sulfonylated to afford additional derivatives. Multistep schemes such allylation followed by Claisen rearrangement of the corresponding allyl ethers are also contemplated. These compounds and mixtures thereof and the methods to make them are specifically encompassed by the present disclosure.

In another embodiment of the present disclosure, the ketones XLII-a and/or XLII-b are reduced to alcohols (e.g. with hydride reagents including, but not limited to NaBH$_4$, LiBH$_4$, LiAlH$_4$, L-selectride, D-selectride, diisobutylaluminium hydride or sodium bis(2-methoxyethoxy)aluminum hydride) to provide secondary alcohols of formula XLVII-a through XLVII-d or mixtures thereof:

(XLVII-a)

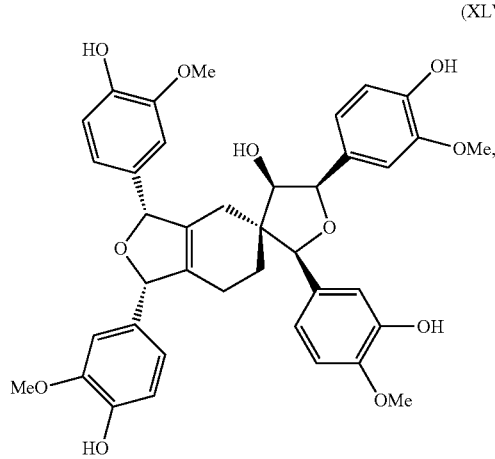

(XLVII-b)

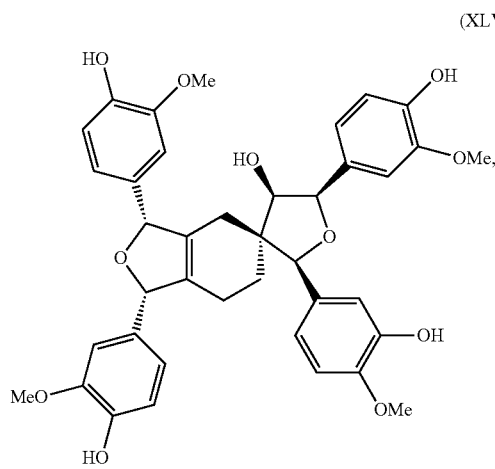

(XLVII-c)

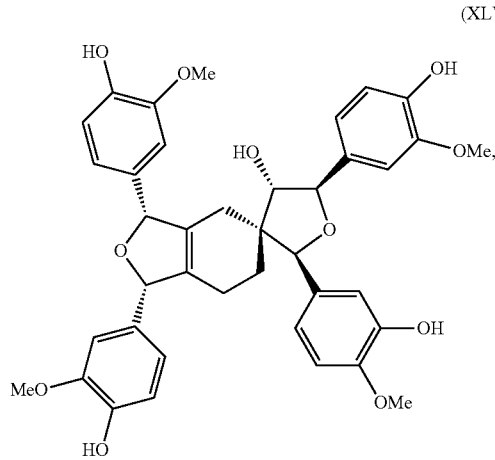

(XLVII-d)

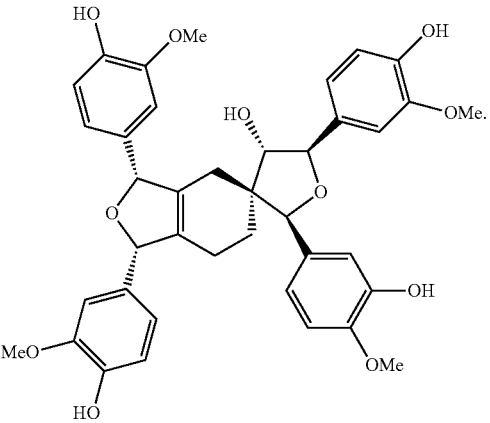

It will be appreciated that any of the alcohols XLVII-a through XLVII-d can, with appropriate protection of the phenolic hydroxyl groups, be further manipulated using reactions well known in the art to provide additional derivatives, for example they may be alkylated, acylated, glycosylated, dehydrated, phosphorylated, or sulfonylated to afford additional derivatives. Multistep schemes such allylation followed by Claisen rearrangement of the corresponding allyl ethers are also contemplated. These derivatives and the methods to make them are specifically encompassed by the present invention.

In another embodiment of the present disclosure, the ketones XLII-a and/or XLII-b are converted to enolates (e.g. by treatment with LDA, or R$_2$B—Cl) and then subjected to Aldol reaction with carbonyl compounds of formula R$^d$C(O)R$^d$ to afford products of formula XLVIII-a or XLVIII-b or mixtures thereof:

(XLVIII-a)

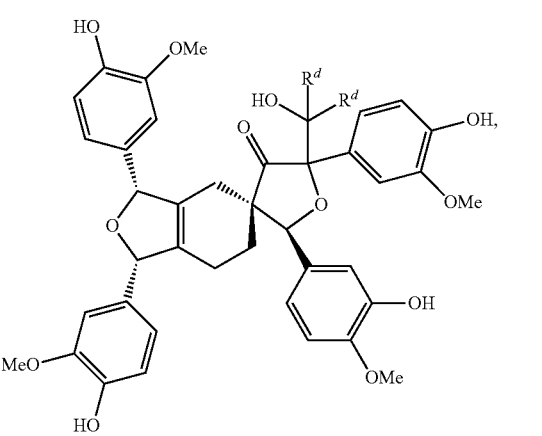

-continued (XLVIII-b)

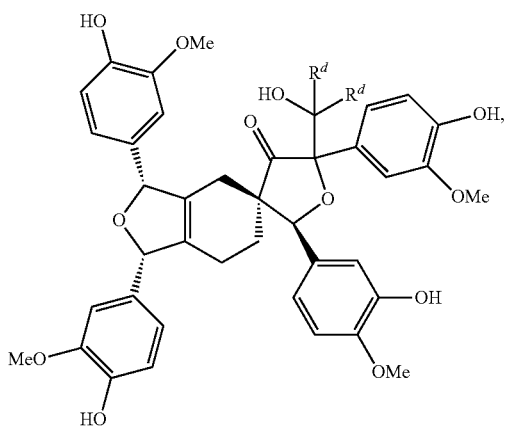

wherein each Rd is independently —H, or an optionally substituted group selected $C_{1-20}$ aliphatic, $C_{1-20}$ heteroaliphatic, $C_{6-14}$ aryl, and 3- to 14-membered heterocyclic.

It will be appreciated that Aldol products XLVIII-a and XLVIII-b can be further manipulated using reactions well known in the art to provide further derivatives. For example, with appropriate protection of the phenolic hydroxyl groups, they may be alkylated, acylated, glycosylated, dehydrated, phosphorylated, or sulfonylated to afford additional derivatives. Multistep schemes such allylation followed by Claisen rearrangement of the corresponding allyl ethers are also contemplated. These derivatives and the methods to produce them are specifically encompassed by the present invention.

In still further embodiments of the present disclosure, the exocyclic alkene of compounds I-a or I-b can be epoxidized to yield compounds of formulae XLIX-a through XLIX-d or mixtures of two or more of these. Epoxidation can be affected using reagents and methods well known in the art including but not limited to: reaction with peroxyacids such as meta-chloroperbenzoic acid (m-CPBA) and reaction with dioxiranes such as dimethyldioxirane (DMDO).

(XLIX-a)

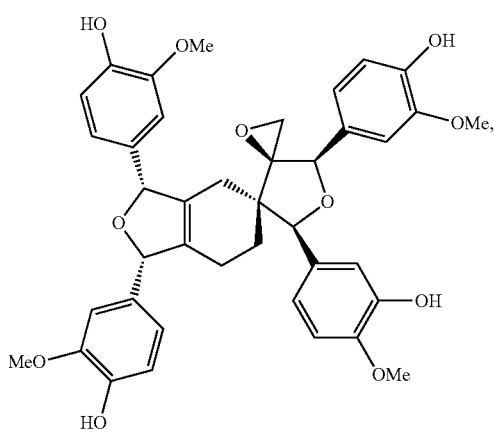

-continued (XLIX-b)

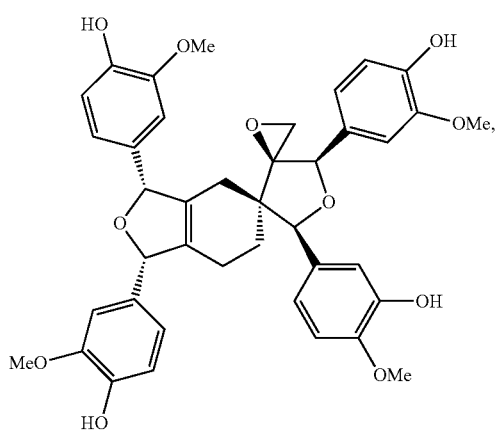

(XLIX-c)

(XLIX-d)

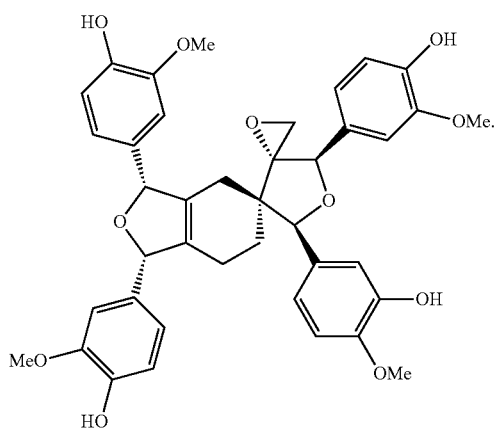

While epoxides XLIX-a through XLIX-d and mixtures thereof may have therapeutic utility, it will also be appreciated that they are useful synthetic intermediates that may be further derivatized. In one embodiment, epoxides XLIX-a through XLIX-d or mixtures thereof are derivatized by nucleophilic ring opening of the epoxide ring (e.g. by ring-opening with any suitable carbon-, oxygen-, nitrogen-, or sulfur-based nucleophile). These derivatives and methods are specifically encompassed by the present disclosure.

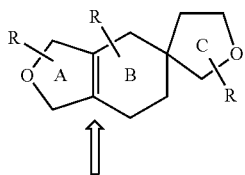

In other embodiments, the double bond between rings A and B of compounds I-a or I-b invention may be manipulated using reactions analogous to those described above. This may be done either prior to, or after manipulation of the exocyclic double bond of ring C.

In certain embodiments, the double bond between rings A and B of compounds I-a or I-b is hydrogenated (e.g. using hydrogen gas and a Pd catalyst) to yield compounds of formulae L-a and/or L-b:

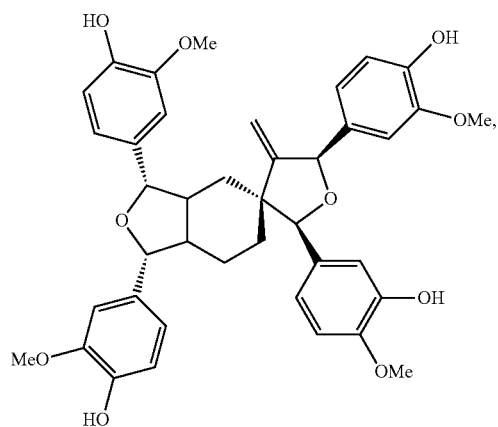

(L-a)

(L-b)

In other embodiments, compounds I-a and/or I-b can be exhaustively hydrogenated (e.g. using hydrogen gas and a Pd catalyst) to reduce both double bonds yielding compounds of formulae LI-a or LI-b or mixtures thereof:

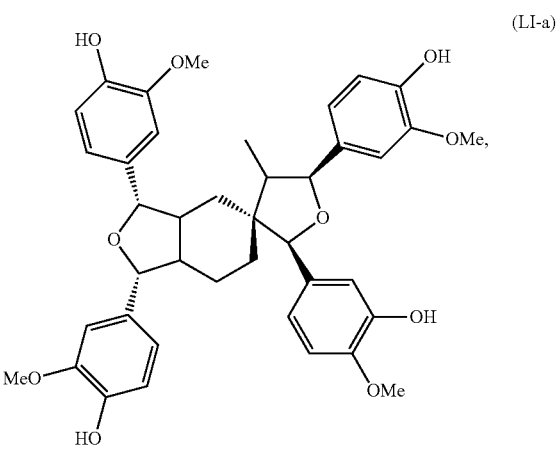

(LI-a)

(LI-b)

In other embodiments, the double bond between rings A and B of compounds I-a and/or I-b is epoxidized to yield compounds of formulae LII-a through LII-d or mixtures of two or more of these. Epoxidation can be affected using reagents and methods well known in the art including but not limited to: reaction with peroxyacids such as meta-chloroperbenzoic acid (m-CPBA) and reaction with dioxiranes such as dimethyldioxirane (DMDO).

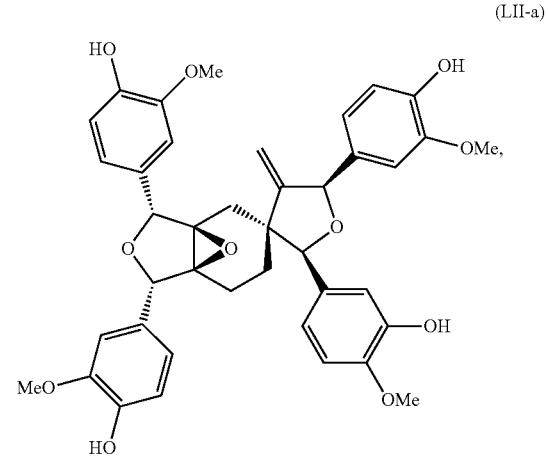

(LII-a)

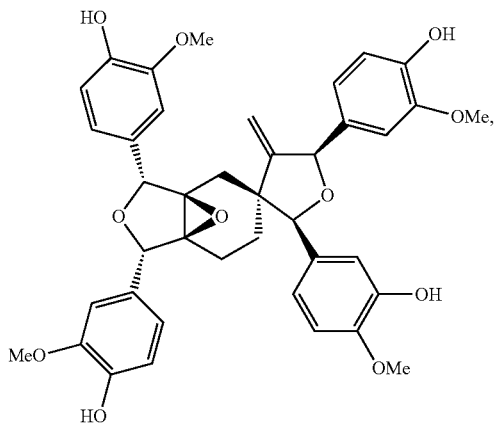

(LII-b)

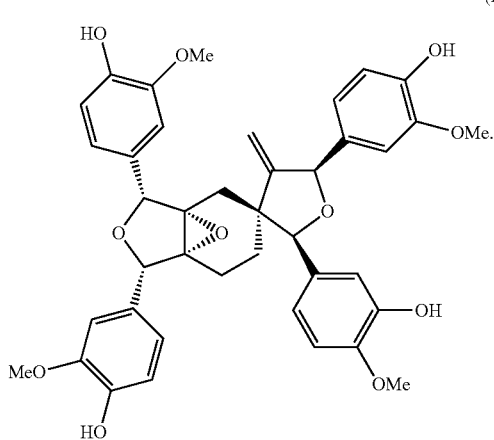

(LII-c)

(LII-d)

While epoxides LII-a through LII-d and mixtures thereof may have therapeutic utility, it will also be appreciated that they are useful synthetic intermediates that may be further derivatized. In one embodiment, epoxides LII-a through LII-d and mixtures thereof are derivatized by nucleophilic ring opening of the epoxide ring (e.g. by ring-opening with any suitable carbon-, oxygen-, nitrogen-, or sulfur-based nucleophile). These derivatives and methods are specifically encompassed by the present disclosure.

It is to be understood that the methods presented above to provide the synthetic semisynthetic derivatives of compounds I-a and I-b as described above may require the selection of specific reagents and reaction conditions necessary to obtain reaction selectivity (e.g. reaction of one double bond in preference to another) or stereochemical selectivity (e.g. formation of one diastereomer in preference to another). Such selections can be a matter of routine experimentation since the selectivity of a wide range of reagents and reaction conditions are known in the art.

In many of the compounds described above, the substituents $R^1$ and $R^3$ comprise substituted phenyl rings—these rings present another attractive site for modification to produce additional molecules encompassed by the present invention. For example, the four aryl rings of compounds I-a and I-b have the structure shown below and provide many opportunities for modification.

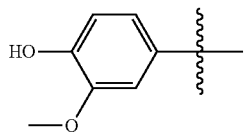 [SMILES: *c1ccc(O)c(OC)c1]

In certain embodiments where the compounds of the invention have one or more $R^1$ or $R^3$ groups with the structure above, the phenolic hydroxyl group may be manipulated. Such hydroxyl group manipulations include, but are not limited to: alkylation, acylation, glycosylation, phosphorylation, or sulfonylation. Multistep reactions such as, for example, allylation followed by Claisen rearrangement of the corresponding allyl ethers are also encompassed. Representative examples are shown in Scheme 1.

Scheme 1

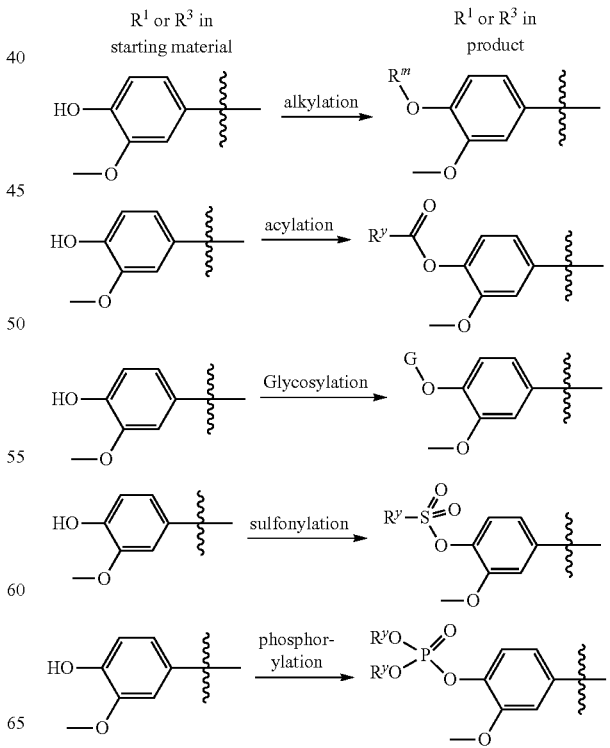

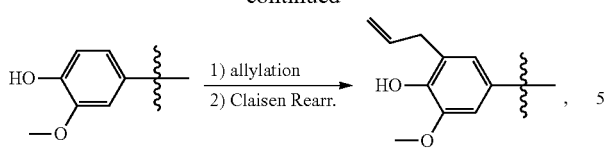

where

R$^m$, R$^y$ and G are as defined above.

In other embodiments, phenolic hydroxyl groups on any one or more of the R$^1$ or R$^3$ groups on compounds of the invention may be converted to derivatives suitable for aryl coupling reactions (e.g. Suzuki couplings, Stifle couplings, Sonogashira couplings, Heck reactions, etc.). This may be accomplished, for example, by converting the phenolic hydroxyl group to a suitable leaving group such as a halide or triflate, or by converting the hydroxyl group to a boronate ester, as shown in Scheme 2.

Scheme 2

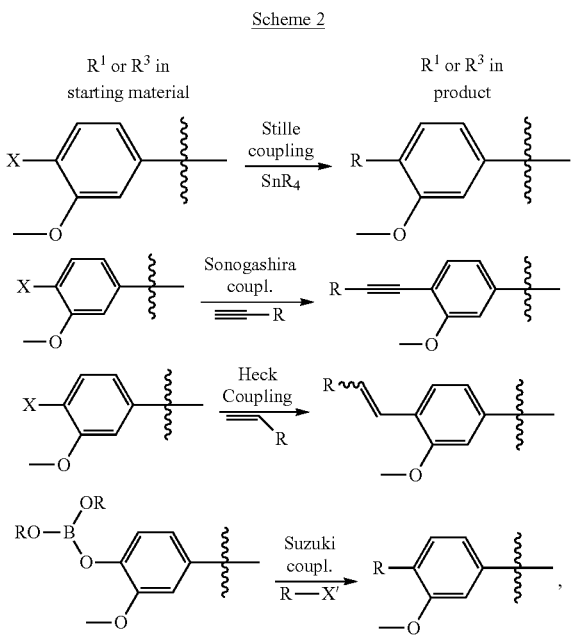

where X' is a halogen or sulfonate ester such as tosylate, mesylate or brosylate, and the like.

In another embodiment where the compounds of the invention have one or more R$^1$ or R$^3$ groups comprising phenyl rings bearing methoxy groups, one or more of the methoxy substituents may be demethylated (e.g. by reaction with BBr$_3$ or (CH$_3$)$_2$BBr). The resulting phenolic hydroxyl group may then be manipulated as described above, or the catecol may be converted to cyclic derivatives (e.g. by reaction with formaldehyde, phosgene, etc).

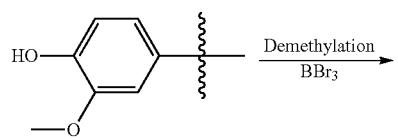

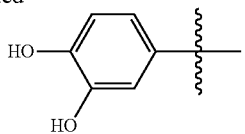

In still other embodiments, unsubstituted positions on aryl rings comprising one or more of the substituents R$^1$ or R$^3$ can be substituted. For example, the aryl rings can be subjected to conditions for electrophilic aromatic substitution, including, but not limited to nitration, sulfonation, halogenation, Friedel-Crafts acylation, or Friedel-Crafts alkylation.

Scheme 3

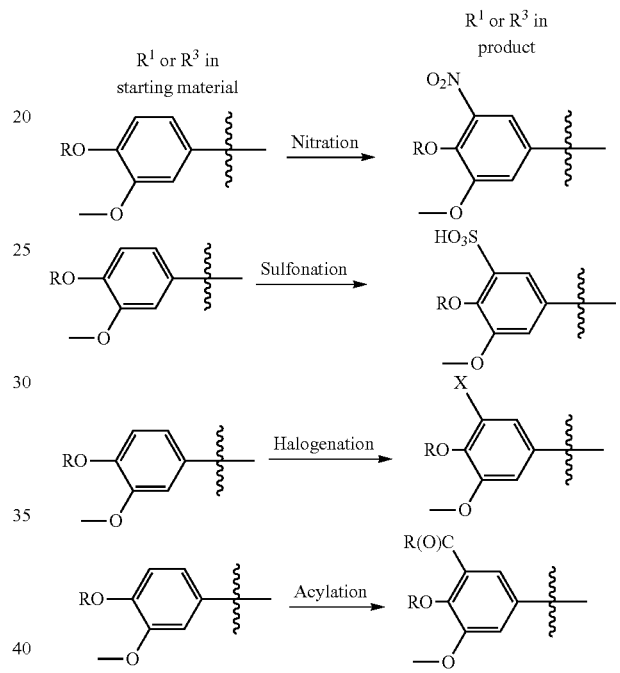

While it is not explicitly described in the reactions described hereinabove, it is to be understood that, to provide the derivatives described, it may be necessary in some cases to chemically protect (and subsequently de-protect) certain functional groups not involved in the transformations described. Such functional group protection schemes are well known to those skilled in the art of organic synthesis. Suitable functional group protection schemes are described, for example, in *Greene's Protective Groups in Organic Synthesis*, 4th Edition 2006 ISBN No. 978-0-471-69754-1, the entire content of which is hereby incorporated herein by reference.

In certain other embodiments, the present disclosure encompasses compounds of formulae V through XXXIII-b described hereinabove, where at least one R$^1$ or R$^3$ group is chosen from the group consisting of:

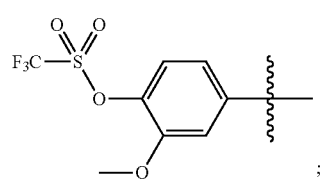

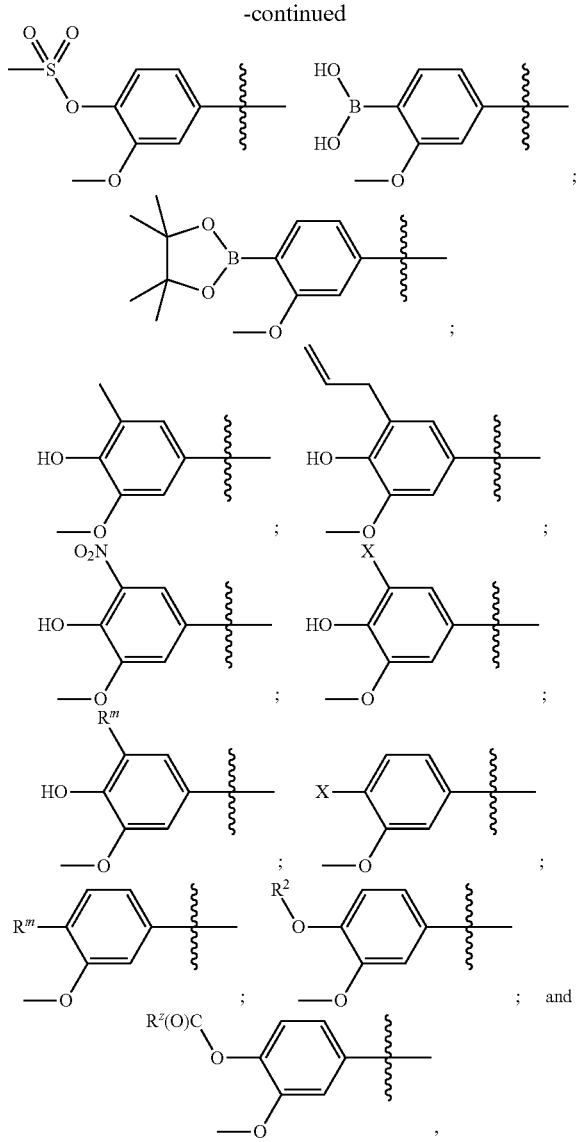

where $R^m$, $R^y$, and $R^z$, are as described above and X is any halogen.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate and the like. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like.

Using techniques known to the skilled artisan, the compositions described herein may be made substantially pure. By "substantially pure", it is meant that the compound or pharmaceutically acceptable salt has been purified to be substantially free of impurities. The compound and salt is purified by techniques known to the skilled artisan, such as by recrystallization, extraction, chromatography, including but not limited to, gas chromatography, column chromatography, HPLC, and the like. In an embodiment, the compound or salt is at least 80% by weight pure, and in another embodiment it is at least 85% pure by weight. In another embodiment, it is at least 90% pure by weight, and in a still another embodiment, it is at least about 95% pure and in still another embodiment, it is at least about 99% pure.

2) Therapeutic Methods of the Invention

In another embodiment, the present disclosure encompasses methods of treating or preventing disease by administration of any of the novel compounds described hereinabove, or any pharmaceutically acceptable salt thereof.

In certain embodiments, the present disclosure encompasses methods for the treatment of abnormal cell growth in a mammal.

More specifically, in certain embodiments, this invention relates to a method for the treatment of abnormal cell growth in a mammal, including a human, comprising administering to said mammal an amount of a compound of the formulae I through LII-d, as defined above (or a pharmaceutically acceptable salt thereof), that is effective in treating abnormal cell growth. In certain embodiments, the compound administered is compound I-a or I-b, or a mixture of I-a and I-b.

In other embodiments, the methods encompass treating a mammal, including a human, having a hyperproliferative disorder with a compound of formulae I through LII-d, as defined above (or a pharmaceutically acceptable salt thereof), that is effective in treating hyperproliferative disorders. In certain embodiments, the mammal is treated with compound I-a or I-b, or a mixture of I-a and I-b.

In certain embodiments of these methods, the abnormal cell growth is cancer, including, but not limited to, breast cancer, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of two or more of the foregoing cancers.

In one embodiment of this method, the abnormal cell growth is breast cancer. In certain embodiments of this method, the breast cancer includes but is not limited to adenocarcinoma, lobular (small cell) carcinoma, intraductal carcinoma, medullary breast cancer, mucinous breast cancer, tubular breast cancer, papillary breast cancer, Paget's disease, and inflammatory breast cancer.

In another embodiment of this method, the abnormal cell growth is pancreatic cancer. In certain embodiments of this method, the pancreatic cancer includes, but is not limited to, insulinoma, gastrinoma, glucagonoma, vipoma, somatostatin-secreting tumor, and carcinoid or islet cell tumor.

In certain embodiments the methods comprise administering to a mammal an amount any one or more of the compounds of formulae I through LII-d that is effective in treating a solid tumor. In certain embodiments, the compound administered is compound I-a or I-b, or a mixture of I-a and I-b. In one preferred embodiment the solid tumor is breast, pancreatic, lung, colon, brain, prostate, stomach, ovarian, skin (melanoma), endocrine, uterine, testicular, and bladder cancer.

In another embodiment of the methods, the abnormal cell growth is a benign proliferative disease, including, but not limited to, psoriasis, benign prostatic hypertrophy or restenosis. In a further embodiment, the invention provides methods for preventing, managing, treating, or ameliorating a non-cancerous disorder associated with cellular hyperproliferation (e.g., Behcet's Syndrome, sarcoidosis, keloids, pulmonary fibrosis, macular degeneration or renal fibrosis) or one or more symptoms thereof, the methods comprising administering to a subject in need thereof a prophylactically or therapeutically effective amount of one or more compounds of formulae I through LII-d. In certain embodiments, the compound administered is compound I-a or I-b, or a mixture of I-a and I-b.

This invention also relates to a method for the treatment of abnormal cell growth in a mammal which comprises administering to said mammal an amount of any one or more of the compounds of formulae I through LII-d (or a pharmaceutically acceptable salt thereof), that is effective in treating abnormal cell growth in combination with an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, antibodies, cytotoxics, anti-hormones, and anti-androgens. In certain embodiments, the compound administered is compound I-a or I-b, or a mixture of I-a and I-b in combination with an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, antibodies, cytotoxics, anti-hormones, and anti-androgens.

This invention also relates to a method of treating abnormal cell growth in a mammal which comprise administering an amount of any one or more of the compounds of formulae I through LII-d, or a pharmaceutically acceptable salt, solvate or prodrug thereof, and an amount of one or more substances selected from anti-angiogenesis agents, signal transduction inhibitors, and antiproliferative agents, which amounts are together effective in treating said abnormal cell growth. In certain embodiments, the compound administered is compound I-a or I-b, or a mixture of I-a and I-b in combination with an amount of one or more substances selected from anti-angiogenesis agents, signal transduction inhibitors, and antiproliferative agents, which amounts are together effective in treating said abnormal cell growth.

Anti-angiogenesis agents, such as MMP-2 (matrix-metalloprotienase 2) inhibitors, MMP-9 (matrix-metalloprotienase 9) inhibitors, and COX-II (cyclooxygenase II) inhibitors, can be used in conjunction with any one or more of the compounds of formulae I through LII-d (or with compounds I-a or I-b, or a mixture of I-a and I-b) in combination with in the methods and pharmaceutical compositions described herein. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain patent application number 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are herein incorporated by reference in their entirety. Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e. MMP-1, MMP-3, MMP-4, MMP-5, MMP-6, MMP-7, MMP-8, MMP-10, MMP-11, MMP-12, and MMP-13). Some specific examples of MMP inhibitors useful in combination with the compounds of the present invention are AG-3340, RO 32-3555, RS 13-0830.

In still other embodiments of the present invention, any one or more of the compounds of formulae I through LII-d (or with compounds I-a or I-b, or a mixture of I-a and I-b) or any pharmaceutically acceptable salts thereof, can also be used in combination with signal transduction inhibitors, such as agents that can inhibit EGFR (epidermal growth factor receptor) responses, such as EGFR antibodies, EGF antibodies, and molecules that are EGFR inhibitors; VEGF (vascular endothelial growth factor) inhibitors; and erbB2 receptor inhibitors, such as organic molecules or antibodies that bind to the erbB2 receptor, for example, HERCEPTIN™ (Genentech, Inc. of South San Francisco, Calif., USA).

EGFR inhibitors are described in, for example in WO 95/19970 (published Jul. 27, 1995), WO 98/14451 (published Apr. 9, 1998), WO 98/02434 (published Jan. 22, 1998), and U.S. Pat. No. 5,747,498 (issued May 5, 1998). EGFR-inhibiting agents include, but are not limited to, CI-1033 (Pfizer Inc.), the monoclonal antibodies C225 and anti-EGFR 22Mab (ImClone Systems Incorporated of New York, N.Y., USA), the compounds ZD-1839 (AstraZeneca), BIBX-1382 (Boehringer Ingelheim), MDX-447 (Medarex Inc. of Annandale, N.J., USA), and OLX-103 (Merck & Co. of Whitehouse Station, N.J., USA), VRCTC-310 (Ventech Research) and EGF fusion toxin (Seragen Inc. of Hopkinton, Mass.).

VEGF inhibitors, for example CP-547,632 and AG-13736 (Pfizer, Inc.), SU-5416 and SU-6668 (Sugen Inc. of South San Francisco, Calif., USA), can also be combined with a compound of formulae I through LII-d (or with compounds I-a or I-b, or a mixture of I-a and I-b). VEGF inhibitors are described in, for example in WO 99/24440 (published May 20, 1999), PCT International Application PCT/IB99/00797 (filed May 3, 1999), in WO 95/21613 (published Aug. 17, 1995), WO 99/61422 (published Dec. 2, 1999), U.S. Pat. No. 5,834,504 (issued Nov. 10, 1998), WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are herein incorporated by reference in their entirety. Other examples of some specific VEGF inhibitors are IM862 (Cytran Inc. of Kirkland, Wash., USA); anti-VEGF monoclonal antibody of Genentech, Inc. of South San Francisco, Calif.; and angiozyme, a synthetic ribozyme from Ribozyme (Boulder, Colo.) and Chiron (Emeryville, Calif.).

ErbB2 receptor inhibitors, such as CP-724,714 (Pfizer, Inc.), GW-282974 (Glaxo Welcome plc), and the monoclonal antibodies AR-209 (Aronex Pharmaceuticals Inc. of The Woodlands, Tex., USA) and 2B-1 (Chiron), may be administered in combination with a compound of formulae I through LII-d (or with compounds I-a or I-b, or a mixture of I-a and I-b). Such erbB2 inhibitors include those described in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), each of which is herein incorporated by reference in its entirety. ErbB2 receptor inhibitors useful in the present invention are also described in U.S. Provisional Application No. 60/117,341, filed Jan. 27, 1999, and in U.S. Provisional Application No. 60/117,346, filed Jan. 27, 1999, both of which are herein incorporated by reference in their entirety.

Other antiproliferative agents that may be used with the compounds of the present invention include inhibitors of HDI (CI-994, Pfizer Inc.), MEK (CI-1040, Pfizer Inc.), the enzyme farnesyl protein transferase and the receptor tyrosine kinase PDGFr, including the compounds disclosed and claimed in the following U.S. patent application Ser. No. 09/221,946 (filed Dec. 28, 1998); Ser. No. 09/454,058 (filed Dec. 2, 1999); Ser. No. 09/501,163 (filed Feb. 9, 2000); Ser. No. 09/539,930 (filed Mar. 31, 2000); Ser. No. 09/202,796 (filed May 22, 1997); Ser. No. 09/384,339 (filed Aug. 26, 1999); and Ser. No. 09/383,755 (filed Aug. 26, 1999); and the compounds disclosed and claimed in the following U.S. provisional patent application Ser. No. 60/168,207 (filed Nov. 30, 1999); Ser. No. 60/170,119 (filed Dec. 10, 1999); Ser. No. 60/177,718 (filed Jan. 21, 2000); Ser. No. 60/168,217 (filed Nov. 30, 1999), and Ser. No. 60/200,834 (filed May 1, 2000). The compounds of the invention may also be used in combination with inhibitors of topoisomerase I, e.g., irinotecan (Camptosar®) and edotecarin. Each of the foregoing patent applications and provisional patent applications is herein incorporated by reference in their entirety.

A compound of formulae I through LII-d (or compounds I-a or I-b, or a mixture of I-a and I-b) may also be used with other agents useful in treating abnormal cell growth or cancer, including, but not limited to, agents capable of enhancing antitumor immune responses, such as CTLA4 (cytotoxic lymphocyte antigen 4) antibodies, and other agents capable of blocking CTLA4; and anti-proliferative agents such as other farnesyl protein transferase inhibitors. Specific CTLA4 antibodies that can be used in the present invention include those described in U.S. Provisional Application Ser. No. 60/113, 647 (filed Dec. 23, 1998) which is hereby incorporated herein by reference in its entirety.

The amount of the compound or composition of the invention (e.g. one or more compounds of formulae I through LII-d or specifically compounds I-a or I-b, or mixtures of I-a and I-b) which will be effective in the prevention, treatment, management, or amelioration of a disorder (e.g., a disorder characterized by or associated with abnormal cell growth, a proliferative disorder, or an inflammatory disorder), or one or more symptoms thereof will vary with the nature and severity of the disease or condition, and the route by which the active ingredient is administered. The frequency and dosage will also vary according to factors specific for each patient depending on the specific therapy (e.g., therapeutic or prophylactic agents) administered, the severity of the disorder, disease, or condition, the route of administration, as well as age, body, weight, response, and the past medical history of the patient. Effective doses may be extrapolated from dose-response curves derived from in vitro or animal model test systems. Suitable regiments can be selected by one skilled in the art by considering such factors and by following, for example, dosages reported in the literature and recommended in the Physician's Desk Reference (57th ed., 2003).

Exemplary doses of one or more compounds of formulae I through LII-d)or specifically compounds I-a or I-b, or mixtures of I-a and I-b) include milligram or microgram amounts of the compound(s) per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram).

In general, the recommended daily dose range of a compound of the invention (e.g. one or more compounds of formulae I through LII-d or specifically compounds I-a or I-b, or mixtures of I-a and I-b) for the conditions described herein lie within the range of from about 0.01 mg to about 1000 mg per day, given as a single once-a-day dose or as divided doses throughout a day. In one embodiment, the daily dose is administered twice daily in equally divided doses. Specifically, a daily dose range should be from about 5 mg to about 500 mg per day, more specifically, between about 10 mg and about 200 mg per day. In managing the patient, the therapy should be initiated at a lower dose, perhaps about 1 mg to about 25 mg, and increased if necessary up to about 200 mg to about 1000 mg per day as either a single dose or divided doses, depending on the patient's response. It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with individual patient response.

Different therapeutically effective amounts may be applicable for different diseases and conditions, as will be readily known by those of ordinary skill in the art. Similarly, amounts sufficient to prevent, manage, treat or ameliorate such disorders, but insufficient to cause, or sufficient to reduce, adverse effects associated with the compounds of the invention are also encompassed by the above described dosage amounts and dose frequency schedules. Further, when a patient is administered multiple dosages of a compound of the invention, not all of the dosages need be the same. For example, the dosage administered to the patient may be increased to improve the prophylactic or therapeutic effect of the compound or it may be decreased to reduce one or more side effects that a particular patient is experiencing.

In a specific embodiment, the dosage of the composition of the invention or a compound of the invention (e.g. one or more compounds of formulae I through LII-d or specifically compounds I-a or I-b, or mixtures of I-a and I-b) is administered to prevent, treat, manage, or ameliorate a disorder (e.g., a disorder characterized by or associated with abnormal cell growth, a proliferative disorder, or an inflammatory disorder), or one or more symptoms thereof in a patient is 150 µg/kg, preferably 250 µg/kg, 500 µg/kg, 1 mg/kg, 5 mg/kg, 10 mg/kg, 25 mg/kg, 50 mg/kg, 75 mg/kg, 100 mg/kg, 125 mg/kg, 150 mg/kg, or 200 mg/kg or more of a patient's body weight. In another embodiment, the dosage of the composition of the invention or a compound of the invention administered to prevent, treat, manage, or ameliorate a disorder (e.g., a disorder characterized by or associated with abnormal cell growth, a proliferative disorder, or an inflammatory disorder), or one or more symptoms thereof in a patient is a unit dose of 0.1 mg to 20 mg, 0.1 mg to 15 mg, 0.1 mg to 12 mg, 0.1 mg to 10 mg, 0.1 mg to 8 mg, 0.1 mg to 7 mg, 0.1 mg to 5 mg, 0.1 mg to 2.5 mg, 0.25 mg to 20 mg, 0.25 mg to 15 mg, 0.25 to 12 mg, 0.25 to 10 mg, 0.25 mg to 8 mg, 0.25 mg to 7 mg, 0.25 mg to 5 mg, 0.5 mg to 2.5 mg, 1 mg to 20 mg, 1 mg to 15 mg, 1 mg to 12 mg, 1 mg to 10 mg, 1 mg to 8 mg, 1 mg to 7 mg, 1 mg to 5 mg, or 1 mg to 2.5 mg.

The dosages of prophylactic or therapeutic agents other than compounds of the invention, that have been or are currently being used to prevent, treat, manage, or ameliorate a disorder (e.g., a disorder characterized by or associated with abnormal cell growth, a proliferative disorder, or an inflammatory disorder), or one or more symptoms thereof can be used in the combination therapies of the invention. Preferably, dosages lower than those which have been or are currently being used to prevent, treat, manage, or ameliorate a disorder (e.g., a disorder characterized by or associated with abnormal cell growth, a proliferative disorder, or an inflammatory disorder), or one or more symptoms thereof are used in the combination therapies of the invention. The recommended dosages of agents currently used for the prevention, treatment, management, or amelioration of a disorder (e.g., a disorder characterized by or associated with abnormal cell growth), or one or more symptoms thereof can obtained from any reference in the art including, but not limited to, Hardman et al., eds., 1996, Goodman & Gilman's The Pharmacological Basis Of Basis Of Therapeutics $9^{th}$ Ed, Mc-Graw-Hill, New York; Physician's Desk Reference (PDR) $57^{th}$ Ed., 2003, Medical Economics Co., Inc., Montvale, N.J., which are incorporated herein by reference in its entirety.

In various embodiment of the methods of the present invention, the therapies (e.g. one or more compounds of formulae I through LII-d or specifically compounds I-a or I-b, or mixtures of I-a and I-b) are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In preferred embodiments, two or more therapies (e.g., prophylactic or therapeutic agents) are administered within the same patient visit.

In certain embodiments, one or more compounds of the invention and one or more of the other therapies (e.g. one or more compounds of formulae I through LII-d or specifically compounds I-a or I-b, or mixtures of I-a and I-b) are administered cyclically. Cycling therapy involves the administration of a first therapy (e.g., a first prophylactic or therapeutic agent) for a period of time, followed by the administration of a second therapy (e.g., a second prophylactic or therapeutic agent) for a period of time, followed by the administration of a third therapy (e.g., a third prophylactic or therapeutic agent) for a period of time and so forth, and repeating this sequential administration to reduce the development of resistance to one of the agents, to avoid or reduce the side effects of one of the agents, and/or to improve the efficacy of the treatment.

In certain embodiments, administration of the same compound of the invention may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same prophylactic or therapeutic agent may be repeated and the administration may be separated by at least at least 1 day, 2 days, 3 days, 5 days, 10 days, 15 days, 30 days, 45 days, 2 months, 75 days, 3 months, or 6 months.

In certain embodiments, the invention provides methods of preventing, treating, managing, or ameliorating a disorder (e.g., a disorder characterized by or associated with abnormal cell growth, a proliferative disorder, or an inflammatory disorder), or one or more symptoms thereof, said methods comprising administering to a subject in need thereof a dose of at least 150 µg/kg, at least 250 µg/kg, at least 500 µg/kg, at least 1 mg/kg, at least 5 mg/kg, at least 10 mg/kg, at least 25 mg/kg, at least 50 mg/kg, at least 75 mg/kg, at least 100 mg/kg, at least 125 mg/kg, at least 150 mg/kg, or at least 200 mg/kg or more of one or more compounds of the invention once every 3 days, once every 4 days, once every 5 days, once every 6 days, once every 7 days, once every 8 days, once every 10 days, once every two weeks, once every three weeks, or once a month.

The present invention encompasses methods of preventing, treating, managing, or preventing a disorder (e.g., a disorder characterized by or associated with abnormal cell growth), or one or more symptoms thereof, said method comprising: (a) administering to a subject in need thereof one or more doses of a prophylactically or therapeutically effective amount of one or more compounds of the invention (e.g. one or more compounds of formulae I through LII-d; and (b) monitoring the mean absolute lymphocyte count in said subject after administration of a certain number of doses of the said compounds of the invention. Moreover, preferably, said certain number of doses is 1, 2, 3, 4, 5, 6, 7, 8, 9, 10 or 12 of a prophylactically or therapeutically effective amount of the one or more compounds of the invention.

In a specific embodiment, the invention provides a method of preventing, treating, managing, or ameliorating a disorder (e.g., a disorder characterized by or associated with abnormal cell growth), or one or more symptoms thereof, said method comprising: (a) administering to a subject in need thereof a dose of at least 150 µg/kg, preferably at least 250 µg/kg, at least 500 µg/kg, at least 1 mg/kg, at least 5 mg/kg, at least 10 mg/kg, at least 25 mg/kg, at least 50 mg/kg, at least 75 mg/kg, at least 100 mg/kg, at least 125 mg/kg, at least 150 mg/kg, or at least 200 mg/kg or more of one or more compounds of the invention (e.g. one or more compounds of formulae I through LII-d or specifically compounds I-a or I-b, or mixtures of I-a and I-b); and (b) administering one or more subsequent doses to said subject when the mean absolute lymphocyte count in said subject is at least approximately 500 cells/mm$^3$, preferably at least approximately 600 cells/mm$^3$, at least approximately 700 cells/mm$^3$, at least approximately 750 cells/mm$^3$, at least approximately 800 cells/mm$^3$, at least approximately 850 cells/mm$^3$, or at least approximately 900 cells/mm$^3$.

As used herein, the term "treat", "treatment" or "treating" refers to a method of alleviating or abrogating a disease, disorder condition and/or symptom thereof, including arresting or inhibiting further development of the disease, condition or disorder.

The term "present" or "preventing" or "prevention" refers to a method of reducing the risk of acquiring a disease, disorder, condition and/or symptom thereof.

3) Pharmaceutical Compositions

In other embodiments, this disclosure encompasses compositions suitable for the treatment or prevention of disease.

In certain embodiments, this invention relates to a pharmaceutical composition for the treatment of abnormal cell growth in a mammal, including a human, comprising an amount of or more compounds of the formulae I through LII-d, as defined above, or a pharmaceutically acceptable salt thereof, that is effective in treating abnormal cell growth, and a pharmaceutically acceptable carrier. In certain embodiments, the invention relates to a pharmaceutical composition for the treatment of abnormal cell growth in a mammal, including a human, comprising an amount of compounds of the formulae I-a through I-b, as defined above, or a pharmaceutically acceptable salt thereof, that is effective in treating abnormal cell growth, and a pharmaceutically acceptable carrier.

In specific embodiments, the compositions comprise one or more compounds of the invention (e.g. any one or more of compounds of formulae I through LII-d, or compounds of the formulae I-a, 1-b or a mixture of I-a and I-b) or a pharmaceutically acceptable salt thereof, and one or more immunomodulatory agents. In another embodiment, a composition comprises one or more compounds of the invention, or a pharmaceutically acceptable salt thereof, and one or more anti-angiogenic agents, wherein the anti-angiogenic agents are not compounds of the invention. In another embodiment, a composition comprises one or more compounds of the invention, or a pharmaceutically acceptable salt thereof, and one or more anti-inflammatory agents, wherein the anti-inflammatory agents are not compounds of the invention. In another embodiment, a composition comprises one or more compounds of the invention, or a pharmaceutically acceptable salt thereof and one or more anti-cancer agents, wherein the anti-cancer agents are not compounds of the invention. In accordance with this embodiment, the anti-cancer agent may or may not be an immunomodulatory agent or an anti-angiogenic agent. In another embodiment, a composition comprises one or more compounds of the invention, or a pharmaceutically acceptable salt thereof, and one or more anti-viral agents. In another embodiment, a composition comprises one or more compounds of the invention, or a pharmaceutically acceptable salt thereof, and one or more antibiotics. In yet another embodiment, a composition comprises one or more compounds of the invention, or a pharmaceutically acceptable salt thereof, and any combination of one, two, three, or more of each of the following prophylactic or therapeutic agents: an immunomodulatory agent, an anti-angiogenic agent, an anti-cancer agent other than an immunomodulatory agent or anti-angiogenic agent, an anti-inflammatory agent, an anti-viral agent, or an anti-bacterial agent (e.g., an antibiotic).

In certain embodiments, a composition of the invention is a pharmaceutical composition or a single unit dosage form. Pharmaceutical compositions and single unit dosage forms of the invention comprise a prophylactically or therapeutically effective amount of one or more prophylactic or therapeutic agents (e.g., a compound of the invention of any of formulae I through LII-d, or compounds of the formulae I-a, I-b or a mixture of I-a and I-b), and typically one or more pharmaceutically acceptable carriers or excipients. In a specific embodiment and in this context, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Examples of suitable pharmaceutical carriers are described in "Remington's Pharmaceutical Sciences" by E. W. Martin.

Typical pharmaceutical compositions and dosage forms comprise one or more excipients. Suitable excipients are well-known to those skilled in the art of pharmacy, and non-limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a patient and the specific active ingredients in the dosage form. The composition or single unit dosage form, if desired, can also contain minor amounts of wetting or emulsifying agents, or pH buffering agents.

Lactose-free compositions of the invention can comprise excipients that are well known in the art and are listed, for example, in the U.S. Pharmacopia (USP)SP (XXI)/NF (XVI). In general, lactose-free compositions comprise an active ingredient, a binder/filler, and a lubricant in pharmaceutically compatible and pharmaceutically acceptable amounts. Preferred lactose-free dosage forms comprise an active ingredient, microcrystalline cellulose, pre-gelatinized starch, and magnesium stearate.

This invention further encompasses anhydrous pharmaceutical compositions and dosage forms comprising active ingredients (e.g. any one or more compound having formulae I through LII-d or compounds of the formulae I-a, I-b or a mixture of I-a and I-b), since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, Drug Stability: Principles & Practice, 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further encompasses pharmaceutical compositions and dosage forms that comprise any one or more compound having formulae I through LII-d and one or more compounds that reduce the rate by which an active ingredient will decompose. Such compounds, herein referred to as "stabilizers," include, but are not limited to, antioxidants such as ascorbic acid, pH buffers, or salt buffers.

The pharmaceutical compositions and single unit dosage forms can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Such compositions and dosage forms will contain a prophylactically or therapeutically effective amount of a prophylactic or therapeutic agent preferably in purified form, together with a suitable amount of carrier so as to provide the form for proper administration to the patient. The formulation should suit the mode of administration. In certain embodiments, the pharmaceutical compositions or single unit dosage forms are sterile and in suitable form for administration to a subject, preferably an animal subject, more preferably a mammalian subject, and most preferably a human subject.

A pharmaceutical composition of the invention is formulated to be compatible with its intended route of administration. Examples of routes of administration include, but are not limited to, parenteral, e.g., intravenous, intradermal, subcutaneous, oral (e.g., inhalation), intranasal, transdermal (topical), transmucosal, intra-tumoral, intra-synovial and rectal administration. In a specific embodiment, the composition is formulated in accordance with routine procedures as a pharmaceutical composition adapted for intravenous, subcutaneous, intramuscular, oral, intranasal or topical administration to human beings. In certain embodiments, a pharmaceutical composition is formulated in accordance with routine procedures for subcutaneous administration to human beings. Typically, compositions for intravenous administration are solutions in sterile isotonic aqueous buffer. Where necessary, the composition may also include a solubilizing agent and a local anesthetic such as lignocane to ease pain at the site of the injection. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the invention will typically vary depending on their use. For example, a dosage form used in the acute treatment of inflammation or a related disorder may contain larger amounts of one or more of the active ingredients it comprises than a dosage form used in the chronic treatment of the same disease. Also, the therapeutically effective dosage form may vary among different types of cancer. Similarly, a parenteral dosage form may contain smaller amounts of one or more of the active ingredients it comprises than an oral dosage form used to treat the same disease or disorder. These and other ways in which specific dosage forms encompassed by this invention will vary from one another will be readily apparent to those skilled in the art. See, e.g., Remington's Pharmaceutical Sciences, 18th ed., Mack Publishing, Easton Pa. (1990).

Generally, the ingredients of compositions of the invention are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration. Typical dosage forms of the invention comprise a compound of the invention, or a pharmaceutically acceptable salt thereof lie within the range of from about 1 mg to about 1000 mg per day, given as a single once-a-day dose in the morning but preferably as divided doses throughout the day taken with food.

Pharmaceutical compositions of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's Pharmaceutical Sciences, 18th ed., Mack Publishing, Easton Pa. (1990).

Typical oral dosage forms of the invention are prepared by combining the active ingredient(s) in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage fowls of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

Delayed Release Dosage Forms

Active ingredients of the invention can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the invention.

Transdermal, Topical & Mucosal Dosage Forms

Transdermal, topical, and mucosal dosage forms of the invention include, but are not limited to, ophthalmic solutions, sprays, aerosols, creams, lotions, ointments, gels, solutions, emulsions, suspensions, or other forms known to one of skill in the art. See, e.g., Remington's Pharmaceutical Sciences, 16th and 18th eds., Mack Publishing, Easton Pa. (1980 & 1990); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form lotions, tinctures, creams, emulsions, gels or ointments, which are non-toxic and pharmaceutically acceptable. Moisturizers or humectants can also be added to pharmaceutical compositions and dosage forms if desired. Examples of such additional ingredients are well known in the art. See, e.g., Remington's Pharmaceutical Sciences, 16th and 18th eds., Mack Publishing, Easton Pa. (1980 & 1990).

Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts of the active ingredients can be used to further adjust the properties of the resulting composition.

Biological Assays

The anti-cancer activity of the pharmaceutical compositions and compounds of the invention can be determined using any suitable animal model, including, but not limited to, SCID mice with a tumor or injected with malignant cells. An example of an animal model for breast cancer includes, but is not limited to, a transgenic mouse that over-expresses cyclin D1 (see, e.g., Hosokawa et al., 2001, Transgenic Res 10(5): 471-8). Examples of animal models for pancreatic cancer include, but are not limited to, a metastatic model of Panc02 murine pancreatic adenocarcinoma (see, e.g., Wang et al., 2001, Int J Pancreatol 29(1)37-46) and nu-nu mice generated in subcutaneous pancreatic tumors (see, e.g., Ghaneh et al., 2001, Gene Ther 8(3):199-208). Examples of animal models for lung cancer include, but are not limited to, lung cancer animal models described by Zhang & Roth (1994, In Vivo 8(5):755-69) and a transgenic mouse model with disrupted p53 function (see, e.g., Morris et al., 1998, J La State Med Soc 150(4):179-85). Examples of animal models for non-Hodgkin's lymphoma include, but are not limited to, a severe combined immunodeficiency ("SCID") mouse (see, e.g., Bryant et al., 2000, Lab Invest 80(4):553-73) and an IgHmu-HOX11 transgenic mouse (see, e.g., Hough et al., 1998, Proc Natl Acad Sci USA 95(23):13853-8). An example of an animal model for esophageal cancer includes, but is not limited to, a mouse transgenic for the human papillomavirus type 16 E7 oncogene (see, e.g., Herber et al., 1996, J Virol 70(3): 1873-81). Examples of animal models for colorectal carcinomas include, but are not limited to, Apc mouse models (see, e.g., Fodde & Smits, 2001, Trends Mol Med 7(8):369-73 and Kuraguchi et al., 2000, Oncogene 19(50):5755-63).

4) Nutraceutical Compositions

This invention further relates to compositions suitable for use as dietary supplements or nutraceuticals for the treatment or prevention of disease. In certain embodiments, the present invention encompasses nutraceutical compositions comprising one or more of compounds I through LII-d.

In certain embodiments, the present invention encompasses nutraceutical compositions containing compounds I-a or I-b or mixtures of the two.

In certain embodiments, nutraceutical compositions of the present invention encompass materials derived from plants of the genus *Guaiacum*. In certain embodiments, the invention encompasses nutraceutical compositions containing extracts, powders, resins, oils, gums, sap or residues derived from a *Guaiacum* species selected from the group consisting of: *G. abilo; G. afrum; G. angustifolium* (Guyacan); *G. arboreum; G. bijugum; G. breynii; G. coulteri* (Guayacan); *G. coulteri* var. *palmeri; G. dubium; G. guatemalense; G. hygrometricum; G. mexicanum; G. microphyllum; G. multijugum; G. officinale* (Commoner Lignum Vitae); *G. palmeri; G. parvifolium; G. planchoni; G. planchonii; G. sanctum* (Guaiacum); *G. sanctum f. angustifolia; G. sanctum lignum; G. sloanei; G. unijugum*; and *G. vertical*. In certain embodiments, the *Guaiacum* extracts or components present in the nutraceutical composition are derived from *Guaiacum officinale*. In certain embodiments, the *Guaiacum* extracts or components present in the nutraceutical composition are derived from *Guaiacum sanctum*.

In certain embodiments, the nutraceutical compositions comprise extracts, powders, resins, oils, gums, sap or residues derived from heartwood of one or more plants from the genus *Guaiacum*. In certain embodiments, the heartwood is derived from *Guaiacum officinale* or *Guaiacum sanctum*. In certain embodiments, the nutraceutical compositions comprise extracts of the heartwood of *Guaiacum officinale* or *Guaiacum sanctum*.

In certain embodiments, the present invention encompasses nutraceutical compositions containing compounds I-a or I-b or a mixture of the two in defined concentrations and dosage forms to provide calibrated quantities of those compounds.

In some embodiments, the *Guaiacum* extracts are treated to increase the concentration of compounds having formulae I through LII-d as described hereinabove. In certain embodiments the extracts are processed to increase the concentration of compounds having formula I-a and/or I-b.

In certain embodiments, the present invention encompasses nutraceutical compositions containing compounds I-a or I-b or a mixture of the two in combination with other compounds present plants of the genus *Guaiacum*.

In certain embodiments, nutraceutical compositions of the present invention encompass compositions containing compounds I-a or I-b or a mixture of the two in combination with one or more lignans selected from the group consisting of: nectandrin B, isonectandrin B, machilin I, podophyllotoxin, Secoisolariciresinol, Secoisolariciresinol Diglucoside, meso-dihydroguaiaretic acid, 7-hydroxymatairesinol and a combination of two or more of the above.

In certain embodiments, nutraceutical compositions of the present invention encompass compositions containing compounds I-a or I-b or a mixture of the two in combination with one or more compounds present in plants of the genus *Guaiacum*. In certain embodiments, nutraceutical compositions of the present invention encompass compositions containing compounds I-a or I-b or a mixture of the two in combination with one or more lignans present in plants of the genus *Guaiacum*. In certain embodiments, nutraceutical compositions of the present invention encompass compositions containing compounds I-a or I-b or a mixture of the two in combination with one or more compounds selected from the group consisting of: nectandrin B, isonectandrin B, machilin I, and meso-dihydroguaiaretic acid.

In certain embodiments nutraceutical compositions of the present invention encompass materials derived from plants of the genus *Guaiacum* wherein the materials have been treated to remove certain compounds. In certain embodiments, the plant materials have been treated to remove compounds having toxicity, side-effects, or undesirable physiological effects. In certain embodiments, the compounds thus removed include nordihydroguaiaretic acid, and/or derivatives and/or isomers thereof. In certain embodiments, the compounds thus removed include meso-dihydroguaiaretic acid, and/or derivatives and/or isomers thereof.

In other embodiments, the present invention encompasses nutraceutical compositions wherein compounds I-a or I-b are present in the form of extracts, powders, resins, oils, gums, sap or residues derived from parts of one or more plants containing these compounds. In certain embodiments, the parts of the plant include heartwood. In certain embodiments, such plants belong to the genus *Guaiacum*.

In certain embodiments the plant extracts, powders, resins, oils, gums, sap or residues present in nutraceutical composition of the present invention are processed to increase the concentration of compounds I-a and/or I-b relative to the unprocessed plant material. In certain embodiments of the present invention the plant extracts, powders, resins, oils, gums, sap, residues or other components are assayed to determine the concentration of compounds I-a and/or I-b prior to incorporation of such materials into the nutraceutical compositions. In certain embodiments, the nutraceutical composition is compounded from the plant extracts, powders, resins, oils, gums, sap, residues or other components using the assay results to determine the amount of the material required to provide a consistent concentration of compounds I-a and/or I-b in the nutraceutical composition.

In certain embodiments of the present invention, the *Guaiacum* extracts or components used in the nutraceutical composition are derived from the heartwood of the plant. In other embodiments, the *Guaiacum* extracts or components are derived from *Guaiacum* resin (gum guaiac). In certain embodiments, the *Guaiacum* extracts or components are derived from tincture of guaiac.

This invention further relates to nutraceutical compositions for the treatment or prevention of abnormal cell growth in a mammal, including a human, comprising an amount of a compound of the formulae I through LII-d, as defined above, or an acceptable salt, solvate or metabolic precursor thereof, that is effective in treating or preventing abnormal cell growth, in combination with a material having nutritional value. Suitable materials having nutritional value include, but are not limited to vitamins, minerals, fatty acids or amino acids.

This invention further relates to nutraceutical compositions for the treatment or prevention of proliferative disorders in a mammal, including a human, comprising an amount of a compound of the formulae I through LII-d, as defined above, or an acceptable salt, solvate or metabolic precursor thereof, that is effective in treating or preventing abnormal cell growth, in combination with a material having nutritional value. Suitable materials having nutritional value include, but are not limited to vitamins, minerals, fatty acids or amino acids.

This invention further relates to nutraceutical compositions for the treatment or prevention of proliferative disorders in a mammal, including a human, comprising an amount of a compound of the formulae Ia and/or I-b, as defined above, or an acceptable salt, solvate or metabolic precursor thereof, that is effective in treating or preventing abnormal cell growth, in combination with a material having nutritional value. Suitable materials having nutritional value include, but are not limited to vitamins, minerals, fatty acids or amino acids.

The nutraceutical compositions of the invention can also include one or more other ingredients that impart additional healthful or medicinal benefit. The optional ingredients useful herein can be categorized by their healthful benefit or their postulated mode of action. However, it is to be understood that the optional components useful herein can in some instances provide more than one healthful benefit or operate via more than one mode of action. Therefore, classifications herein are made for the sake of convenience and are not intended to limit the component to any particular mechanism of action or to that particular application or applications listed.

A nutraceutical composition can comprise in addition to one or more compound(s) or composition(s) of the invention (e.g. one or more compounds of formulae I through LII-d, or more specifically compounds I-a, I-b, or mixtures of I-a and I-b), and one or more additional ingredient(s), such as but not limited to vitamins, minerals, electrolytes, sports nutritional products, amino acids, probiotics, metabolites, hormones, enzymes, cartilage products, botanical extracts, and homeopathic products. More specifically, a nutracential composition of the invention can further one or more substance(s) from the following non-limiting categories: (i) amino acids and oligopeptides, such as but not limited to 5-hydroxytryptophan, acetyl-L-carnitine, acetylcysteine, arginine pyroglutamate, branched-chain amino acids, creatine, DL-phenylalanine (phenylalanine), dimethylglycine (DMG), glutamine peptides, glutathione, glycine, insulin-like growth factor 1, L-arginine (arginine), L-aspartate, L-carnitine, L-cysteine, L-glutamine, L-histidine, L-lysine (lysine), L-methionine (methionine), L-ornithine, phenylalanine (phenylalanine), L-theanine, L-tyrosine (tyrosine), lactoferrin, ornithine alpha-ketoglutarate, para-aminobenzoic acid (aminobenzoic acid), taurine; (ii) glycosupplements, such as but not limited to chitosan, chondroitin sulfate, D-glucarate, D-ribose, fructo-oligosaccharides, glucomannan, glucosamine, inulins (inulin), lactulose, larch arabinogalactan, modified citrus pectin, pectin, psyllium (psyllium husk), sodium alginates, yeast beta-D-glucans; (iii) hormones, such as but not limited to 19-norandrostenedione, androstenediol, androstanedione, beta-sitosterol, biochanin A, DHEA, glandulars, human growth hormone and secretagogues (somatropin), ipriflavone, melatonin, pregnenolone, soy isoflavones, tiratricol (TRIAC); lipids such as but not limited to alkoxyglycerols, blackcurrant seed oil, borage oil, caprylic acid, cetyl myristoleate, conjugated linoleic acid (CLA), docahexaenoic acid (DHA), eicosapentaenoic acid (EPA), evening primrose oil, fish oil, flaxseed oil, gamma-linolenic acid (GLA), glycerol (glycerin), hemp seed oil, hexacosanol, inositol hexaphosphate, L-alpha-glycerylphosphorylcholine (Alpha-GPC), lithium gamma-linolenic acid (Li-GLA), medium-chain triglycerides, myo-inositol, octacosanol, perilla oil, phosphatidylcholine, phosphatidylserine, policosanol, squalene, plant stanols; (iv) metabolites and cofactors such as but not limited to 7-oxo-dehydroepiandrosterone, alpha-lipoic acid, betaine and betaine hydrochloride, CDP-choline (citicolin sodium), coenzyme Q10 (CoQ10), NADH, pantethine, pyruvate, S-adenosyl-L-methione (SAMe); (v) minerals and electrolytes, such as but not limited to metal salts, chelated minerals, colloidal minerals, colloidal silver, colloidal gold, bentonite, compounds comprising aluminum, arsenic, boron, bromine, calcium, chromium, copper, fluoride, germanium, iodine, iron, lithium, magnesium, manganese, molybdenum, nickel, phosphorus, potassium, selenium, selenium, silicon, tin, vanadium, and zinc; (vi) mycosupplements such as but not limited to brewer's yeast, kombucha, myco-polysaccharides, red yeast rice; (vii) inosine, nucleic acids, nucleotides; (viii) microorganisms such as but limited to prebiotics, probiotics, symbiotics, yoghurt organisms; (ix) proteins such as but not limited to bovine cartilage, bovine colostrum, bromelain (bromelains), chicken collagen II, gelatin hydrolysates (gelatin), hydrolyzed collagen, shark cartilage, soy protein, whey proteins; (x) vitamins in either natural or synthetic form, such as but are not limited to, vitamin A (e.g., beta carotene, retinoic acid, retinol, retinoids, retinyl palmitate, retinyl proprionate, etc.), vitamin B (e.g., niacin, niacinamide, riboflavin, pantothenic acid, etc.), vitamin B6 (pyridoxine hydrochloride), vitamin B12 (cyanocobalamin), vitamin C (e.g., ascorbic acid, etc.), vitamin D (e.g., ergosterol, ergocalciferol, cholecalciferol, etc.), Vitamin E (e.g., tocopherol acetate, etc.), vitamin K (e.g., phytonadione, menadione, phthiocol, etc.), alpha-tocopheryl nicotinate, alpha-tocopheryl polyethylene glycol succinate, ascorbyl palmitate, biotin, folate (folio acid), gamma-tocopherol, inositol nicotinate (inositol niacinate), niacin, nicotinamide (niacinamide), pantothenic acid (calcium pantothenate), thiamin, and tocotrienols; (xi) botantical extracts such as DHEA, Ginkgo biloba extracts, ginseng extracts, reisi (Ganoderma) extract; and (xii) other supplements known in the art such as but not limited to activated charcoal, beta-hydroxy-beta-methylbutyrate (HMB), choline, colosolic acid, deanol, dimethyl sulfoxide (DMSO), dolomite, gamma-butyrolactone (GBL), gamma-hydroxybutyrate (GHB), liver hydrolysate/desiccated liver, malic acid, methylsulfonylmethane (MSM), royal jelly, vinpocetine, arnica, bee pollen, chlorella, chlorophyll/chlorophyllin (chlorophyllin copper complex), chrysin, cocoa flavonoids, curcuminoids, daidzein, deglycyrrhizinated licorice (DGL), flower pollen, genistein, glycitein, grape seed proanthocyanidins, green tea catechins, black tea theaflavins, hesperetin, hesperidin, huperzine A, hydroxycitric acid, hydroxyethylrutosides, indole-3-carbinol, lutein and zeaxanthin, lycopene, oat beta-D-glucan, phytostanols, phytosterols, piperine, propolis, pycnogenol, quercetin, resveratrol, rutin, secoisolariciresinol diglycoside (SDG), soy isoflavones, spirulina, sulforaphane, wheat grass/barley grass.

Non-limiting examples of minerals and electrolytes include but are not limited to calcium compounds, calcium carbonate, calcium citrate, iron compounds, iron fumarate, iron gluconate, iron sulfate, magnesium compounds, magnesium carbonate, magnesium chloride, magnesium gluconate, selenium compounds, sodium compounds, and manganese compounds.

Also encompassed by the invention are nutraceutical compositions comprising one or more compound(s) or composition(s) of the invention (e.g. one or more compounds of formulae I through LII-d, or more specifically compounds I-a, I-b, or mixtures of I-a and I-b) and one or more "Generally Regarded As Safe" ("GRAS") substance(s). Many GRAS substances are known and are listed in the various sections of the regulations of the United States public health authority, 21 CFR 73, 74, 75, 172, 173, 182, 184 and 186, which are incorporated herein by reference in their entirety. Thus, in various embodiments, a dietary supplement, food composition or food additive of the invention comprises one or more GRAS substances.

For example, the following exemplary GRAS flavor alcohols can be used in combination with the compounds and compositions of the invention, benzyl alcohol, acetoin (acetylmethylcarbinol), ethyl alcohol (ethanol), propyl alcohol (1-propanol), iso-propyl alcohol (2-propanol, isopropanol), propylene glycol, glycerol, n-butyl alcohol (n-propyl carbinol), iso-butyl alcohol (2-methyl-1-propanol), hexyl alcohol (hexanol), L-menthol, octyl alcohol (n-octanol), cinnamyl alcohol (3-phenyl-2-propene-1-ol), .alpha.-methyl-benzyl alcohol (1-phenyl-ethanol), heptyl alcohol (heptanol), n-amyl alcohol (1-pentanol), iso-amyl alcohol (3-methyl-1-butanol), anisalcohol (4-methoxybenzyl alcohol, p-anisalcohol), citronellol, n-decyl alcohol (n-decanol), geraniol, beta-gamma-hexanol (3-hexenol), lauryl alcohol (dodecanol), linalool, nerolidol, nonadienol (2,6-nonadiene-1-ol), nonyl alcohol (nonanol-1), rhodinol, terpineol, borneol, clineol (eucalyptol), anisole, cuminyl alcohol (cuminol), 10-undecen-1-ol, 1-hexadecanol. Suitable derivatives include, for example, the esters, ethers and carbonates of the above mentioned GRAS flavor alcohols are also contemplated. Particularly preferred GRAS flavor alcohols are benzyl alcohol, 1-propanol, glycerol, propylene glycol, n-butyl alcohol, citronellol, hexanol, linalool, acetoin and their derivatives.

Also encompassed is the inclusion of one or more GRAS polyphenols in the nutraceutical compositions of the invention, such as but not limited to catechol, resorcinol, hydroquinone, phloroglucinol, pyrogallol, cyclohexane, usnic acid, acylpolyphenols, lignins, anthocyans, flavones, catechols, gallic acid derivatives (e.g., tannins, gallotannin, tannic acids, gallotannic acids), catechins, theaflavins, camosol, camosolic acid (including their derivatives, such as (2,5-dihydroxyphenyl)carboxylic and (2,5-dihydroxyphenyl)alkylenecarboxylic substitutions, salts, esters, amides), caffeic acid and its esters and amides, flavonoids (e.g., flavone, flavonol, isoflavone, gossypetin, myricetin, robinetin, apigenin, morin, taxifolin, eriodictyol, naringin, rutin, hesperidin, troxerutin, chrysin, tangeritin, luteolin, catechols, quercetin, fisetin, kaempferol, galangin, rotenoids, aurones, flavonols, diols), extracts, e.g., from *Camellia* (*C. sinensis* in particular), or *Primula*. Further, their derivatives, e.g., salts, acids, esters, oxides and ethers, may also be used.

Also encompassed is the inclusion of one or more GRAS acids in the nutraceutical compositions of the invention, such as but not limited to acetic acid, aconitic acid, adipic acid, formic acid, malic acid (1-hydroxysuccinic acid), capronic acid, hydrocinnamic acid (3-phenyl-1-propionic acid), pelargonic acid (nonanoic acid), lactic acid (2-hydroxypropionic acid), phenoxyacetic acid (glycolic acid phenyl ether), phenylacetic acid (alpha-toluenic acid), valeric acid (pentanoic acid), iso-valeric acid (3-methylbutyric acid), cinnamic acid (3-phenylpropenoic acid), citric acid, mandelic acid (hydroxyphenylacetic acid), tartaric acid (2,3-dihydroxybutanedioic acid; 2,3-dihydroxysuccinic acid), fumaric acid, tannic acid and their derivatives. Suitable derivatives according to the present invention are esters (e.g., $C_{1\text{-}6}$-alkyl esters and benzyl esters), amides (including N-substituted amides) and salts (alkali, alkaline earth and ammonium salts) of the above mentioned acids. According to the present invention, the term "derivatives" also encompasses modifications of the sidechain hydroxy functions (e.g., acyl and alkyl derivatives) and modifications of the double bonds (e.g., the perhydrogenated and hydroxylated derivatives of the mentioned acids).

Also encompassed is the inclusion of one or more GRAS phenols in the nutraceutical compositions of the invention, such as but not limited to thymol, methyleugenol, acetyleugenol, safrol, eugenol, isoeugenol, anethole, methylchavicol (estragol; 3-(4-methoxyphenyl)-1-propene), carvacrol, alpha-bisabolol, fomesol, anisole (methoxybenzene), propenylguaethol (5-propenyl-2-ethoxyphenol) and their derivatives. Derivatives according to the present invention are compounds in which the phenolic hydroxy group has been esterified or etherified.

Also encompassed is the inclusion of one or more GRAS esters in the nutraceutical compositions of the invention, such as but not limited to allicin and the following acetates may be used, for example: iso-amyl acetate (3-methyl-1-butyl acetate), benzyl acetate, benzylphenyl acetate, n-butyl acetate, cinnamyl acetate (3-phenylpropenyl acetate), citronellyl acetate, ethyl acetate (acetic ester), eugenol acetate (acetyleugenol), geranyl acetate, hexyl acetate (hexanyl ethanoate), hydrocinnamyl acetate (3-phenylpropyl acetate), linalyl acetate, octyl acetate, phenylethyl acetate, terpinyl acetate, triacetin (glyceryl triacetate), potassium acetate, sodium acetate and calcium acetate.

Also encompassed is the inclusion of one or more GRAS terpenes in the nutraceutical compositions of the invention, such as but not limited to camphor, limonene and beta-caryophyllene.

Also encompassed is the inclusion of one or more GRAS acetals in the nutraceutical compositions of the invention, such as but not limited to acetal, acetaldehyde dibutyl acetal, acetaldehyde dipropyl acetal, acetaldehyde phenethyl propyl acetal, cinnamic aldehyde ethylene glycol acetal, decanal dimethyl acetal, heptanal dimethyl acetal, heptanal glyceryl acetal and benzaldehyde propylene glycol acetal.

Also encompassed is the inclusion of one or more GRAS acetaldehydes in the nutraceutical compositions of the invention, such as but not limited to acetaldehyde, anisaldehyde, benzaldehyde, iso-butyl aldehyde (methyl-1-propanal), citral, citronellal, n-caprylic aldehyde (n-decanal), ethylvanillin, furfural, heliotropin (piperonal), heptyl aldehyde (heptanal), hexyl aldehyde (hexanal), 2-hexenal (beta-propylacrolein), hydrocinnamic aldehyde (3-phenyl-1-propanal), lauryl aldehyde (dodecanal), nonyl aldehyde (n-nonanal), octyl aldehyde (n-octanal), phenylacetaldehyde (1-oxo-2-phenylethane), propionaldehyde (propanal), vanillin, cinnamic aldehyde (3-phenylpropenal), perillaldehyde and cuminaldehyde.

Also encompassed is the inclusion of one or more GRAS essential oils in the nutraceutical compositions of the invention, such as but not limited to essential oils and/or alcoholic or glycolic extracts or extracts obtained by high-pressure carbon-dioxide processes from plants such as: oils or extracts having a high content of alcohols: melissa, coriander, cardamon, eucalyptus; oils or extracts having a high content of aldehydes: Eucalyptus citriodora, cinnamon, lemon, lemon grass, melissa, citronella, lime, orange; oils or extracts having a high content of phenols: origanum, thyme, rosemary, orange, clove, fennel, camphor, mandarin, anise, cascarilla, estragon and pimento; oils or extracts having a high content of acetates: lavender; oils or extracts having a high content of esters: mustard, onion, garlic; oils or extracts having a high content of terpenes: pepper, bitter orange, caraway, dill, lemon, peppermint, nutmeg; oils or extracts having a high content of acids: olibanum.

Any of the additional substances in a nutraceutical composition of the invention may be included as pure or substantially pure material, or for example, as an extract obtained by suitable physical and/or chemical isolation from natural (e.g., plant) sources.

In certain embodiments, the nutraceutical compositions of the present invention comprise from about 0.001% to about 90%, by weight of the compound(s) or composition of the invention (e.g. of one or more compounds of formulae I through LII-d, or more specifically compounds I-a, I-b, or mixtures of I-a and I-b). In certain embodiments, the nutraceutical compositions of the present invention comprise from about 0.001% to about 90%, by weight of one or more compounds of formulae I-a and/or I-b. In certain embodiments, the nutraceutical compositions of the present invention comprise from about 0.001% to about 90%, by weight of one compound I-a, compound I-b, or a mixture of compounds I-a and I-b. Other amounts of the compounds I-a and/or I-b in the nutraceutical compositions that are also contemplated are from about 0.0075% to about 75%, about 0.005% to about 50%, about 0.01% to about 35%, 0.1% to about 20%, 0.1% to about 15%, 1% to about 10%, and 2% to about 7%, by weight of the compound(s) or composition of the invention.

In other embodiments, the present invention encompasses botanical drug products. As used herein, the term "botanical drug product" and related terms including "botanical drug substance", "botanical raw material", are used as defined in *Guidance for Industry: Botanical Drug Products*, Published by the U.S. Department of Health and Human Services, Food and Drug Administration, Center for Drug Evaluation and Research (CDER) in June 2004, the entire content of which is incorporated herein by reference.

In certain embodiments the botanical drug products of the invention comprise any of the compositions described hereinabove as nutraceuticals.

In certain embodiments, the present invention encompasses botanical drug products comprising extracts, powders, resins, oils, sap, or residues from plants of the genus *Guaiacum*. In certain embodiments, the extracts, powders, resins, oils, sap, or residues contain one or more compounds selected from the group consisting of any of compounds I through LII-b, compound I-a, compound I-b, mixtures of I-a and I-b, nectandrin B, isonectandrin B, machilin I, guaiaretic acid, dihydroguaiaretic acid, nordihydroguaiaretic acid, guaiacic and α and β guaiaconic acids, furoguaiacidin and a combination of two or more of the above.

In certain embodiments, botanical drug products of the present invention comprise botanical drug substances containing at least one of compounds I-a or I-b. In certain embodiments, botanical drug products of the present invention comprise Single-Herb botanical drug substances containing at least one of compounds I-a or I-b. In certain embodiments, botanical drug products of the present invention comprise Multi-Herb botanical drug substances containing at least one of compounds I-a or I-b.

In certain embodiments, botanical drug products of the present invention comprise single-herb botanical substances wherein the active constituent(s) is/are derived from one species in the genus *Guaiacum*. In certain embodiments, the species is selected from the group consisting of: *G. abilo; G. afrum; G. angustifolium* (Guyacan); *G. arboreum; G. bijugum; G. breynii; G. coulteri* (Guayacan); *G. coulteri* var. *palmeri; G. dubium; G. guatemalense; G. hygrometricum; G. mexicanum; G. microphyllum; G. multijugum; G. officinale* (Commoner Lignum Vitae); *G. palmeri; G. parvifolium; G. planchoni; G. planchonii; G. sanctum* (Guaiacum); *G. sanctum f. angustifolia; G. sanctum lignum; G. sloanei; G. unijugum*; and *G. vertical*. In certain embodiments, the *Guaiacum* species present in the botanical drug product is *Guaiacum officinale*. In certain embodiments, the *Guaiacum* species present in the botanical drug product is *Guaiacum sanctum*.

In other embodiments, the botanical drug products of the present invention comprise multi-herb botanical substances. In certain embodiments, the botanical drug product contains two or more *Guaiacum* species selected from the group consisting of: *G. abilo; G. afrum; G. angustifolium* (Guyacan); *G. arboreum; G. bijugum; G. breynii; G. coulteri* (Guayacan); *G. coulteri* var. *palmeri; G. dubium; G. guatemalense; G. hygrometricum; G. mexicanum; G. microphyllum; G. multijugum; G. officinale* (Commoner Lignum Vitae); *G. palmeri; G. parvifolium; G. planchoni; G. planchonii; G. sanctum* (Guaiacum); *G. sanctum f. angustifolia; G. sanctum lignum; G. sloanei; G. unijugum*; and *G. vertical*.

In other embodiments the multi-herb botanical drug products of the present invention contain two or more botanicals from different genera. In one embodiment, the botanical drug product contains one botanical from the genus *Guaiacum* and one botanical from the genus *Linum*. In certain embodiments the botanical from the genus *Linum* comprises a material derived from the seed hulls of the plant. In certain embodiments the botanical from the genus *Linum* comprises *L. usitatissimum*. In certain embodiments, the botanical from the genus *Linum* comprises extracts from the seed hulls of *L. usitatissimum*.

In certain embodiments, the botanical drug substance comprises two or more materials selected from the group consisting of compound I-a, compound I-b, a mixture of compounds I-a and I-b, nectandrin B, isonectandrin B, and machilin I, podophyllotoxin, secoisolariciresinol, secoisolariciresinol diglycoside, meso-dihydroguaiaretic acid, nordihydroguaiaretic acid, and 7-hydroxymatairesinol.

In certain embodiments, the botanical drug product comprises two or more materials selected from the group consisting of compound I-a, compound I-b, a mixture of compounds I-a and I-b, nectandrin B, isonectandrin B, machilin I, and meso-dihydroguaiaretic acid. In certain embodiments, the botanical drug product comprises contains a mixture of compounds I-a, I-b, and nectandrin B. In certain embodiments, the botanical drug product comprises contains a mixture of compounds I-a, I-b, and isonectandrin B. In certain embodiments, the botanical drug product comprises contains a mixture of compounds I-a, I-b, and machilin I. In certain embodiments, the botanical drug product comprises contains a mixture of compounds I-a, I-b, and meso-dihydroguaiaretic acid.

In certain embodiments, the botanical drug product comprises two or more materials selected from the group consisting of compound I-a, compound I-b, a mixture of compounds I-a and I-b, nectandrin B, isonectandrin B, and machilin I, podophyllotoxin, secoisolariciresinol, secoisolariciresinol diglycoside, meso-dihydroguaiaretic acid, nordihydroguaiaretic acid, and 7-hydroxymatairesinol. In certain embodiments, the botanical drug product comprises contains a mixture of compounds I-a, I-b, and 7-hydroxymatairesinol. In certain embodiments, the botanical drug product comprises a mixture of compounds I-a, I-b, and secoisolariciresinol diglycoside.

In certain embodiments, the botanical drug substance contains defined amounts of one or more materials selected from the group consisting of: compound I-a, compound I-b, and a mixture of compounds I-a and I-b. In certain embodiments, the botanical drug substance contains defined amounts of compound I-b. In certain embodiments, the botanical drug substance contains defined amounts of a mixture of compounds I-a and I-b.

In certain embodiments, the botanical drug substance contains defined amounts of one or more materials selected from the group consisting of: compound I-a, compound I-b, and a mixture of compounds I-a, and I-b, along with a defined amount of secoisolariciresinol diglycoside. In certain embodiments, the botanical drug substance contains defined amounts of compounds I-a and secoisolariciresinol diglycoside. In certain embodiments, the botanical drug substance contains defined amounts of compounds I-b and secoisolariciresinol diglycoside. In certain embodiments, the botanical drug substance contains defined amounts of compounds a mixture of compounds I-a, I-b, and secoisolariciresinol diglycoside.

The amount of the active constituents in botanical drug products of the present invention will obviously be dependent upon the dosage form, the clinical indication being treated, and other specifics of the patient's medical condition. In general, the recommended daily dose range botanical drug product of the present invention for the conditions described herein lie within the range of from about 0.01 mg to about 5000 mg of botanical substance or extract per day, given as a single once-a-day dose or as divided doses throughout a day. In one embodiment, the daily dose is administered twice daily in equally divided doses. Specifically, a daily dose range should be from about 5 mg to about 1000 mg per day, more specifically, between about 10 mg and about 200 mg per day. In managing the patient, the therapy should be initiated at a lower dose, perhaps about 1 mg to about 25 mg, and increased if necessary up to about 200 mg to about 1000 mg per day as either a single dose or divided doses, depending on the patient's response. It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with individual patient response.

In certain embodiments of the present invention the amount of compounds I-a, I-b, or the mixture of I-a and I-b present in a single dose of the botanical drug substance, ranges from about 10 µg to about 500 mg. In certain embodiments, the amount of compounds I-a, I-b, or the mixture of I-a and I-b present in the botanical drug substance ranges from about 2 mg to about 200 mg. In certain embodiments, the amount of compounds I-a, I-b, or the mixture of I-a and I-b present in the botanical drug substance ranges from about 5 mg to about 150 mg. In certain embodiments, the amount of compounds I-a, I-b, or the mixture of I-a and I-b present in the botanical drug substance ranges from about 10 mg to about 100 mg. In certain embodiments, the amount of compounds I-a, I-b, or the mixture of I-a and I-b present in the botanical drug substance ranges from about 20 mg to about 50 mg. In certain embodiments, the amount of compounds I-a, I-b, or the mixture of I-a and I-b present in the botanical drug substance ranges from about 2 mg to about 10 mg.

In certain embodiments, the defined amounts of any of the compounds in botanical drug products of the present invention are determined by relying on a combination of tests and controls to ensure the identity, purity, quality, strength, potency, or consistency of the botanical drugs product. These tests and controls include (1) multiple tests for drug substance and drug product (e.g., spectroscopic and/or chromatographic fingerprints, chemical assay of characteristic markers, or biological assay), (2) raw material and process controls (e.g., strict quality controls for the botanical raw materials and adequate in-process controls), and (3) process validation (especially for the drug substance).

These tests can include, but need not be limited to, the following attributes:

Appearance

Chemical identification by spectroscopic and/or chromatographic fingerprints. Examples of spectroscopic methods include ultraviolet, infrared, Fourier transformed infrared, and mass spectroscopy. Examples of chromatographic methods include high performance liquid chromatography (HPLC), HPLC with diode array detection, thin layer chromatography (TLC), 2-dimensional-TLC, and gas chromatography.

Chemical assay (i.e., assay) for active constituents or characteristic markers. If several botanical raw materials are combined to produce a multi-herb substance and a quantitative determination of each individual active constituent or marker is infeasible, a joint determination can be made for several active constituents or markers. When multiple active constituents or markers are known, they should be chemically characterized and their relative amounts should be defined.

Biological assay (when the active chemical constituent(s) are not known or quantifiable), if available.

In certain embodiments, botanical drug products of the present invention are indicated for the treatment of a disorder selected from the group consisting of: abnormal cell growth, a hyperproliferative disorder, an inflammatory disorder, and a combination of two or more of the above. In certain embodiments, the botanical drug products are indicated for the treatment of abnormal cell growth. In certain embodiments, the botanical drug products are indicated for the treatment of a hyperproliferative disorder. In certain embodiments, the botanical drug products are indicated for the treatment of an inflammatory disorder.

In certain embodiments, botanical drug products of the present invention are indicated for the treatment of cancer. In certain embodiments, the cancer treated is selected from the group consisting of: breast cancer, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of two or more of the foregoing cancers.

In certain embodiments, botanical drug products of the present invention are indicated for the treatment of breast cancer. In certain embodiments, the breast cancer includes but is not limited to adenocarcinoma, lobular (small cell) carcinoma, intraductal carcinoma, medullary breast cancer, mucinous breast cancer, tubular breast cancer, papillary breast cancer, Paget's disease, and inflammatory breast cancer.

In another embodiment, the botanical drug products of the present invention are indicated for the treatment of pancreatic cancer. In certain embodiments, the pancreatic cancer includes, but is not limited to, insulinoma, gastrinoma, glucagonoma, vipoma, somatostatin-secreting tumor, and carcinoid or islet cell tumor.

In certain embodiments the invention encompasses methods of administering to a mammal an effective amount of any of the above-described botanical drug products for the treatment of any of the above-described conditions.

In certain embodiments, the botanical drug products of the invention are formulated and administered according to any of the formulations or methods described hereinabove with respect to the pharmaceutical compositions.

5) Methods of Isolating or Concentrating Compounds of the Invention.

In another embodiment, the present invention encompasses methods of isolating or concentrating one or more spirocyclic lignans of formula I from natural materials containing such compounds. In certain embodiments the natural material is a botanical raw material. In some embodiments the botanical raw material is derived from a plant in the genus *Guaiacum*. In certain embodiments, the botanical raw material includes the heartwood of the *Guaiacum* plant. In certain embodiments, the botanical raw material includes the bark of the *Guaiacum* plant.

In certain embodiments, the botanical raw material is derived from a *Guaiacum* species selected from the group consisting of: *G. abilo; G. afrum; G. angustifolium* (Guayacan); *G. arboreum; G. bijugum; G. breynii; G. coulteri* (Guayacan); *G. coulteri* var. *palmeri; G. dubium; G. guatemalense; G. hygrometricum; G. mexicanum; G. microphyllum; G. multijugum; G. officinale* (Commoner Lignum Vitae); *G. palmeri; G. parvifolium; G. planchoni; G. planchonii; G. sanctum* (Guaiacum); *G. sanctum f. angustifolia; G. sanctum lignum; G. sloanei; G. unijugum; G. vertical*; and two or more of the above. In certain embodiments, the *Guaiacum* species comprising the botanical raw material is *Guaiacum officinale*. In certain embodiments, the *Guaiacum* species comprising the botanical raw material is *Guaiacum sanctum*.

In certain embodiments, the isolation or concentration methods of the present invention include the step of analyzing samples resulting from the isolation or concentration steps for the presence of compounds of formula I. In certain embodiments, the compounds of formula I include compounds I-a and/or I-b. In some embodiments, the analyzing step includes measuring the biological activity of the samples. In certain embodiments, the measured biological activity is cytotoxicity. In certain embodiments, the measured biological activity is inhibition of an enzyme. In certain embodiments, the measured biological activity is induction of apoptosis in cell cultures. In other embodiments, the step of analyzing samples for the presence of compounds of formula I., is done by analytical means. In certain embodiments, the analytical means include one or more of HPLC, TLC, GC, magnetic resonance spectroscopy, mass spectroscopy, IR spectroscopy, UV-vis spectroscopy, and titration.

In certain embodiments, the isolation and/or concentration steps are continued until a concentration of the sprirocyclic compounds I exceed a desired threshold.

In some embodiments, the isolation or concentration methods for isolation or concentration of compounds of formula I encompassed by the present invention, include the step of extracting material from a *Guaiacum* plant with an organic solvent. In certain embodiments, the organic solvent is less polar than methanol. In certain embodiments, the organic solvent is less polar than ethanol, or less polar than propanol. In certain embodiments, the method includes extraction of material from a *Guaiacum* plant with a solvent including a halogenated organic solvent. In certain embodiments, the halogenated solvent is selected from the group consisting of: dichloromethane, chloroform, carbon tetrachloride, dichoroethane, trichloroethane, and a mixture of any two or more of these. In certain embodiments, the method includes the step of extracting the material from a *Guaiacum* plant with dichloromethane. In certain embodiments, the method includes the step of extracting the material from a *Guaiacum* plant with chloroform.

In some embodiments, the present invention includes methods comprising the steps of extracting the wood or bark of a plant of a plant in the genus *Guaiacum* with a solvent in which compounds I-a and/or I-b are soluble, then concentrating the solvent extract and washing the concentrate with one or more additional solvents in which compounds I-a and/or I-b are either insoluble, or only sparingly soluble. The latter step may be iteratively repeated with the same or different solvents if desired. The remaining residue that is not dissolved by the washing steps is thereby enriched in compounds I-a and/or I-b relative to the original plant material.

In one embodiment, methods of the present invention include the steps of extracting heartwood from a tree or shrub of the genus *Guaiacum* with a halogenated solvent, concentrating the halogenated solvent to afford a residue, washing the residue concentrate with a protic solvent, and retaining the fraction of the residue not dissolved by the protic solvent. In certain embodiments of this method, the halogenated solvent is selected from the group consisting of dichloromethane, chloroform, dichloroethane, trichloroethane, and a mixture of two or more of these. In certain embodiments of this method, the protic solvent is a lower alcohol.

In certain embodiments, the material isolated by solvent extraction of the *Guaiacum* plant are subjected to further purification by means such as liquid-liquid extraction of organic solvent extracts of *Guaiacum* plants with aqueous solutions of acids, bases, buffers, salts etc. to further enrich the concentration of spirocyles of formula I. In other embodiments, the material isolated by solvent extraction of the *Guaiacum* plant are subjected to further purification by means such as chromatography, distillation, crystallization etc. to further enrich the concentration of spirocyles of formula I. In certain embodiments, the further purification steps include contacting the extracts with solids such as ion exchange resins, functionalized resins, inorganic adsorbants.

In other embodiments, methods of the present invention include the step of pulverizing the heartwood of a *Guaiacum* tree into a fine powder, and incorporating the powder into a nutraceutical, or botanical drug product.

In certain embodiments, methods of the present invention include contacting the powdered heartwood of a *Guaiacum* tree with hot water for a period of time and then evaporating the mixture to provide a solid. In certain embodiments the hot water is boiling water. In certain embodiments, the woor powder is contacted with the hot water for a period of time ranging from about 15 minutes to about 24 hours. In certain embodiments, the wood powder is contacted with the hot water for a period of about 1 hour to about 4 hours, for example, for about 1 hour, 1.5 hours, 2, hours, 3, hours, 4 hours, 6 hours, 8 hours, 12 hours, or about 24 hours.

In certain embodiments the mixture of water and *Guaiacum* heartwood is then lyophilized to yield a residue containing the wood powder and any residue dissolved in the water. In certain embodiments, the mixture is extracted wth organic solvents. In other embodiments, the mixture is filtered and the wood powder is further extracted with organic solvents. In other embodiments the mixture is filtered and the aqueous filtrate is dried to afford a residue.

In certain embodiments, the present invention encompasses nutraceutical or botanical drug products comprising one or more of the products resulting from the above-described methods.

The compounds of formula Ia and Ib are purified resulting from the isolation thereof as described hereinabove. In an embodiment of the present invention, when the compounds of formula Ia or Ib are added to a composition, they are as purified compounds, for example, each contains less than about 15% impurities by weight, and in another embodiment, less than about 10% impurities by weight, and in another embodiment, less than about 5% impurities by weight and in another embodiment, less than about 1% impurities by weight and in a further embodiment, less than about 0.5% impurities by weight. If the compounds of formula Ia or Ib do not have the requisite impurity, each can be made more pure by utilizing techniques known to ordinary skill in the art, such as by chromatography, including HPLC, crystallization, and the like. As defined herein, the term "substantially pure" refers to a compound of formula Ia or Ib containing less than about 15% impurities by weight.

The compounds of formula Ia and Ib, when added to a composition, may not only be substantially pure, but in addition or alternatively, maybe substantially enantiopure, i.e., containing only one stereoisomer and substantially free of other stereoisomers. In one embodiment, the compounds of formula Ia or Ib contains less than about 15% by weight of stereoisomers and in another embodiment less than about 10% by weight of stereoisomers and in another embodiment less than about 5% by weight of stereoisomers and in a further embodiment, less than about 1% by weight of other stereoisomers. The compounds of formula Ia and Ib may be made in entiopure by techniques known to the skilled artisan.

EXAMPLES

Isolation and Identification of Compounds of the Invention

This section describes the bioassay guided fractionation of material from trees of the *Guaiacum* genus and subsequent chemical identification using multidimensional spectroscopic methods.

Phytochemical analysis resulted in the isolation of two novel spirocyclic lignans I-a and I-b along with three known diarylterahydrofuran-type lignans, nectandrin B (I-c), isonectandrin B (I-c) and machilin I (I-d); and one known diarylbutane-type lignan, meso-dihydroguaiaretic acid (I-e). The structures of the new compounds were identified by spectroscopic analysis, including 2D NMR and mass spectroscopy. The structures of the known compounds were identified by multidimensional NMR and confirmed by comparing the physical and spectral data with those from the literature.

Chemicals

HPLC-grade water was produced by reverse osmosis followed by distillation. HPLC solvents; MeOH and acetonitrile, and sephadex LH-20 were obtained from Sigma-Aldrich (Sigma-Aldrich, Vienna, Austria). Silica gel (KG60, 40-63 µm) and precoated TLC plates (silica gel KG60-F254) were obtained from Merck (Darmstadt, Germany). For thin layer chromatography, compounds were visualized using UV light and/or vanillin/sulfuric acid reagent. All chemicals used were of highest purity commercially available.

Instrumentation

Nuclear magnetic resonance (NMR) spectra were obtained on a Bruker DRX-300 at 300 MHz ($^1$H) and 75 MHz ($^{13}$C) for 2D and 1D measurements. $^{13}$C DEPT, $^1$H-$^1$H COSY, HSQC and HMBC NMR spectra were obtained using standard Bruker pulse sequences. An INOVA 500 was also used for obtaining 2D and 1D measurements at 500 MHz ($^1$H) and 125 MHz ($^{13}$C). Mass spectrometry was recorded on a Finnigan MAT 95S (EI_MS). MS parameters; ESIMS data was obtained with a Finnigan MAT SSQ 7000 (Finnigan MAT, San Jose, Calif. USA) equipped with a Digital DEC 3000 data station (Digital Equipment Corp, Maryland, Mass., USA) in positive and negative modus. The LC flow split was 1:5 the dry temp was 300° C. In the negative mode the spray voltage was −4.7 kV and in the positive mode it was 5.1 kV. The CID (collision induced dissociation was zero in both cases, the nebulizer was 30 psi, and the dry gas was 8 L/min. The MS data was acquired in the negative mode over a range of 100-10000 Da.

Analytical HPLC employed an HP 1090 system (Aligent, Waldbronn, Germany) equipped with an Agilent 1100 photodiode array detector, autosampler, and column thermostat. The LC was equipped with a Phenomenex Hydro column RP 4 μm (150 μm×4.6 μm); temp 45.0° C., flow rate 1.0 ml/min, with an injection volume of 10 μl and three mobile phases; A. 42.0% MeOH, B, 3.0% ACN, and C, 55.0% water were utilized. The gradient was employed as follows: start 0%, 15 min 42% A, 3.0% B, and 55.0% C; 25 min 65% A, 5% B, and 30% C; 35 min 65% A 33% B, and 2% C, stop time was 45 min and post time was 10 min. For semi-preparative HPLC, a Dionex system with a P580 pump, ASI-100 autosampler, UVD 170U detector and Gibson 206 fraction collector was utilized. A preparative reverse phase Phenomenex Aqua column 5μ C18 125 (250×10.00 mm) was employed.

Apoptotic Assays

Apoptosis was evaluated against human breast cancer cell line MD-MBA-231. Cells were maintained in RPMI 1640 medium (PAA Laboratories GmbH, Teddington Middlesex, UK) supplemented with 10% heat-inactivated tetracycline-free fetal calf serum (PAA Laboratories) and 2 mM L-glutamine, 100 units/ml penicillin, and 100 μg/ml streptomycin (Gibco, Grand Island, N.Y.). Cells were propagated and cultured at 37° C. in a 100% relative humidified atmosphere consisting of 5% C02 and 95% air. Cells were trypsinized with 0.05% Trypsin-0.2% EDTA (w/v) solution.

The bioactivity-guided isolation of the compounds was performed using percent apoptosis in human breast cancer cells (cell line MD-MBA-231) as the reporter. Cells were seeded in a standard 24-well microtiter plate at a density of $1.5 \times 10^4$ cells/well in 3-μl tissue culture medium. After a 24-h incubation period cells were treated with individual fractions from the wood of *Guaiacum officinale* L. Test compounds were mixed in solution using DMSO as vehicle (10 μg extract/1 ml DMSO), at 30 μl. Following a 48-h incubation period, the induction of apoptosis in cell cultures was analyzed by fluorescence-activated cell sorter (FACS Caliber Becton Dickinson, San Jose, Calif.), double staining with Annexin V/Propidium iodide.

Plant Material

*Guaiacum officinale* L. (Zygophyllaceae) branches approximately 10 mm to 20 mm in diameter were stripped of their bark and stored in separate containers. They were cut into small pieces, air dried, and ground. A voucher specimen was deposited at the L. H. Bailey Hortorium Herbarium (BH) at Cornell University, Ithaca, N.Y., United States, under specimen accession number #1883 (2000).

Figure 5:
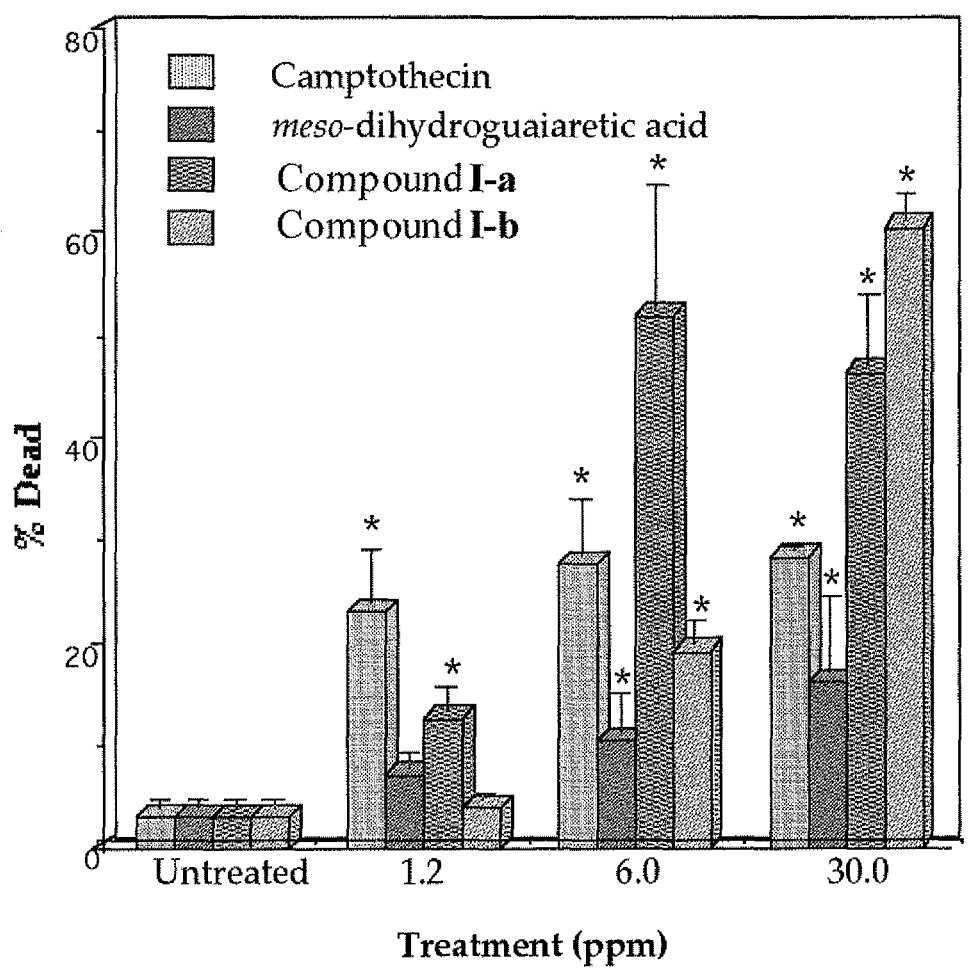
FIG. 5 shows the effect of lignans I-a, I-b, and meso-dihydroguaiaretic acid on the induction of late stage apoptosis. Cells were treated with varying doses at 24 hr. in human breast cancer cell line MD-MBA 231. Analysis was determined by FACS, Annexin V_FITC. Camptothecin was used as a positive control. Treatment means with an * are statistically different from the control group at the 5% level according to Fisher's Projected LSD (SuperANOVA 1989).

The dried and powdered wood material (500 g) was extracted exhaustively with dichloromethane (DCM) for three days in a soxhlet apparatus followed by extraction with MeOH. The DCM extract yielded 286 g and was analyzed with HPLC and chromatographed over sephadex LH20, using DCM 85% to acetone 15% proportions as eluent. The fractions were combined according to their TLC profiles to yield 19 pools (F001-F019). Fractions (F013 and F014, 476.35 mg) were combined based on their HPLC profiles and were chromatographed over sephadex LH-20, using 100% acetone. Eight pools (F013-1-F013-8) based on their TLC profiles were collected. F013-6 was subject to semi-preparative HPLC because it was a major peak in the crude analytical DCM HPLC sample. The semi-preparatory HPLC conditions were isocratic with a run time of 40 minutes at 70% methanol: water, 1.5 flow rate to yield 15 pools (F013-6a-F013-6r). The most active fractions in decreasing order were (F013-6P, 5.3 mg>F013-6O, 37 mg>F013-6F, 2.0 mg>F013-6H, 5.28 mg>F013-6D, 2.9 mg), refer to (FIG. 5.1). The above fractions were further analyzed for spectral data.

The bioactivity was found to be the highest in fractions F006 and F008-F017. Fraction F008, with a yield of 507.29 mg, was further chromatographed, due to its semi pure HPLC profile, over sephadex LH-20, using 100% acetone to yield 10 pools (F008-1-F008-10) based on their TLC profiles. Semi-preparative HPLC followed on F008-7; yield 266.67 mg, because it was one of the major peaks in the crude analytical DCM HPLC sample.

Figure 13:
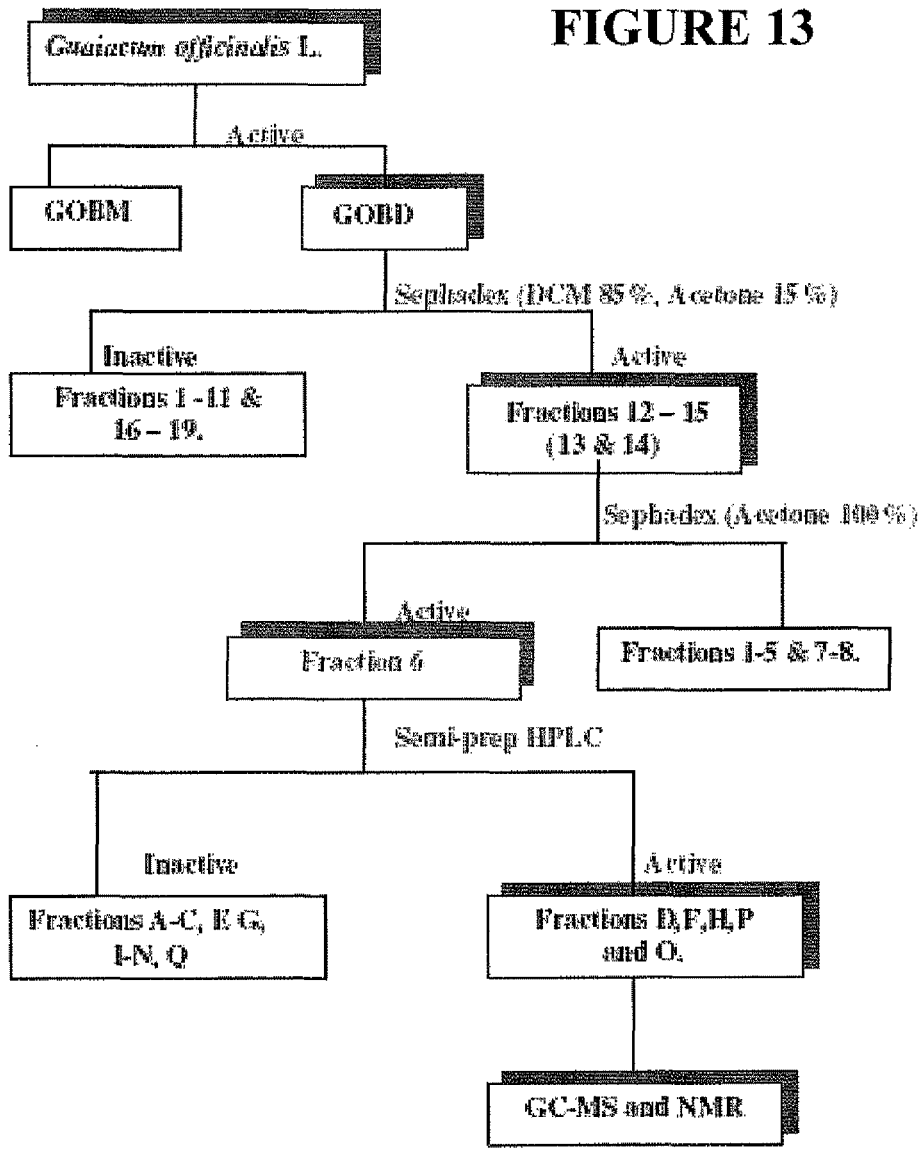
FIG. 13 shows bioassay guided fractionation diagram of compounds I-a and I-b. The semi-preparatory conditions were isocratic with a run time of 35 minutes at 70% methanol: water to yield 13 pools (F008-7a-F008-7m). The most active fractions F008-7j and F008-7m were further analyzed for spectral data using LC-MS and multidimensional NMR. Their yields were 51.3 mg and 55.9 mg, respectively. Fractions (F005 and F006, 287.44 mg) were combined based on their HPLC profiles and were subjected to semi-preparatory conditions with an isocratic run time of 30 minutes at 80% methanol: water, with a 1.5 flow rate. They were isolated because they contained two of the major peaks in the crude DCM HPLC and their activity contrasted each other. F0005 displayed low activity and F0006 displayed high activity. Fraction F0005 was further fractionated and led to the collection of eleven fractions (F005-1-F005-11). Fractions (F005-3, 4.28 mg), (F005-4, 6.84 mg), (F005-6, 9.88 mg) and (F005-10, 164.38) were pure compounds based on their HPLC profiles and were subject to further analysis for spectral data using LC-MS and multidimensional NMR. The isolation tree for the above lignans, excluding F005-6 and F0005-10, which underwent the same conditions are shown in (FIG. 14).
Figure 14:
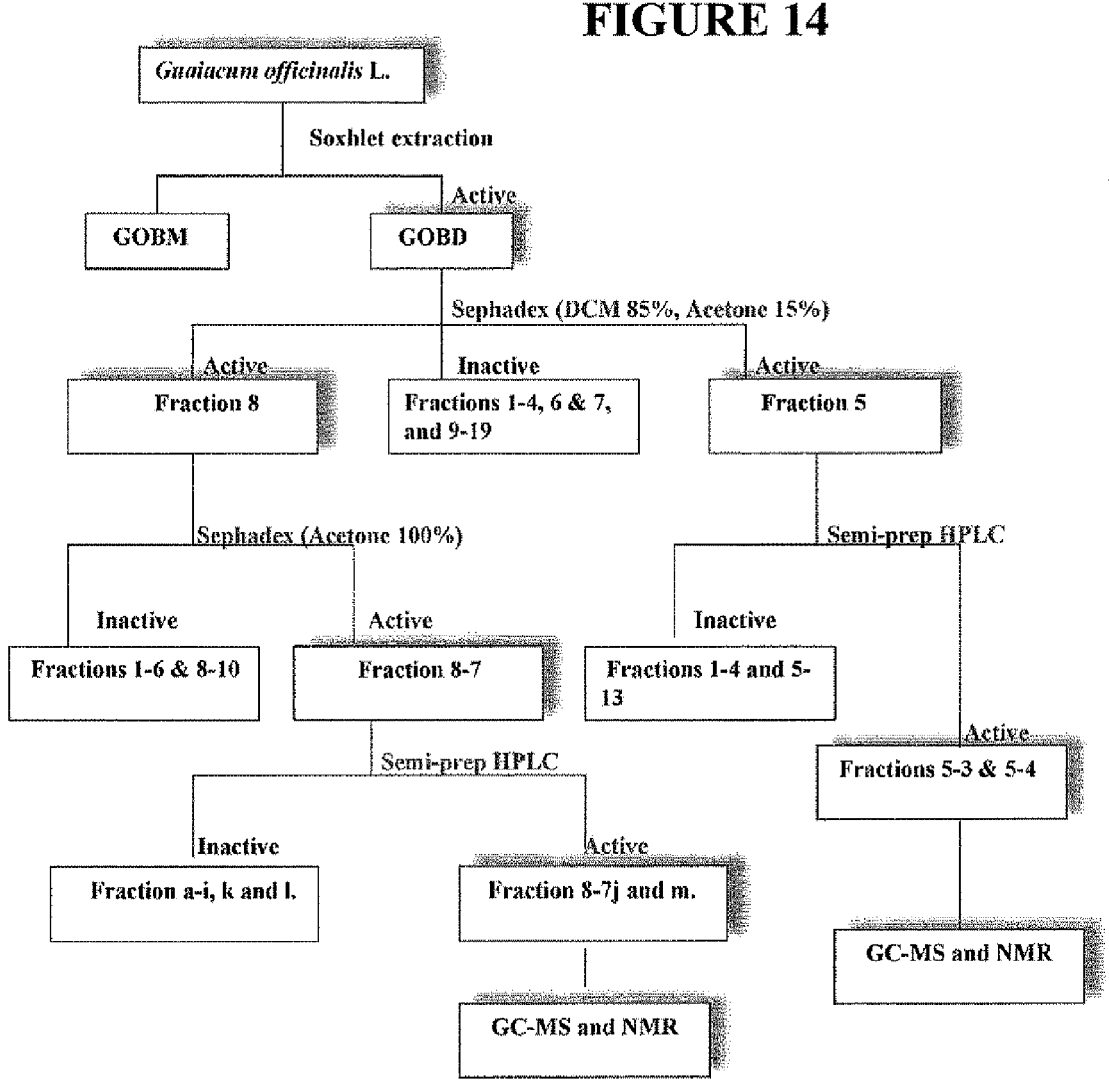
FIG. 14 shows the bioassay guided fractionation diagram of compounds I-c, I-d, I-e, and I-f.

FIG. 13 shows bioassay guided fractionation diagram of compounds I-a and I-b from fraction F008-7. The semi-preparatory conditions were isocratic with a run time of 35 minutes at 70% methanol: water to yield 13 pools (F008-7a F008-7m). The most active fractions F008-7j and F008-7m were further analyzed for spectral data using LC-MS and multidimensional NMR. Their yields were 51.3 mg and 55.9 mg, respectively. Fractions (F005 and F006, 287.44 mg) were combined based on their HPLC profiles and were subjected to semi-preparatory conditions with an isocratic run time of 30 minutes at 80% methanol: water, with a 1.5 flow rate. They were isolated because they contained two of the major peaks in the crude DCM HPLC and their activity contrasted each other. F0005 displayed low activity and F0006 displayed high activity. Fraction F0005 was further fractionated and led to the collection of eleven fractions (F005-1-F005-11). Fractions (F005-3, 4.28 mg), (F005-4, 6.84 mg), (F005-6, 9.88 mg) and (F005-10, 164.38) were pure compounds based on their HPLC profiles and were subject to further analysis for spectral data using LC-MS and multidimensional NMR. The isolation tree for the above lignans, excluding F005-6 and F0005-10, which underwent the same conditions are shown in (FIG. 14).

Results

Biological-guided fractionation of the DCM extract of *Guaiacum officinale* L. led to the isolation of 10 compounds of which the chemical structures of six were identified. NMR analysis revealed two novel spirocyclic lignans I-a and I-b, three diarylterahydrofuran-type lignans, nectandrin B (I-c), isonectandrin B (I-d), and machilin I (I-e); one diarylbutane-type lignan, meso-dihydroguaiaretic acid (I-f). The structures of the compounds were identified by multidimensional NMR and confirmed by comparing the physical and spectra data spectra data with those from the literature (NMR, and MS).

Identification of Spirocyclic Lignans I-a and I-b

Figure 15:
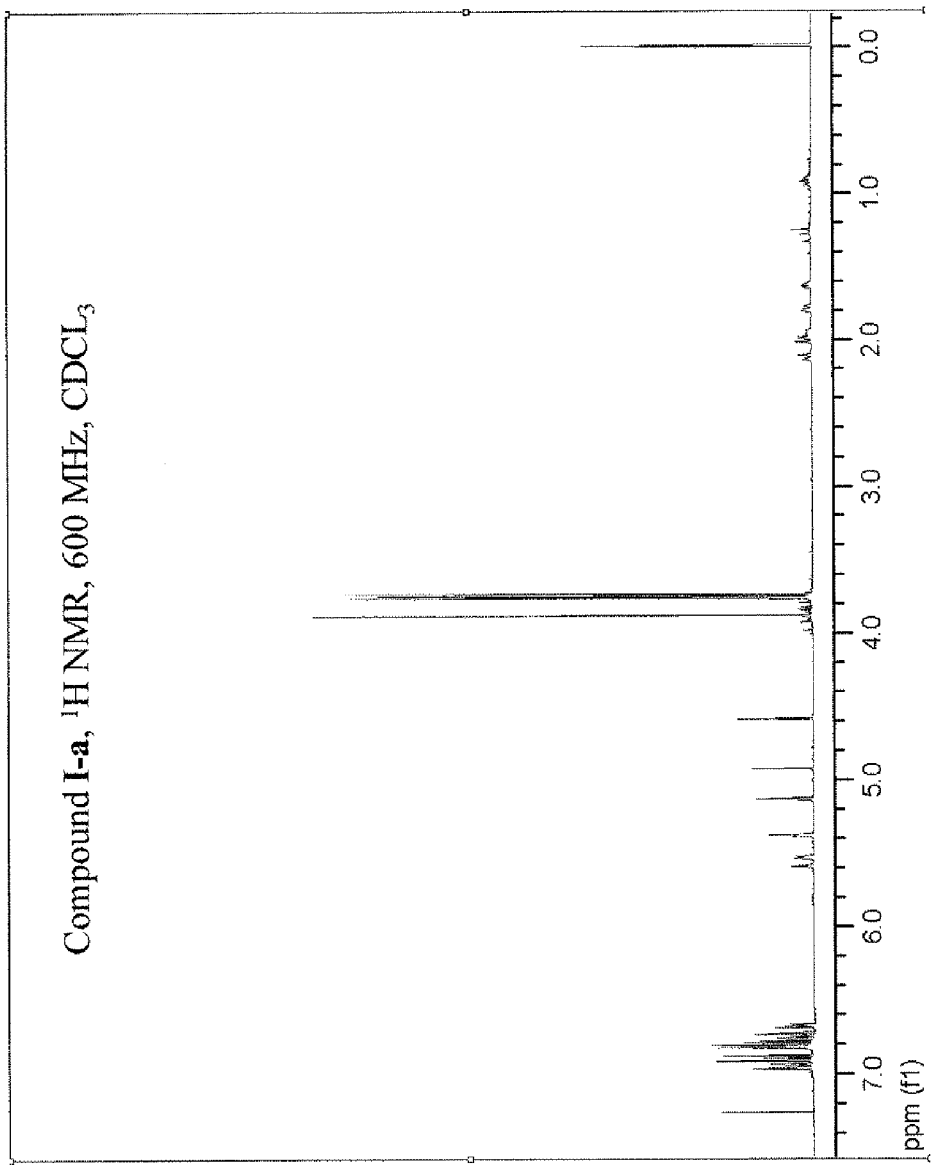
FIG. 15 shows the $H^1$ NMR spectrum of compound I-a.

Analysis of the dqfCOSY and HMQC spectra of compound I-a isolated from *Guaiacum officinale* L. revealed proton spin systems representing four 1,3,4,-trisubstituted benzene rings, four methines at $\delta_H$ 5.58, 5.53, 5.38, and 4.58 ppm, an olefinic methylene group at $\delta_H$ 5.13 and 4.92 ppm, four methoxy groups at $\delta_H$ 3.88, 3.76, 3.75, and 3.73 ppm and a complex spin system composed of six aliphatic methylene protons (Table E1 and FIG. 15). High resolution FAB mass spectroscopy revealed a molecular formula of $C_{40}H_{40}O_{10}$ (m/z observed 680.7521, calculated for $C_{40}H_{40}O_{10}$, 680.7397).

HMBC correlations of the aromatic protons and the methoxy groups indicated the presence of four 4-hydroxy-3-methoxyphenyl groups in the structure of compound I-a. Additional HMBC correlations of the methine protons 1-H, 3-H, 8-H, and 10-H and the protons in positions 2 and 6 of the four aromatic ring systems positioned these methine groups in the 1-positions of the aromatic rings. HMBC-correlations of the olefinic methylene protons with C-3, C-4, and C-5 in conjunction with correlations of 1-H and 3-H with C-4 and C-5 establish connectivity of C-1 and C-3 through C-5. Correlations of 13-H and 6-H with C-1, C-4, and C-5 position these aliphatic methylene groups next to C-5, whereas correlations of 6-H, 12-H, and 13-H indicate that carbons C-7 and C-11 form a tetra-substituted double bond as part of a 6-membered ring also incorporating C-5, C-6, C-12, and C-13. Finally, correlations of 8-H and 10-H with the carbons of the 6-membered ring allowed placing the respective phenyl-substituted methine groups as shown. The presence of the two furane rings follows from the results of the mass spectrometric analysis, which indicate the presence of two oxygen atoms in addition to those attached to the aromatic rings, and from the chemical shift values of the protons and carbons of the four methine groups that are part of the furan rings. The presence of these furans is further supported by strong NOE's between 1-H and 3-H, as observed in ROESY and NOESY spectra. The NOE's between 1-H and 3-H also define the relative orientation of the two phenyl substituents on this ring as cis. NOE's between the protons 6-H and 1-H as well as the absence of NOE's between the protons 13-H with either 1-H or 3-H indicate cis-orientation for C-6 with respect to the two phenyl groups attached to C-1 and C-3 and thus trans-orientation for C-13. Lastly, NOE's of protons 8-H and 10-H with one of the protons of the methylene group attached to C-4 indicate that 8-H and 10-H are cis to each other and on the same side of the bicyclus as C-4.

TABLE E1

$^1$H (600 MHz) and $^{13}$C (151 MHz) NMR spectroscopic data of I-a

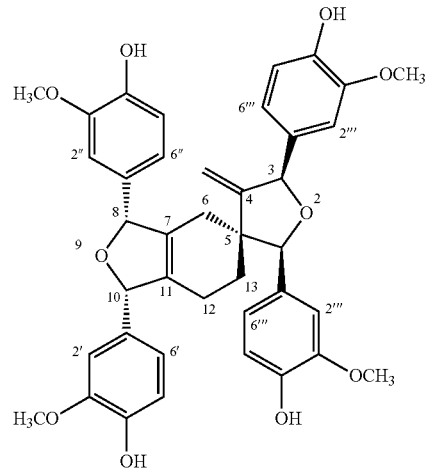 [SMILES: C=C1[C@@H](c2ccc(O)c(OC)c2)O[C@@H](c2ccc(O)c(OC)c2)[C@@]12CCC1=C(C2)[C@@H](c2ccc(O)c(OC)c2)O[C@H]1c1ccc(O)c(OC)c1]

| Carbon No. | δ, ppm | Proton No. | δ, ppm | $J_{HH}$, Hz | NOESY Correlations | HMBC Correlations |
|---|---|---|---|---|---|---|
| C-1 | 87.8 | 1-H | 4.58 | | 3-H, 6-H$_\alpha$, 6-H$_\beta$, 2'''-H, 6'''-H | 4, 5, 6, 13, 1''', 6''' 2''' |
| C-3 | 82.7 | 3-H | 5.38 | $J_{3-H,4-CH\alpha H\beta}$ = $J_{3-H,4-CH\alpha H\beta}$ = 2.3 | 1-H, 2''''-H, 6''''-H 4-CH$_\alpha$H$_\beta$ | 4, 4-CH$_2$, 5 (wk), 1'''', 2'''', 6'''' |
| C-4 | 157.6 | | | | | |
| 4-CH$_2$ | 106.9 | 4-CH$_\alpha$H$_\beta$ | 5.13 | | 6-H$_\beta$, 8-H, 10-H, 12-H$_\alpha$, 4-CH$_\alpha$H$_\beta$ | 3, 4, 5, 13 (wk), 1'''' (wk) |
| | | 4-CH$_\alpha$H$_\beta$ | 4.92 | | 3-H, 2''''-H, 6''''-H, 4-CH$_\alpha$H$_\beta$ | 3, 4, 5, 13 (wk), 1'''' (wk) |
| C-5 | 47.6 | | | | | |
| C-6 | 30.1 | 6-H$_\alpha$ | 2.12 | $J_{6-H\alpha,6-H\beta}$ = 16.8, $J_{6-H\alpha,12-H\alpha}$ = 3, $J_{6-H\alpha,12-H\beta}$ = 1.5 | 1-H, 13-H$_\beta$, 2''-H, 6''-H | 1, 4, 5, 7, 11 |
| | | 6-H$_\beta$ | 2.00 | $J_{6-H\beta,12-H\alpha}$ = 2.5, $J_{6-H\beta,12-H\beta}$ < 1, $J_{6-H\beta,13-H\alpha}$ = 1 | 1-H, 8-H, 12-H$_\beta$, 4-CH$_\alpha$H$_\beta$ | 4, 5, 7, 8, 11, 13 |
| C-7 | 135.9 | | | | | |
| C-8 | 88.9 | 8-H | 5.58 | $J_{8-H,10-H}$ = 3, $J_{8-H,6-H\alpha}$ = 1.5, $J_{8-H,6-H\beta}$ = 1 | 6-H$_\beta$, 4-CH$_\alpha$H$_\beta$, 2''-H, 6''-H | 7, 11, 1'', 2'', 6'' |
| C-10 | 88.5 | 10-H | 5.53 | $J_{10-H,6-H\alpha}$ = 2.3, $J_{10-H,6-H\beta}$ = 3 | 12-H$_\alpha$, 12-H$_\beta$, 4-CH$_\alpha$H$_\beta$, 2'-H, 6'-H$_\beta$ | 7, 11, 1', 2', 6' |
| C-11 | 132.8 | | | | | |
| C-12 | 18.5 | 12-H$_\alpha$ | 1.96 | $J_{12-H\alpha,12-H\beta}$ = 17.3, $J_{12-H\alpha,13-H\alpha}$ = 5.6, $J_{12-H\alpha,13-H\beta}$ = 10.9 | 10-H, 4-CH$_\alpha$H$_\beta$, 12-H$_\beta$, 13-H$_\alpha$, 2''''-H, 6''''-H | |
| | | 12-H$_\beta$ | 1.78 | $J_{12-H\beta,13-H\alpha}$ = 2.5, $J_{12-H\beta,13-H\beta}$ = 5.5 | 10-H (wk), 12-H$_\alpha$, 13-H$_\alpha$ (wk), 13-H$_\beta$, 2'-H, 6'-H | 5, 7, 10 (wk), 11, 13 |
| C-13 | 26.1 | 13-H$_\alpha$ | 1.62 | $J_{13-H\alpha,13-H\beta}$ = 13.7 | 4-CH$_\alpha$H$_\beta$, 12-H$_\alpha$, 12-H$_\beta$, 13-H$_\beta$, 2'''-H, 6'''-H, 2''''-H, 6''''-H | 1, 4, 5, 6, 11, 12 |
| | | 13-H$_\beta$ | 0.91 | | 1-H (wk), 6-H$_\alpha$, 12-H$_\beta$, 13-H$_\alpha$, 2'-H, 6'-H, 2''-H, 6''-H | 1, 4, 5, 6, 11, 12 |

TABLE E1-continued

| C-1' | 132.07 | | | | | |
|---|---|---|---|---|---|---|
| C-2' | 109.92 | 2'-H | 6.73 | $J_{2'-H,6'-H} = 2.0$ | 10-H, OCH$_3$', 12-H$_\beta$, 13-H$_\beta$ | 1', 3', 4', 6', 10 |
| C-3' | 146.49 | | | | | |
| C-4' | 145.42 | | | | | |
| C-5' | 113.91 | 5'-H | 6.81 | $J_{5'-H,6'-H} = 8.0$ | | 2', 3', 4', 6' |
| C-6' | 119.77 | 6'-H | 6.67 | | 10-H, 12-H$_\beta$, 13-H$_\beta$ | 2', 3' (wk), 4', 5', 10 |
| C-1" | 132.07 | | | | | |
| C-2" | 110.28 | 2"-H | 6.79 | $J_{2"-H,6"-H} = 2.0$ | 6-H$_\alpha$, 6-H$_\beta$, 8-H, 13-H$_\beta$ (wk), OCH$_3$" | 1", 3", 4", 6", 8 |

Figure 16:
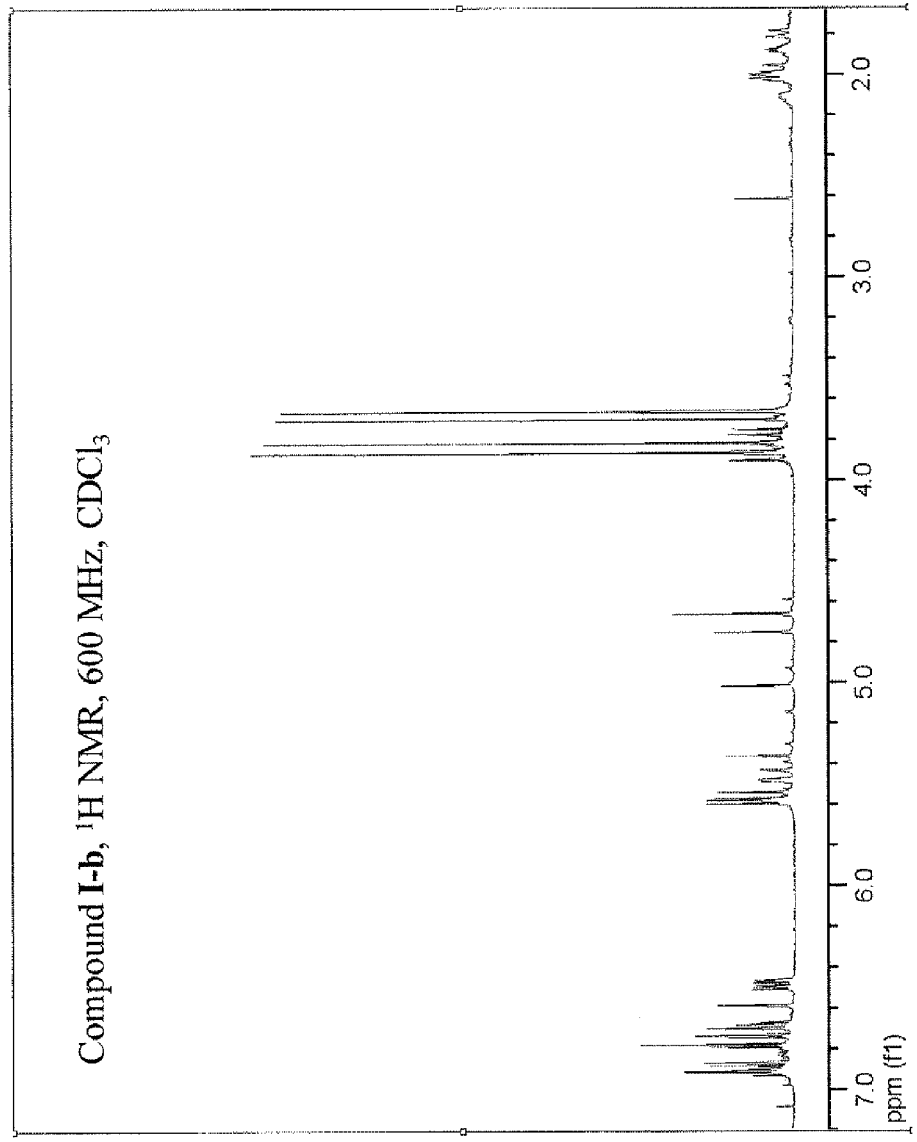
FIG. 16 shows the $H^1$ NMR spectrum of compound I-b.

$C_{40}H_{40}O_{10}$ (m/z observed 680.7521, calculated 680.7397)
wk weak HMBC or ROSEY correlations The NMR spectroscopic data of compound I-b are very similar to those of compound I-a (Table E-2 and FIG. 16), and the two compounds share the same molecular formula, which suggested that I-b is a diastereomer of I-a. Analysis of the ROESY spectrum obtained for I-b showed a strong NOE between the protons at C-13 and protons 1-H and 3-H, whereas no NOE was observed for the protons at C-6 and 1-H and 3-H, which indicated that the relative configuration of C-5 in I-b is inverted as compared to I-a. Full analysis of the NMR spectroscopic data of I-b showed that the structures of I-a and I-b are identical except for the relative configuration at C-4 as well as perhaps their absolute configuration.

TABLE E2

$^1$H (600 MHz) and $^{13}$C (151 MHz) NMR spectroscopic data of I-b

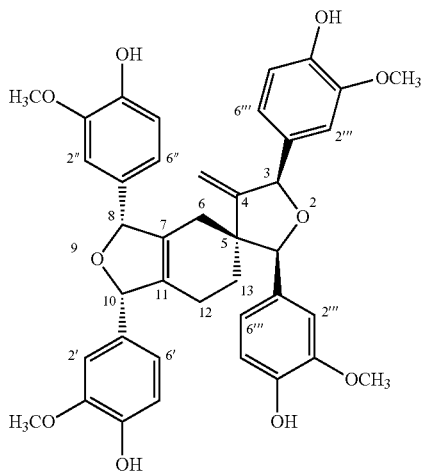 [SMILES: C=C1[C@@H](c2ccc(O)c(OC)c2)O[C@@H](c2ccc(O)c(OC)c2)[C@]12CCC1=C(C2)[C@@H](c2ccc(O)c(OC)c2)O[C@H]1c1ccc(O)c(OC)c1]

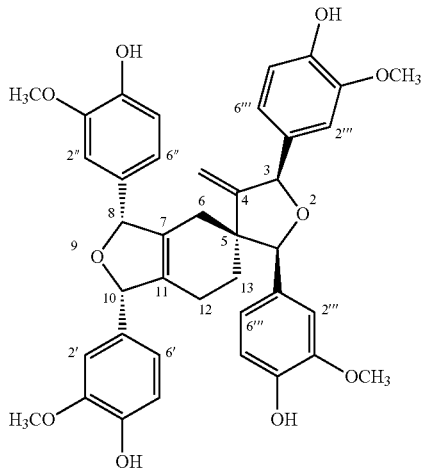 [SMILES: C=C1[C@@H](c2ccc(O)c(OC)c2)O[C@@H](c2ccc(O)c(OC)c2)[C@]12CCC1=C(C2)[C@@H](c2ccc(O)c(OC)c2)O[C@H]1c1ccc(O)c(OC)c1]

| Carbon No. | δ, ppm | Proton No. | δ, ppm | J Hz | ROESY Correlations | HMBC Correlations |
|---|---|---|---|---|---|---|
| C-1 | 82.20 | 1-H | 5.36 | t; 2.16, 2.16 | 2"", 3, 13β, 12β (wk), 10 | 4, 1"", 6"", 2"" vinyl α |

TABLE E2-continued

| | | | | | | |
|---|---|---|---|---|---|---|
| C-3 | 89.42 | 3-H | 4.66 | s | 6''', 1, 13β, 12β | 4, 1''', 6''', 2''' |
| | | | | | | 1 (wk), 5, 6, 13 |
| C-4 | 159.30 | | | | | |
| C-5 | 47.6 | | | | | |
| C-6 | 32.70 | 6-H$_\alpha$ | 1.80 | | 6β, vinyl α, 12β | |
| | | 6-H$_\beta$ | 1.97 | | 2''', 6β | |
| C-7 | 133.25 | | | | | |
| C-8 | 88.95 | 8-H | 5.43 | | 2,' 6', 6α | 3', 4', 5' |
| C-10 | 88.272 | 10-H | 5.60 | | 2'', 6'' | 3'', 4'', 5'' |
| C-11 | 133.45 | | | | | |
| C-12 | 19.81 | 12-H$_\alpha$ | 2.00 | | 12β | |
| | | 12-H$_\beta$ | 1.87 | | 3, 12α, 13α | 7, 5, 13, 12 |
| C-13 | 30.18 | 13-H$_\alpha$ | 2.12 | | | |
| | | 13-H$_\beta$ | 2.010 | | 1, 12β, vinyl α, 3, 13α | |
| vinyl | 106.87 | 14-H$_\alpha$ | 5.02 | d; 2.44 | vinyl β, 6α, 13β, 13α | 1, 5 |
| | | 14-H$_\beta$ | 4.75 | d; 2.16 | 1, 2'''', vinyl α, 3 | 4, 1, 5 |
| C-1' | 132.54 | | | | | |
| C-2' | 110.36 | C-2'-H$_\alpha$ | 6.59 | d; 1.80 | OCH$_3$', 8 | 3', 4', 1', 6', 8 |
| C-3' | 148.83 | | | | | |
| C-4' | 145.42 | | | | | |
| C-5' | 114.26 | C-5'-H$_\alpha$ | 6.78 | | 6', 10, 12α | 3', 4', 1' |
| C-6' | 120.15 | C-6'-H$_\alpha$ | 6.50 | dd; 8.10, 1.81 | 8, 6β | 4', 2', 8 |
| C-1'' | 132.65 | | | | | |
| C-2'' | 110.61 | C-2''-H$_\alpha$ | 6.78 | d; 2.18 | 10, OCH$_3$ | 4'', 1'', 6'', 5'' (wk), 8 |
| C-3'' | 146.83 | | | | | |
| C-4'' | 145.77 | | | | | |
| C-5'' | 114.43 | C-5''-H$_\alpha$ | 6.87 | d; 8.06 | 6'' | 3'', 4'', 1'' |
| C-6'' | 120.65 | C-6''-H$_\alpha$ | 6.47 | dd; 8.08, 1.85 | 10, 12α | 4'', 2'', 8 |
| C-1''' | 128.557 | | | | | |
| C-2''' | 110.02 | C-2'''-H$_\alpha$ | 6.70 | d; 1.74 | 3, OCH$_3$''', 6β, 6α (wk) | 3''', 4''', 6''', 3 |
| C-3''' | 146.25 | | | | | |
| C-4''' | 145.43 | | | | | |
| C-5''' | 114.01 | C-5'''-H$_\alpha$ | 6.74 | d, 8.05 | 3, OCH$_3$''', 6β | 3''', 1''' |
| C-6''' | 120.48 | C-6'''-H$_\alpha$ | 6.68 | dd; 8.10, 1.80 | 3, 6β, 6α (wk) OCH$_3$''' | 4''', 2''', 3 |
| C-1'''' | 133.35 | | | | | |
| C-2'''' | 110.27 | C-2''''-H$_\alpha$ | 6.90 | | 1, OCH$_3$'''', vinyl β (wk) | 3'''', 4'''', 6'''', 1 |
| C-3'''' | 146.85 | | | | | |
| C-4'''' | 145.536 | | | | | |
| C-5'''' | 114.424 | C-5''''-H$_\alpha$ | 6.93 | d; 2.72 | OCH$_3$'''' | 3'''', 4'''', 1'''', 6'''' (wk) |
| C-6'''' | 120.48 | C-6''''-H$_\alpha$ | 6.90 | dd; 9.66 | vinyl β, OCH$_3$'''', 6α, 6β | 3'''', 4'''', 2'''', 1 |
| OCH$_3$' | | C'-H$_\alpha$ | 3.70 | s | 2' | |
| OCH$_3$'' | | C'-H$_\alpha$ | 3.82 | s | 2'' | |
| OCH$_3$''' | 145.90 | C'-H$_\alpha$ | 3.66 | s | 2''' | |
| OCH$_3$'''' | | C'''-H$_\alpha$ | 3.87 | s | 2'''' | |
| OH | | | 5.43 | s (broad) | | |
| OH | | | 5.48 | s (broad) | | |

$C_{40}H_{40}O_{10}$ (m/z observed 680.7521, calculated 680.7397)

wk weak HMBC or ROSEY correlations

Diaryltetrahydrofuran Lignans Compounds I-c, I-d, and I-e

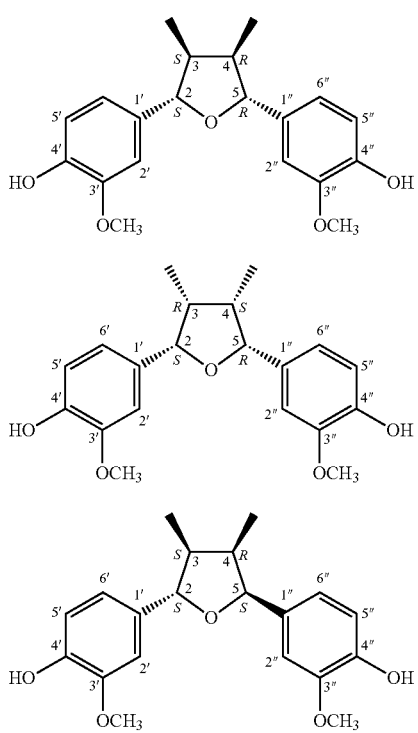

The $^1$H and $^{13}$C NMR spectra of fractions F008-7m and F005-4 were identical suggesting that they are the same compound and thus will correspond to compound I-c for further discussion. The $^1$H NMR spectrum of compound I-c showing the presence of 12 hydrogen and 10 carbon signals, suggesting the symmetric nature of the structures (Table E3). The molecular ion peak at m/z 344 in the mass spectrum confirmed the following molecular formula ($C_{20}H_{24}O_5$) for both compounds. The $^1$H NMR spectrum for showed two 1,3,4,-trisubstituted benzene rings with protons at δ 6.95 (d, J=4.8 Hz), 6.91 (d, J=2.8 Hz), and singlet at δ 6.88, a wide peak for a hydroxyl group at δ 5.59, a methine at δ 4.49 (d, J=6.34 Hz), a downfield methoxy singlet at δ 3.88 displaying a HMBC correlation to the aromatic ring, another methine displayed as a multiplet at δ 2.33, in addition to a methyl at δ 1.03 (d, J=6.57 Hz), refer to (Appendix B6 and Appendix B7). The $^{13}$C, DEPT 1 and DEPT 2 NMR spectra showed six aromatic carbons, two oxygenated aromatic carbons at δ 146.6 and δ 145.1, a non-protonated aromatic carbon at δ 134.2, three proton coupled aromatic carbons at δ 119.2, 114.3 and 109.4, an oxymethine at δ 87.2, another oxygenated carbon at δ 55.9, another upfield methine at δ 44.2 and a methyl carbon at δ 13.0, (Appendix B8, B9, and B10). The missing carbon signals at δ 146.6, 145.1, and 134.2 in the DEPT 1 and 2 and the HSQC spectra supported the 1,3,4,-trisubstituted benzene ring suggesting the OH and MeO substituents were at positions 3 and 4 of the aromatic ring. The intensity of the signals at C2, C5, and C6 confirmed the positions. In addition, the missing signals in DEPT 2 at δ 55.9 and 13.0 supported that these carbons are methylated, one giving rise to the methoxy reported at the lower frequency due to the deshielding effect of the oxygen. The HMBC data suggested a tetrahydrofuran ring methylated at positions 3 and 4 of ring A. The protons of the methyl at δ 1.03 intersect three cross peaks and show a two bond HMBC correlation to C-3 which is bonded to C-2 and C-1'. H-3 shows a two bond correlation to the methyl protons and a 2-bond HMBC correlations to C-2 and another correlation to C-1. In the HMBC spectrum H-2 correlates with the methyl protons and the aromatic C-1', C-2' and C-6' together further establish the 3,4-dimethyl-2,5-furanaryl ring system, (Appendix B12). Compound I-c clearly shows a trans relationship between the vicinal Me and aryl groups at H3H2 and H4H5, as reported in previous studies (Rao, 1982, Herath et al, 1996; and Prasad et al, 1995). The $^{13}$C-NMR supported this assessment with upfield shifts in C-2 (δ 87.2 to 82.9), C-3 (δ 44.3 to 41.6) and the methyl carbon (δ 13.0 to 11.9). In addition, compound 3 showed no measurable rotation and this confirmed the symmetry of the molecule. Therefore the structure of compound I-c was established as (2S,3S,4R,5R) with a 2,3-trans, 3,4-cis, 4,5-trans stereochemistry, refer to (FIG. 5.11). Compound I-c was first reported and isolated from *Nectandra rigida* by Le Quesne et al., 1980 and named nectandrin B. It was isolated from *Guaiacum officinale* L. by Junko et al, 1990.

The $^1$H NMR, $^{13}$C NMR, $^{13}$C DEPT and 2-D NMR spectra of compound I-d closely matched the signals reported for I-c (Table 5.3). However, slight differences in downfield chemical shifts were present in all $^1$H signals except for H-2, which had a downfield shift of δ 4.49 to 5.11, the methyl protons being detected further upfield from δ 1.03 to 0.60, and a slight upfield shift of the hydroxyl group. This verifies the stereochemistry of the vicinal methyl and aryl groups of the tetrahydrofuran ring of compound 4 is in cis orientation. Although the spectral data closely matched that reported for saucernetin reported by Rao in 1997, H-2 and H-5 was detected at δ 5.11 further upfield than that previously reported at δ 5.42 which is clearly in agreement with two cis oriented relationships between the vicinal Me and aryl groups at H-3 & H-2 and H-4 & H-5. It is also further downfield than the expected trans signal, which is reported to fall between δ 4.5-4.7, Furthermore, there was little measurable optical rotation thus confirming the symmetry of the molecule. Therefore based on NMR data, stereochemistry, and the coupling constants and the close association with the previously reported NMR data compound I-d was established as isonectandrin B, (2S,3R,4S,5R) with a 2,3-cis, 3,4-cis, 4,5-cis stereochemistry, (FIG. 5.11). Isonectandrin B was first isolated in *Piper polysyphorum* by Zhang et al, 1997. This is the first time it has been isolated and reported from *Guaiacum officinale* L. or any member of the Zygophyllaceae family.

The $^1$H NMR spectrum of compound I-e suggested a non-symmetric tetrahydrofuran lignan. The molecular ion peak at m/z 344 in the mass spectrum confirmed the same molecular structure ($C_{20}H_{24}O_5$). Protons in the aromatic region displayed three doublets at δ 6.9 (d, J=1.2 Hz), 6.93 (d, J=1.2 Hz), 6.89 (d, J=7.8 Hz), two doublets of doublets at δ 6.85 (dd, J=7.9 Hz) and 6.78 (dd, J=9.9 Hz), two hydroxyl singlets at δ 5.54 and 5.58, two methine doublets at 5.45 (d, J=9.4 Hz) and δ 4.64 (d, J=9.4 Hz), a methoxy doublet at δ 3.90 (d, J=5.6 Hz), a methine multiplet at δ 2.43, and two methyl doublets at δ 1.0 (d, J=6.3 Hz) and 0.59 (d, J=6.8 Hz), refer to (Appendix B14). The correlations displayed by the $^1$H-$^1$H COSY showed similar correlations to the previous COSY's, however, the methine at position 7 displayed $^1$H-$^1$H COSY correlation to H-3 and H4 in addition to both methyl groups. The methine at position 7 'displayed $^1$H-$^1$H COSY correlation to H-3, (Appendix B15). The HSQC further confirmed the asymmetry structure by showing two cross peaks for the methyl carbon. Two cross peaks were also evident for H-2 and H-5. In addition, the coupling constant J=9.1 of the doublet at δ 4.64 showed that the H-2 proton is in trans configuration and that the smaller coupling constant J=4.19 of the doublet for H-2 is in cis confirmation with H-4, suggesting unlike the single chemical shift for compounds 3 and 4, compound 5 has the following stereochemistry, (2S,3S, 4R,5S) 2,3-trans, 3,4- cis, and 4,5-cis. This compound has been previously isolated from *Machilus thunbergii* and is reported as machilin 1.

TABLE E3

¹H and ¹³C NMR spectral data for compounds I-c, I-d, and I-e.

| Carbon No. | I-c δ_H (mult.; J_HH, Hz) | δ_C | I-d δ_H (mult.; J_HH, Hz) | δ_C | I-e δ_H (mult.; J_HH, Hz) | δ_C |
|---|---|---|---|---|---|---|
| 2 | 4.49 (d, 6.3) | 87.2 | 5.11 (d, 6.3) | 82.7 | 4.64 (d, 9.1) | — |
| 3 | 2.33 (m) | 4.3 | 2.66 (m) | 41.5 | 2.43 (m) | — |
| 4 | | | | | " | — |
| 5 | | | | | 5.45 (d, 4.2) | — |
| 1' | | 134.2 | | 132.5 | | — |
| 1" | | " | | " | | — |
| 2' | 6.88 (s) | 109.4 | 6.9 (s) | 109.1 | 6.95 (d, 1.2) | — |
| 2" | " | " | " | " | " | — |
| 3' | | 146.6 | | 146.2 | | — |
| 3" | | " | | " | | — |
| 4' | | 145.1 | | 144.4 | | — |
| 4" | | " | | " | | — |
| 5' | 6.95 (d, 2.8) | 114.3 | 6.98 (d, 1.4) | 114.0 | 6.89 (d, 7.8) | — |
| 5" | " | " | " | " | " | — |
| 6' | 6.91 (d, 2.8) | 119.2 | 6.90 (d, 1.4) | 119.3 | 6.78 (dd, 8.0, 1.3) | — |
| 6" | " | " | " | " | " | — |
| 3'-MeO | 3.88 (s) | 55.9 | 3.90 (s) | 55.9 | 3.90 (d, 6.8) | — |
| 3"-MeO | " | " | " | " | 1.0 (d, 6.3) | — |
| 4'-OH | 5.59 (s) | | 5.57 (s) | | 5.54 (d, 9.5) | — |
| 4"-OH | " | | " | | " | — |
| Me' | 1.03 (d, 6.6) | 13.0 | 0.60 (d, 6.6) | 11.7 | 0.59 | — |
| Me" | " | " | " | " | " | — |
| | | | | | 2", 6.93 (d, 1.2) | |
| | | | | | 6", 6.85 (dd, 7.9, 1.2), | |

Diarylbutane-Type Lignans

The ¹H NMR data of meso-dihydroguaiaretic acid I-f was in agreement with the literature values.

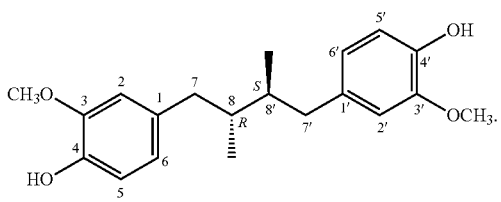

I-f

The COSY, HMBC, and HSQC confirmed the results. The ¹H NMR spectra of meso-dihydroguaiaretic acid showed doublets for aromatic proton signals at δ 6.83 (d, J=8.0 Hz) and at 6.62 (d, J=2.0 Hz), a doublet of doublets at δ 6.66 (d, J=8.0, 1.65 Hz), a broad hydroxyl peak δ 5.46 (s) and methoxy at δ 3.90 (s), two methylene protons at δ 2.73 (dd, J=13.5 Hz) and at 2.27 (dd, J=13.9 Hz), another methine at δ 1.75 and a methyl group at δ 5.45 (d, J=6.63 Hz), refer to (Appendix B17). The results of the HSQC spectra supported the 1,3,4,-trisubstituted benzene ring suggesting the OH and MeO substituents were at positions 3 and 4 of the aromatic ring, (Appendix B18). The ¹H-¹H COSY correlations supported the 1,4 diarylbutane structures. The HMBC confirmed the correlation of the methyl groups to C8 and C8' and the C7 and C7' correlations to carbons C2, C5, and C6 of the aromatic ring. The optical rotation can enhance the absolute stereochemistry assessment since the trans (dihydroguaiaretic acid) has optical activity rel-(8S-8'S) and meso-dihydroguaiaretic has (8R-8'S) configuration and has no optical activity.

Phenol, 4,4'-[(2S,3S,4R,5R)-tetrahydro-3,4-dimethyl-2-5, furandiyl]bis[2-methoxy-, nectandrin B (3). Pale yellow oily compound. High resolution FAB (m/z: [M-H]⁻ for $C_{20}H_{24}O_5$) and ESI mass spectra (negative mode, pseudo molecular ion m/z=343.9 [M-H]⁻) displayed a molecular weight of 344. The fragmentation pattern exhibited prominent fragment ions at m/z (rel. int.): 344 [M]⁺⁺=125.3, 137.1, 326.8, 382.3. $[\alpha]_D$-1.30° (CHCl₃). HMBC NMR: CH₃ to CH₃, C3, C4, C2, C5, C1' and C1'); H3 and H4 to C3, C4, C2, C5, C1' and C1"; OCH₃ to C3', C3" C4', and C4"; H2 and H5 to CH₃, C3, C4, C2', C2", C6', C6", C1' and C1'; H—Ar— to C2, C5, C2', C2", C3', C3", C4', C4", C5', C5", C6', C6".

Phenol, 4,4'-[(2R,3S,4R,5S)-tetrahydro-3,4-dimethyl-2-5, furandiyl]bis[2-methoxy-, isonectandrin B (I-d). High resolution FAB (m/z: [M-H]⁻ for $C_{20}H_{24}O_5$;) and ESI mass spectra (negative mode, pseudo molecular ion m/z=343.2 [M-H]⁻) displayed a molecular weight of 344. The fragmentation pattern exhibited prominent fragment ions at m/z (rel. int.): 344 [M]⁺⁺=93.3, 149.1, 203.0, 278.9, 326.8. $[\alpha]_D$+13.57° (CHCl₃). HMBC NMR: CH₃ to CH₃, C3, C4, C2, C5, C1' and C1'; H3 and H4 to C3, C4, C2, C5, C1' and C1"; OCH₃ to C3', C3" C4', and C4"; H2 and H5 to CH₃, C3, C4, C2', C2", C6', C6", C1' and C1'; H—Ar— to C2, C5, C2', C2", C3', C3", C4', C4", C5', C5", C6', C6".

Phenol, 4,4'-[(2S,3S,4R,5S)-tetrahydro-3,4-dimethyl-2-5, furandiyl]bis[2-methoxy-, machilin I (I-e). High resolution FAB (m/z: 344 [M-H]⁻ for $C_{20}H_{24}O_5$) and ESI mass spectra (negative mode, pseudo molecular ion m/z=344.1 [M-H]⁻) displayed a molecular weight of 344. The fragmentation pattern exhibited prominent fragment ions at m/z (rel. int.): 344 [M]⁺⁺, 137.0, 203.0, 326.6, 382.6.

Phenol, 4,4'-[2,3-dimethyl-1-4,butanediyl]bis[2-methoxy-(R,S)—, meso-dihydroguaiaretic acid (I-f). High resolution FAB (m/z: 330 [M-H]⁻ for $C_{20}H_{24}O_5$) and ESI mass spectra (negative mode, pseudo molecular ion m/z=329.2 [M-H]⁻) displayed a molecular weight of 330. The fragmentation pattern exhibited prominent fragment ions at m/z (rel. int.): 330 [M]⁺⁺, 206.6 and 329.2. HMBC NMR: CH₃ to C8 and C8'; H8 and H8' to CH₃, C8, C8', C2, C2', C4, C4', C6 and C6'; OCH₃ to C3, C3', C4, and C4'; H—Ar— to C8, C8', C2, C2, C3, C3', C4, C4', C5, C5', C6, C6'.

Biological Activity of Fractionated *Guaiacum wood*.

Figure 17:
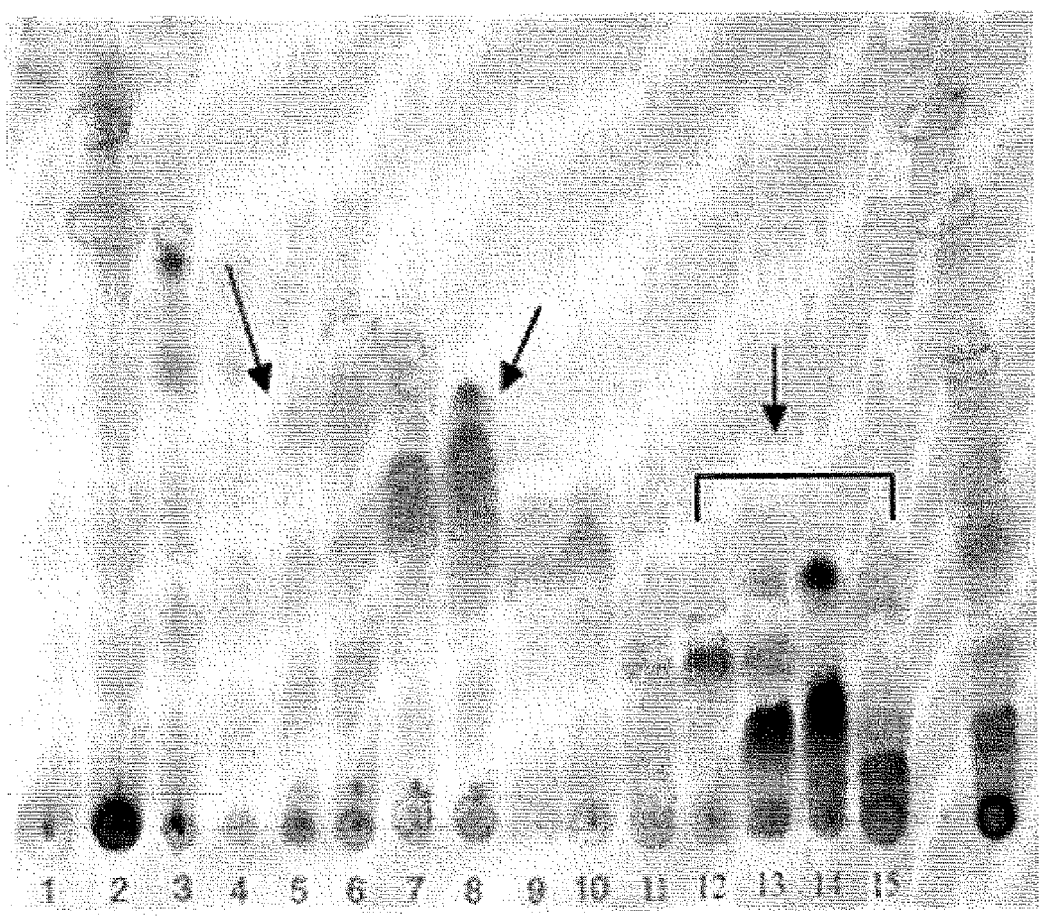
FIG. 17 shows TLC evaluation of fractions obtained from DCM sephadex column chromatography. Arrows indicate the fractions further evaluated. The TLC plate was eluted with $CHCl_3$ (95%): Acetone (5%) and visualized with UV and vanillin-$H_2SO_4$ stain.
Figure 18:
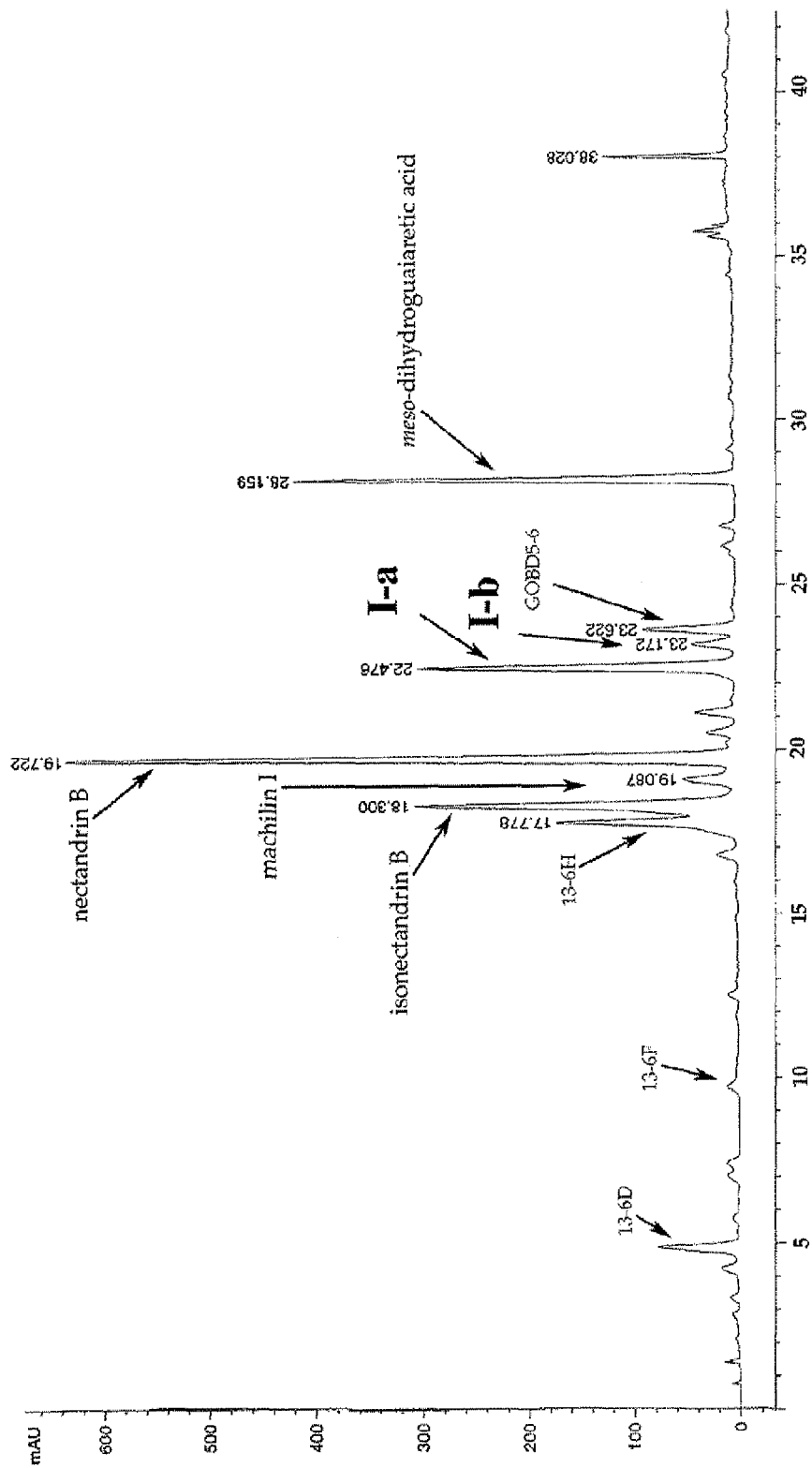
FIG. 18 shows the HPLC chromatogram of the crude dichloromethane extract of bark from *Guaiacum officinale*.

Three fractions were chosen for further evaluation based on their apoptotic activity, yields, and simplicity of their HPLC profiles. Fraction 5 was obtained by combining F5 and F6, and fraction 13 by combining fractions 13 and 14. Fraction 8 was not combined with any other. Combinations were based on TLC profiles, (FIG. 17). The percent apoptosis was calculated by using Annexin V/FITC staining and flow cytometry (Table E4).

TABLE E4

Bioactivity against human breast cancer cell line MD-MBA-231 of Fractions F1-17 obtained from the wood of *Guaiacum officinale* L. by sephadex (85% DCM and 15% Acetone) column.

| Fractions | Dose (ppm) | Apoptosis % | Necrosis % |
|---|---|---|---|
| 1 | 100 | 11.69 | 9.0 |
| 2 | 100 | 19.2 | 31.31 |
| 3 | 100 | 73.14 | 8.50 |
| 4 | 100 | 37.33 | 27.65 |
| 5 | 100 | 10.85 | 18.54 |
| 6 | 100 | 63.77 | 0.96 |
| 7 | 100 | 79.83 | 6.35 |
| 8 | 100 | 89.98 | 2.31 |
| 9 | 100 | 86.79 | 1.08 |
| 10 | 100 | 76.98 | 4.07 |

TABLE E4-continued

Bioactivity against human breast cancer cell line MD-MBA-231 of Fractions F1-17 obtained from the wood of *Guaiacum officinale* L. by sephadex (85% DCM and 15% Acetone) column.

| Fractions | Dose (ppm) | Apoptosis % | Necrosis % |
|---|---|---|---|
| 11 | 100 | 70.59 | 10.69 |
| 12 | 100 | 74.97 | 6.75 |
| 13 | 100 | 63.90 | 5.31 |
| 14 | 100 | 66.0 | 2.75 |
| 15 | 100 | 57.94 | 21.37 |
| Crude extract | 100 | 62.26 | 0.95 |

The final percent apoptosis was calculated by combining cells found in both early and late stages of staining with Annexin V. Fraction 5 displayed 10.85% apoptosis and F6 displayed 63.77% apoptosis at 100 ppm. F8 showed the highest activity of the three displaying 89.98% apoptosis at 100 ppm and 51.38% at 25 ppm. F13 showed a combination of 63.9 and 66.0% apoptosis. These fractions were subject to further isolation procedures as described above, refer to tree diagrams (FIG. 13) and (FIG. 14). The activity of the compounds against human breast cancer cell line MD-MBA 231 is summarized in (Table E5).

TABLE E5

| Compounds | (Names) | Dose | Apoptosis | Necrosis |
|---|---|---|---|---|
| I-a | | 100 | 90.12 | 0.82 |
| I-b | | 100 | 81.37 | 0.41 |
| I-c | (nectandrin B) | 100 | 92.9 | 1.81 |
| I-d | (isonectandrin B) | 100 | 91.14 | 0.35 |
| I-e | (machilin I) | 100 | — | — |
| I-f | (meso-dihydroguaiaretic acid) | 100 | — | — |

The wood examined herein, *Guaiacum officinale* L. and *Guaiacum sanctum* L. was collected and branches approximately 10 mm to 20 mm in diameter were stripped of their bark and each one was stored in separate containers. The bark and wood were cut into small pieces, air dried, and ground separately. A voucher specimen was deposited at the L. H. Bailey Hortorium Herbarium (BH) at Cornell University, Ithaca, N.Y. under Specimen accession number #1883 (2000).

Ground plant material (1,200 g) was exhaustively extracted with a rotoevaporator for 72 hours at room temperature with a 1:1 ratio of chloroform to methanol. The solvent was evaporated to yield a crude extract and then re-dissolved first in chloroform followed by methanol with subsequent evaporation to yield two fractions for each plant.

An aliquot of the heartwood from *Guaiacum officinale* L. concentrate (90 mg-159 mg) was taken to dryness under nitrogen and dissolved in 1:1, $CH_3OH$ and THF to equal 600 µl. The extract was filtered through a Nylon 0.2 µm filter. Analytical separation was carried out by HPLC with a Synergi 4µ Polar-RP 80A column. The column length was 250× 4.60 4µ micron. The *Guaiacum* extract was separated using a gradient with a mixture of $H_2O$, $CH_3OH$ and THF at 0 min 20% MeOH and 80% $H_2O$, 10 min 40% MeOH, 15 min 60% MeOH, 20 min 100% MeOH, 25 min 80 MeOH % and 20% THF, 30 min 60% MeOH and 40% THF, 35 min 100% MeOH. The injection was 12.5 µl. Further purification of fractions 4 and 5 were HPLC analyzed with a Luna 3µ C18 (2) column with a size of 150×4.60 mm Micron. A gradient with a mixture of $H_2O$, $CH_3OH$ and THF was used at 0 min 30% MeOH and 70% $H_2O$, 5 min 50% MeOH, 15 min 800% MeOH, 25 min 100% MeOH, 30 min 80 MeOH % and 20% THF, 35 min 100% MeOH. The injection was 100 µl.

Human breast carcinoma cell line lines; SKBR-3, BT20, MB-MDA-468, MB-MDA-453, MB-MDA-231, and MCF-7 and human cancer cell lines Calu-6, Hela, HCT-116, HT-29, and A-431, obtained from ATCC (Manassas, Va.), were cultured in Dulbecco's Modified Eagle's Medium (DMEM-Sigma D-564R) supplemented with 10% Fetal Calf Serum (heat-inactivated) and antibiotics (Antibiotic Antimycotic Solution 100×, Sigma A9909). Breast cancer cell lines were chosen based on their varying amount of Epidermal Growth Factor Receptors (EGFR). Cells were routinely propagated and cultured at 37° C. in a 100% relative humidified atmosphere consisting of 5% $CO_2$ and 95% air. Cells were trypsinized with 0.05% Trypsin-0.2% EDTA (w/v) solution. All experiments were repeated at least three times.

Figure 4:
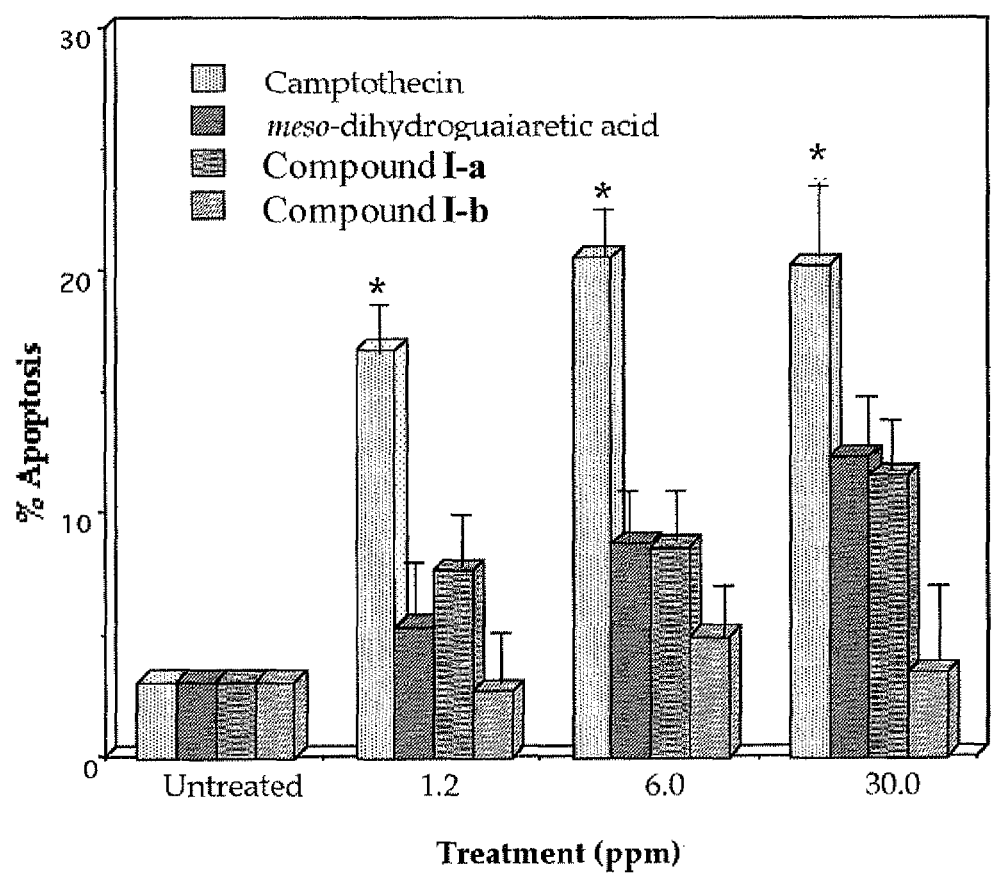
FIG. 4 shows the effect of the spirocyclic lignans I-a, I-b, and meso-dihydroguaiaretic acid on the induction of early stage apoptosis in human breast cancer cell line MD-MBA 231. Analysis was performed with Annexin V-FITC and PI staining and read by FACS. Camptothecin was the positive control. Treatment means with an * are statistically different from the control group at the 5% level according to Fisher's Projected LSD (SuperANOVA 1989).

Cells were seeded onto a standard 96-well microtiter plate at a density of 2×104 cells/well in 100-µl tissue culture medium. After a 24-h incubation period to allow cells to adhere and reach 100% confluency, cells were treated with crude methanol and chloroform extracts from both the bark and heartwood of *Guaiacum sanctum* L. and *Guaiacum officinale* L. Inoculation densities for the five cell lines were approximately 5,000 cells per well. Test compounds were mixed in solution using DMSO as vehicle (10 µg extract/1 ul DMSO) at a total of 100-µl. Each well was evaluated at seven 10-fold dilutions starting from a high of 1000 ppm. Control groups were treated with DMSO (0.1%) equal to the highest percentage of extract used in experimental conditions. DMSO and untreated cells were used as negative controls. Camptothecin (CPT) and 5-Fluorouracil (5-FU) were used as positive controls (FIG. 4.2.). Following a 48-h incubation period, extracted cells were evaluated using Alamar Blue, a fluorometric/colorimetric assay that measures cell proliferation by relying on the cells metabolic activity. In the presence of added toxic compounds, the cells innate metabolic activity ceases. This assay incorporates a specially selected oxidation-reduction (REDOX) indicator that both fluoresces and undergoes colorimetric change (fluoresces red) in response to cellular metabolic reduction. Data were analyzed immediately by visualizing color densities and/or with a standard spectrophotometer at 540 nm.

In addition to Alamar blue, Sulforhodamine B Assay (SRB) was used to determine inhibition by bound protein. Individual cell lines were seeded at varying cell densities as determined by growth rate. Inoculation densities ranged between 9000-4000 cells per well and were based on a linear relationship with an OD ranging between 1.2-1.5. After a 24-h incubation period DMSO was used as vehicle and crude extracts were added, as indicated. Seven $^{1}/_{10}$-fold dilutions were made. 5-FU was used as a positive control. As indicated by Skehab et al. 1990, cultures were terminated by trichloracetic acid (10%), washed with cold tap water, stained with SRB (100 ul) at 0.4% (w/v) in 1% acetic acid and incubated at room temperature for 10 minutes. Unbound dye was removed by five washes with (1%) acetic acid and air-dried. Dye-stained protein was extracted with 10 mM TRIS base. The absorbance of stained protein was read with an automated 96-well microtiter ELISA plate reader (SAFIRE) at 540 nm. Using absorbance measurement [time zero. (Tz)—control growth, and growth at each drug concentration level (Ti)], the percentage growth is calculated at each of the drug concentrations. Percent growth inhibition is calculated as: [(Ti−Tz)/Tz]×100 for concentration for which Ti<Tz.

The induction of apoptosis in cell cultures was analyzed using a double-fluorescence staining technique with a Hoechst 33342/Propidium Iodide (H/PI) assay (Muscarella et al, 1997). MD-MBA 231 and SKBR3 were seeded at low density (1.0×10 4 cells/ml) in 6 well plates. After 24-h growth, Camptothecin (CPT), DMSO, and *Guaiacum* extracts at concentrations of 5, 20, and 35 μl were added. Samples were collected at various times 6, 12, and 24 h at which both the supernatant and adhered cells were stained in 20-μg/ml propidium iodide (emitting red fluorescence) and 100 μg/ml Hoechst 33342 (emitting blue fluorescence) for 15 min at 37° C. in the dark. The double fluorescence was detected with a Zeiss fluorescence microscope (Carl Zeiss, Inc., Thornwood, N.Y.) with an epifluorescence system with a long pass filter cube A. This procedure allows easy and simultaneous detection between apoptosis and necrotic cell death by the detection of plasma membrane integrity and dye exclusion in live cells. Necrotic cells emit red, were swollen and had irregular/damaged membranes. Apoptotic cells were easily distinguished by their phenotype of condensed and segregated chromatin and stained blue in early stages and red in later stages. Each sample was scored four times with an average between 75-100 cells per count. They were classified as either apoptotic, necrotic, or normal/viable.

All graphed data for various parameters represent +SE, and data sets were compared using General Linear Model of ANOVA (SuperANOVA). For each variable, means statistically different were separated at the 5% level using Duncan's new multiple range test.

To determine the cytotoxic effect of the crude extracts from the heartwood of *Guaiacum sanctum* on various breast cancer cell lines, proliferation was assessed using Alamar Blue. Cell death was detected at 15.6 ppm for cell lines BT20 and MB-MDA-453 and 31.25 ppm for cell lines SKBR3, MB-MDA-231 and MB-MDA-468 (FIG. 19). The viability of positive controls 5-FU and CPT were averaged across cell lines for tabular representation. Treatment with 5-FU displayed cell death at the same lower limits as cell lines BT20 and MB-MDA-453. Camptothecin displayed the greatest inhibition at 7.81 ppm. Thus, since 5-FU was as cytotoxic as *Guaiacum sanctum* L. at the lowest concentration and since camptothecin shown the most potent cytotoxic activity, one or both of these drugs were used as cytotoxic and apoptotic markers for the rest of the experiments.

Figure 20:
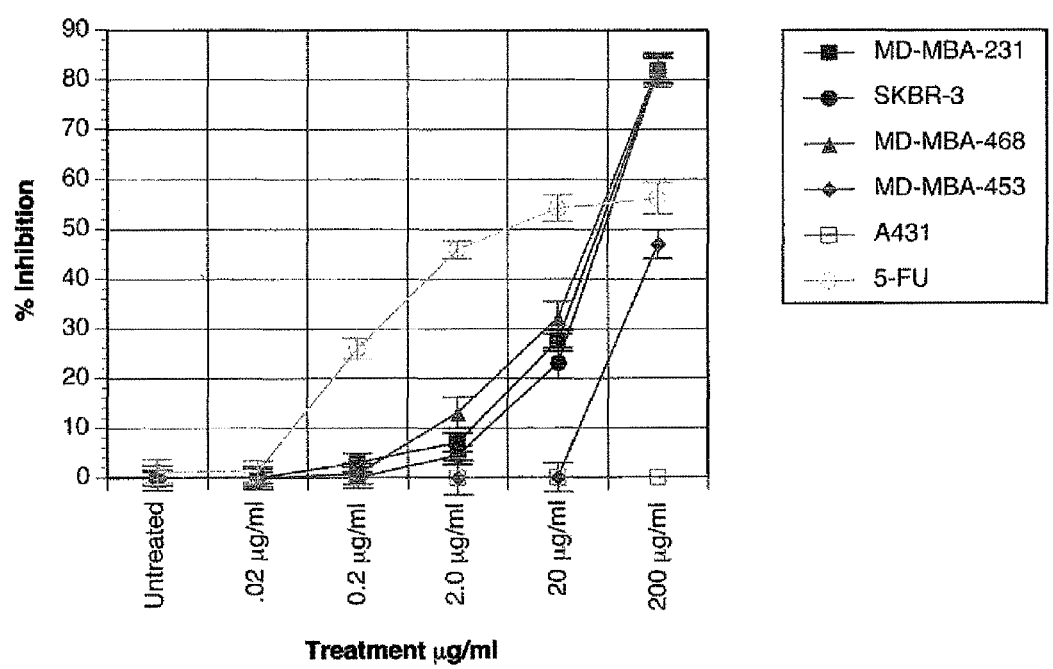
FIG. 20 shows the antiproliferative activity of the wood extract from *Guaiacum sanctum* L. (Zygophylacceae) against breast cancer cell lines using SRB Assay: SKBR-3, MB-MDA-468, MB-MDA-231, MB-MDA-453, epithelial skin cancer cell line A431, and simian cancer cell line COS. The positive control was 5-fluorouracil.

Further cytotoxic analysis of the crude extract from the heartwood of *Guaiacum sanctum* L. was examined for determination of bound protein by SRB. This was done to assess a different quantitative method of cell inhibition. An IC50 at log concentration of 2 μM was reported in cell lines SKBR3, MB-MDA 468, and MB-MDA 453. The highest concentration of the crude extract inhibited cell growth by approximately 85% as compared to 5-fluorouracil, which inhibited cell growth at approximately 60%. Interestingly, no activity was reported in cervical cell line A 431, epidermoid carcinoma cells (FIG. 20). The antiproliferative activity was compared with the average positive control effect on all cell lines.

Figure 21:
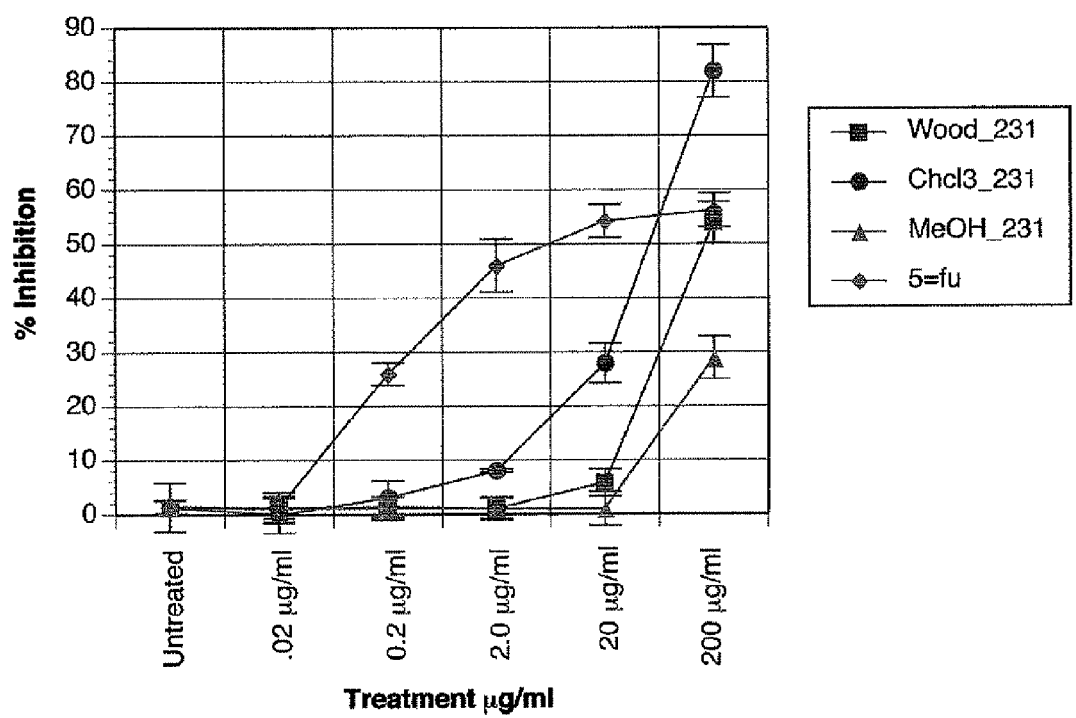
FIG. 21 shows antiproliferative activity of the wood extract and the chloroform and methanol fractions from the heartwood of *Guaiacum sanctum* L. (Zygophylacceae) against breast cancer cell lines: MB-MDA-231. Cells were treated with 200, 20, 2, 0.2 and 0.02 µg/ml of the wood from *Guaiacum sanctum* L. for indicated periods and analyzed with SRB. The positive control is 5-fluorouracil.
Figure 22:
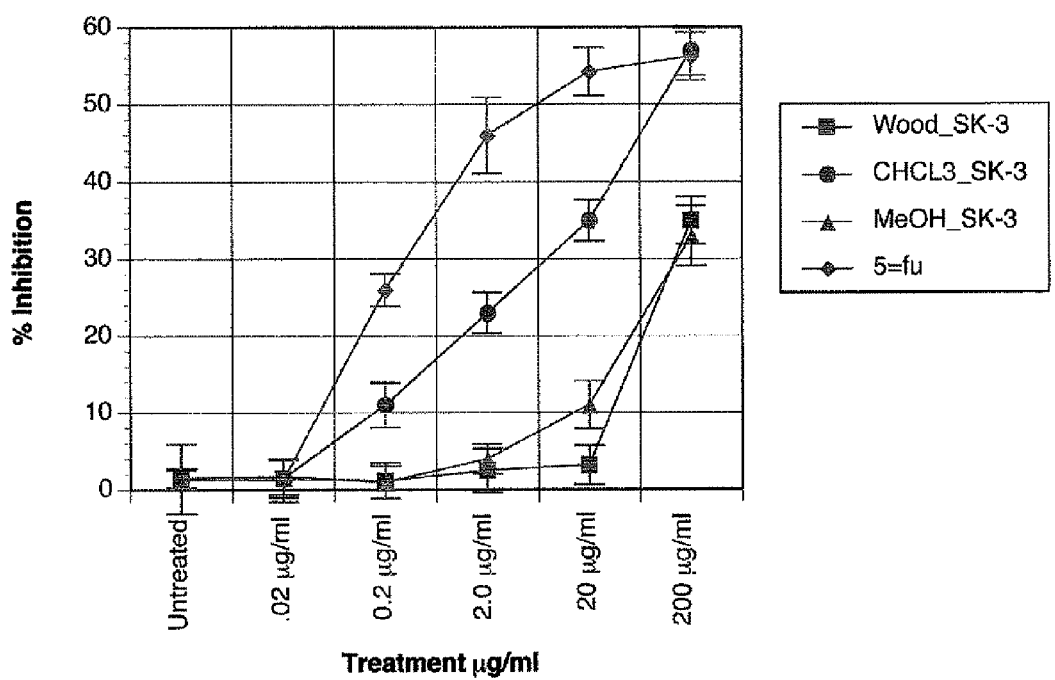
FIG. 22 shows the antiproliferative activity of the wood extract and the chloroform and methanol fractions from the heartwood of *Guaiacum sanctum* L. (Zygophylacceae) against breast cancer cell lines SKBR-3. Cells were treated with 200, 20, 2, 0.2 and 0.02 µg/ml of the wood from *Guaiacum sanctum* L. for indicated periods and analyzed with SRB. The positive control 5-fluorouracil.

For further analysis, the crude extract was dried and re-dissolved first in methanol followed by chloroform to receive to two crude fractions. This was done to decrease the number of constituents present in any one fraction and to separate compounds based on polarity. The results indicate that the chloroform extract of the heartwood induced greater antiproliferative activity than the methanolic extract at all concentrations and doses in cell lines MB-MDA 231 (FIG. 21) and SKBR-3 (FIG. 22). Cell growth was inhibited by 80% at 200 μg/ml and an IC50 at 20 μg/ml was detected for both cell lines. In addition, the crude extract showed greater antiproliferative activity than the methanol fraction in both cell lines.

In the second experiment, since the crude extract of the wood had no effect on epidermoid carcinoma cell line A 431, it was decided to analyze the heartwood across a variety of human cancer cell lines. In addition, analysis was conducted on the bark. Five human cancer cell lines were examined using Alamar Blue Assay; CaLu6 (lung cancer), HCT-116 and HT-29 (colon cancers), HeLa (cervical cancer), and an adenocarcinoma breast cancer cell line MCF-7 (FIG. 23). The results show that strong cytotoxic effects were seen at a concentration of 250 ppm across non-breast cancer cell lines with slight differences in inhibition between the wood and bark extracts. Cytotoxic activity diminished considerably at 125 ppm. Breast cancer cell line MCF-7 showed cytotoxicity at 62.5 ppm. Overall, the results suggest that the active constituents in the wood and bark of *Guaiacum sanctum* L. display a degree of selectivity for human breast cancer cell lines.

To determine if cell death was occurring through an apoptotic mechanism, human breast cancer cell line MD-MBA-231 was exposed to wood and bark extracts of *Guaiacum sanctum* L. in a time and concentration-dependent manner. Apoptosis was determined by detecting the presence of segregated and condensed chromatin by fluorescence microscopy after staining with Hoechst 33342 and necrotic cell death was determined by staining with propidium iodide.

Figure 24:
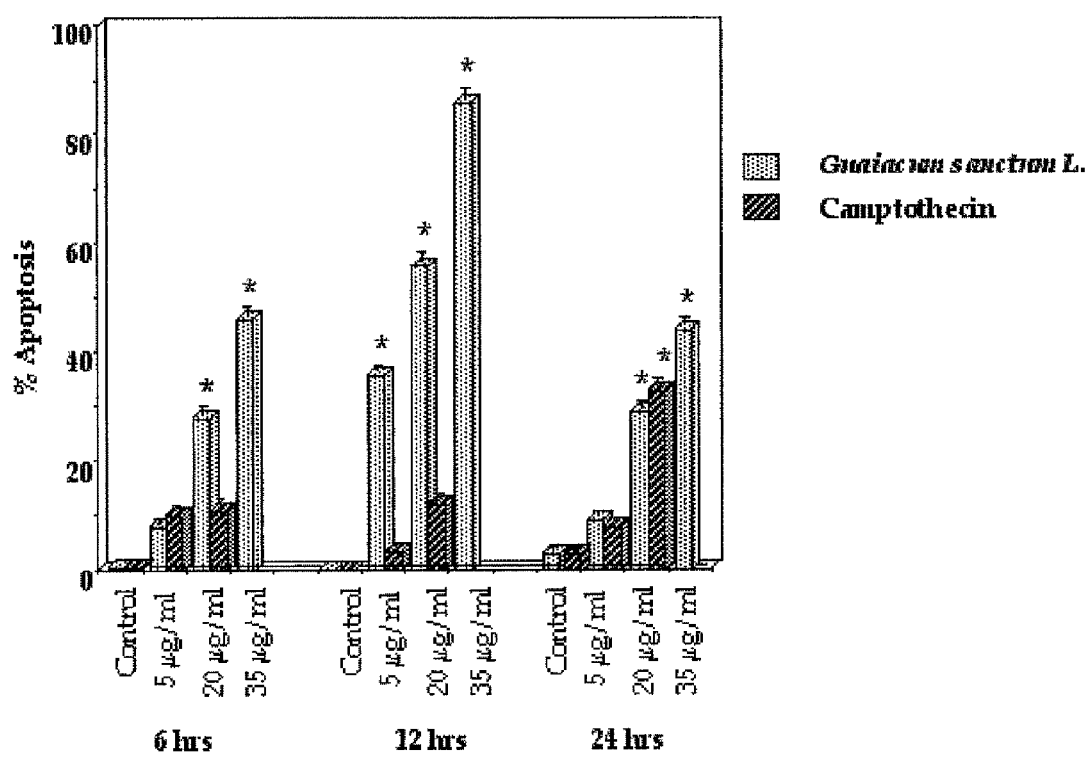
FIG. 24 shows drug-induced apoptosis analyzed by Fluorescent Microscopy on MB-MDA 231. Cells were treated with 0, 5, 20, 35 µg/ml of the heartwood extract from *Guaiacum sanctum* L. for indicated periods and stained with Hoechst 33342/PI. Camptothecin at 5 & 20 µg/ml was used as a positive control. Treatment means with an * are statistically different from the control group at the 5% level for each variable according to Dunican's multiple range test (SuperAnova 1989).

The results indicate that apoptosis was induced in a time and dose dependent manner in cell line MD-MBA-231 in both *Guaiacum sanctum* L. and CPT treated cells. Segregated and condensed chromatin, condensation of the cytoplasm and nucleus and loss of plasma membrane symmetry were seen as early as 6 h. The percentage of apoptosis induced by *Guaiacum sanctum* L. was considerably higher than the amount of apoptosis produced by CPT at all treatments and times except for the low dose at 6 h and at 20 μl at 24 h, (FIG. 24). At concentrations up to 35 μl at 6 h, *Guaiacum* produced 10%, 30% and 50% apoptotic cell death. At 12 h the percentages were 38%, 58%, and 77%. Although, the percent apoptosis at 24 hrs appears lower than that produced at 12 hours, morphological features associated with apoptotic cell death was still present. *Guaiacum* extracts at 35 μg/ml did not have a positive control of CPT due to lack of availability of a well in the 4 ml plates.

Figure 25:
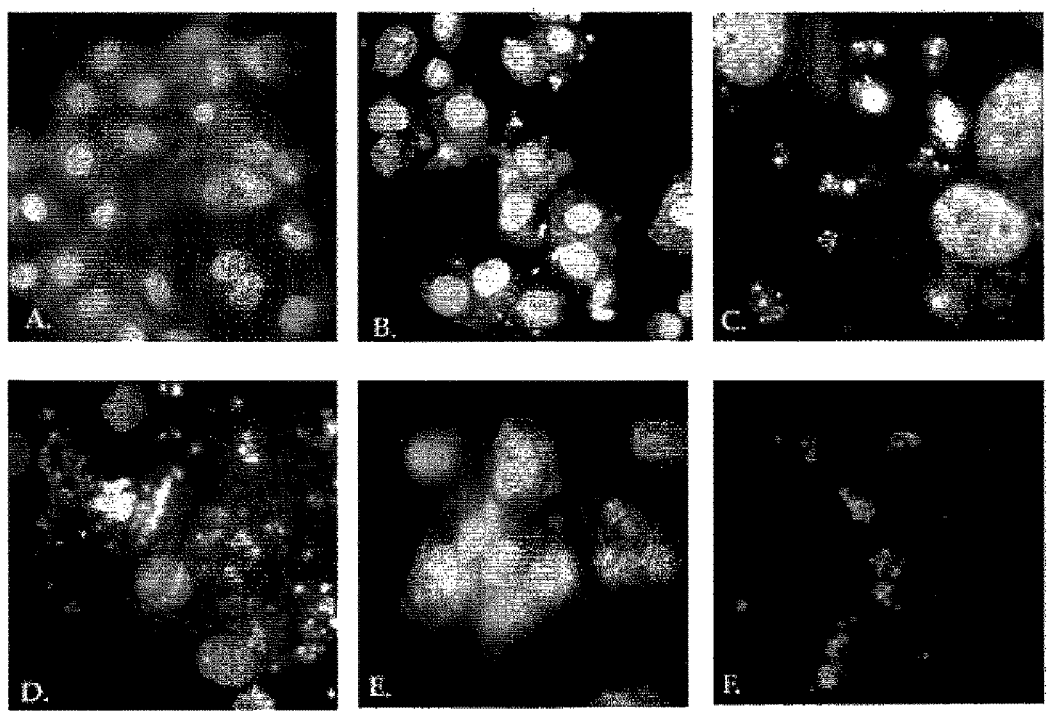
FIG. 25 shows Hoechst 33342 and propidium iodide staining illustrating nuclear condensation and apoptotic bodies characteristic of apoptosis after 24 hour treatment with the heartwood of *Guaiacum sanctum* L. (40× magnification). A) Control 0 µl, B) 5 µl, C) 20 µl, D) 35 µl, E) 5 µl CPT, and F) 20 µl CPT.

The degree of cells undergoing late stages of apoptosis vs. necrotic cell death is difficult to establish. At a certain point in the apoptotic program cells start undergoing certain changes in the plasma membrane which makes the cell permeable to PI, which would not normally occur in early stages of apoptosis. A visual representation of the degree and the morphological of features associated with *Guaiacum* treatment is shown in FIG. 25. Untreated cells (FIG. 25.A) showed normal nuclear morphology and an intact cytoplasmic membrane. With subsequent higher doses increased apoptotic body formation (membrane blebbing) occurs. The difficulty of accessing the activity of cells receiving the higher doses of *Guaiacum* can be viewed in (FIG. 25.D). This particular photograph detects a large number of apoptotic nuclear granules (known as Leuchtenberger or Councilman bodies). Thus, it appears that distinguishing between stains in whole cells does not produce accurate accounts of the entire apoptotic program, but estimates those cells progressing only in early stages of apoptosis. To identify apoptotic cells as they progress through the entire apoptotic program visualization of their morphological features using microscopy is important. Cells treated with camptothecin at 5 and 20 μl can be viewed in FIG. 25, E & F.

The apoptosis-inducing capacity of the bark extracts was more complicated. There appeared to be a clear time and concentration-dependent response at 6 h. However, it appears that the extent and stage of apoptotic cell death was too great for accurate quantification. This was due to the high number of councilman bodies representing very late stages of apoptosis, data not shown. Therefore, it appears that the bark from *Guaiacum sanctum* L. is more potent than the wood and even more so than CPT. Earlier times and smaller doses may be needed for further analysis.

Figure 26:
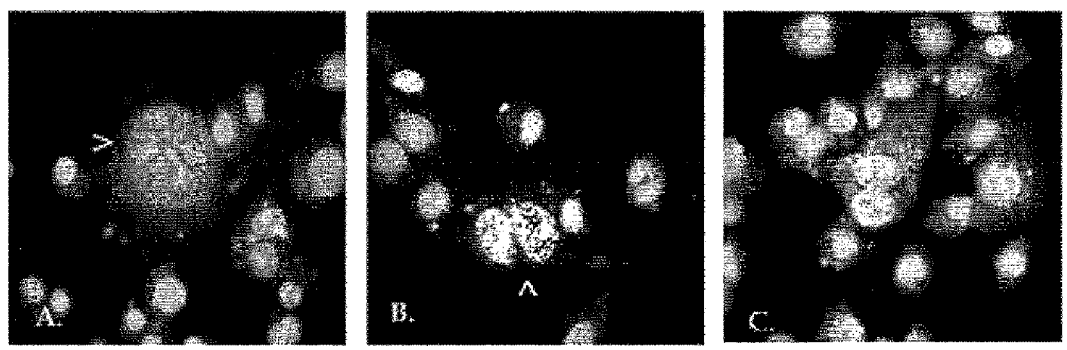
FIG. 26 shows Hoechst 33342 and propidium iodide staining illustrating manifestations on cellular morphology as a result of dosing with 20 µl from the wood of *Guaiacum sanctum* L.—MB-MDA 231. A) Extra-large nucleus, B) bi-nucleated cells, C) condensation and spilling of cytoplasm. Fluorescence micrograph (40×).

On another note, there were some interesting morphological characteristics that were prevalent in cells treated with bark extract. A characteristic that appeared approximately 10-15% of the time were large cells with intact nuclear membranes and slightly condensed chromatin (FIG. 26.A.), in addition to a number of bi-nucleated cells (FIG. 26.B), and lastly, a large number of cells that displayed an overflowing of cytoplasmic material with a loss of nuclei (FIG. 26.C.). This later characteristic appeared quite often at the higher doses.

Fraction Analysis of the Heartwood of *Guaiacum sanctum* and *Guaiacum officinale* by Alamar Blue Preliminary chromatographic separation was evaluated in order to provide insight into the identity of the active fractions. Seven fractions (F1-F7) were obtained from wood extracts from both *Guaiacum sanctum* L. and *Guaiacum officinale* L. and examined with Alamar Blue.

The activity of multiple fractions was similar to the activity derived from the crude and chloroform extracts. Fractions 5, 6, and 7 displayed cytotoxic activity at the lowest concentration (15.62 ppm) followed by F4 (31.2 ppm) in cell line MD-MBA 231 for *Guaiacum sanctum* L. (FIG. 27.A.). Inhibition for *Guaiacum officinale* L. was detected at the lowest concentration (31.25 ppm) for cell lines MB-MDA-468, SKBR-3 and MCF-7 in F5 and F6 followed at 62.5 for F7 (FIG. 27.B.). The resulting activity demonstrates that different constituents, not a single compound may be responsible for the pharmacological properties observed in both *Guaiacum* species, and that, the active constituents may co-exist in both species. The activity for *Guaiacum officinale* L. was higher in F5 and F6 showing cell death at 31.25 ppm and 15.63, respectively.

The data reported hereinbelow shows *Guaiacum officinale* L. heartwood extracts of the invention, and compounds isolated therefrom have cytostatic activity. The activity of the extracts is due in part to the presence of compounds I-a and I-b representing a new family of tetrameric lignans described above. In certain instances these compounds induce apoptosis and influence cell cycle arrest.

General Experimental Conditions

Human breast cancer cell line MB-MDA-231 were cultured in Dulbecco's Modified Eagle's medium (DMEM-Sigma, D-5648), supplemented with 10% (heat-inactivated) Fetal Bovine Serum (Atlanta Biologicals, Inc.) and Antibiotic Solution, 100× (Sigma A-9909). Cells were gown at 37° C., at 5-7% $CO_2$, and 95% humidity and were obtained from the American Type Culture Collection (ATCC). Cells were trypsinized with 0.05% Trypsin-0.2% EDTA (w/v) solution (Invitrogen Corporation, Carlsbad, Calif.).

The induction of apoptosis in MB-MDA-231 was analyzed using a well-validated Annexin V FITC apoptosis detection kit (Calbiochem), Darzynkiewicz, 1998. The phosphatidylserine (PS)-specific dye Annexin-V is used to detect apoptotic-specific changes to the organization of phospholipids leading to exposure of PS on the cell surface that precedes nuclear breakdown, DNA fragmentation, and the appearance of most apoptosis-associated molecules. For these studies cells were seeded at $25 \times 10^4$ cells/1.5 ml in a 24 well microtiter plate. Cells were allowed to adhere to plates for 24 h, and then exposed to lignans of the present invention at 5-fold dilutions of 30 µl, 6 µl, and 1.2 µl per well for 24 h. Test compounds were mixed in solution using DMSO as vehicle (10 mg extract/1 ml DMSO). Camptothecin was used as a positive control. Following the incubation period 700 µl of suspended cells were transferred to 15 ml conical tubes. Cells that remained adhered to the 24-well plates were gently washed with PBS (137 mM NaCl, 2.7 mM KCL, 4.3 mM $Na_2HPO_4$-$7H_2O$, 1.4 mM $KH_2PO_4$, adjusted to pH 7.4), trypsinized with 1 ml of solution (0.05% Trypsin—0.2% EDTA [w/v]), and resuspended with the suspended cells/media collected in the 15 ml conical tubes from the previous step. 10 µl of media-binding reagent and 1.25 µl Annexin V-FITC was added to the 15 ml conical tubes containing both the 700 µl of suspended cells and the resuspended cells and incubated at room temperature for 15 min, at 18-24° C., in the dark. Tubes were centrifuged for 5 minutes at 1000×g at room temperature. Media was removed and cells were gently resuspended in 0.5 ml cold 1× binding buffer (dilution; 5× Binding Buffer concentrate 1:5 with $dH_2O$) and placed on ice. 10 µl of propidium iodide was added to each tube. Cells were placed on ice away from light and analyzed immediately by flow cytometry. The dual fluorescence emissions of the respective dyes were detected in cell preparations on a BD-Biosciences FACS Aria high-speed flow cytometer/cell sorter utilizing a quartz cuvette for interrogation. To quantify the Annexin V (FL1 at 518 nm) and propidium iodide (620 nm) signals, apoptosis-induced cells (CPT) stained with FITC only and apoptosis-induced cells (CPT) labeled with only propidium iodide were utilized. Necessary adjustments were made to minimize overlap between these two measurements. Typically, 10,000-20,000 cells were scored for each sample and classified as either viable, early apoptotic, or late apoptotic or necrotic. All experiments were repeated at least three times, each in duplicate.

Twenty-four hours after exposure to compounds, $25 \times 10^4$ cells in 1.5 ml cells were simply re-suspended following either the Annexin V/FITC assay or the trypsin procedures. Cells were centrifuged at 1000-x g at room temperature and washed in 0.5 ml of hypotonic staining solution. Cells were kept a minimum of 30 min. at 4° C. in the dark. Samples were usually analyzed by flow cytometry on the same day or at 24 hrs. Resulting DNA distributions were analyzed for the proportion of cells in apoptosis and in G0/G1, S, and G2/M phases of the cell cycle. Singlet events were gated and 10,000-20,000 events were acquired within the gated region. All experiments were repeated at least three times, each in duplicate.

Statistical evaluations of all data sets were performed using the linear Model of ANOVA (SuperANOVA 1989). All graphed data for various parameters represent +SE. For each variable (percent apoptosis), statistical evaluations were performed with Fisher's Projected LSD at a significance level of $p<0.05$.

Results of Annexin V/FITC Assay.

Cell surface expression of phosphatidylserine translocated from the inner cytoplasmic membrane is considered an early apoptotic event as opposed to later evidence of apoptosis through morphological examination by microscopy, which reveals chromatin condensation or loss of membrane integrity. The principal of the Annexin V/FITC assay is that, Annexin V, an anticoagulant protein, preferentially binds negatively charged phospholipids. Early in the apoptotic process, phospholipid asymmetry is disrupted leading to the exposure of phosphatidylserine (PS) on the outer leaflet of the cytoplasmic membrane. Annexin V binds to the negatively charged calcium-dependent PS. Conjugating FITC to Annexin V with simultaneous propidium iodide (PI) staining allows bivariate analysis of intact cells. Live, healthy cells are double negative, FITC (−)/PI (−), and are seen in the lower left quadrant [A3] of FACS cytograms. Cells that are FITC (+)/PI (−) [A4] are early apoptotic. Cell populations that are advanced apoptotic or necrotic are FITC (+)/PI (+) are located in quadrant [A2]. Quadrant [A1] contains Annexin V-FITC (−)/PI (+) cells which are stripped of their cytoplasmic membranes leaving isolated nuclei, cells in late necrosis, or cellular debris.

Human breast cancer cell line MD-MBA 231 cells were treated with compounds I-a and I-b, and four previously known lignans: three diaryltetrahydrofuran lignans, nectandrin B, isonectandrin B, and machilin I; and one dibenzybutane lignan, meso-dihydroguaiaretic acid. For comparison, MD-MBA 231 cells were treated with various doses of camptothecin, a topoisomerase (Topo) I inhibitor that causes stabilization of Topo I-DNA complexes. Replication forks formed during S-phase of the cell cycle become stalled at these complexes and subsequently generate double-stranded breaks in DNA. Such breaks are potent signals for apoptosis. Therefore, camptothecin is well known for inducing apoptosis selectively during S-phase of the cell cycle (Darzynkiewicz, et al., 1997 and Robles, et al. 1999).

To determine the effect of the diaryltetrahydrofuran-type lignans (nectandrin B, isonectandrin B and machilin I) on human breast cancer cell line MD-MBA-231, the concentration-dependent induction of apoptosis was studied. The lignans of *Guaiacum officinale* L. were administered at concentrations of 0 ppm (untreated) 1.2, 6.0, and 30.0 for 24 h. Treated cells were evaluated for apoptosis by estimating the percent cells in each of the four FACS quadrants. Percentages of early apoptotic cells treated with the diaryltetrahydrofuran-type lignans are summarized in FIG. 1.

The results indicate that lignans nectandrin B and isonectandrin B and the positive control, camptothecin significantly increased the amount of FITC (+)/PI (−) staining at all doses when compared to the control (untreated) cells. Isoncetandrin surpassed the amount of apoptosis induced by camptothecin at 6.0 ppm and 30.00 ppm by an average of 10% and 24%, respectively. Nectandrin B did so by 10% at 30 ppm. Machilin I did not show any significant increases in apoptotic induction, although apoptosis did increase with increasing drug concentrations.

Figure 2:
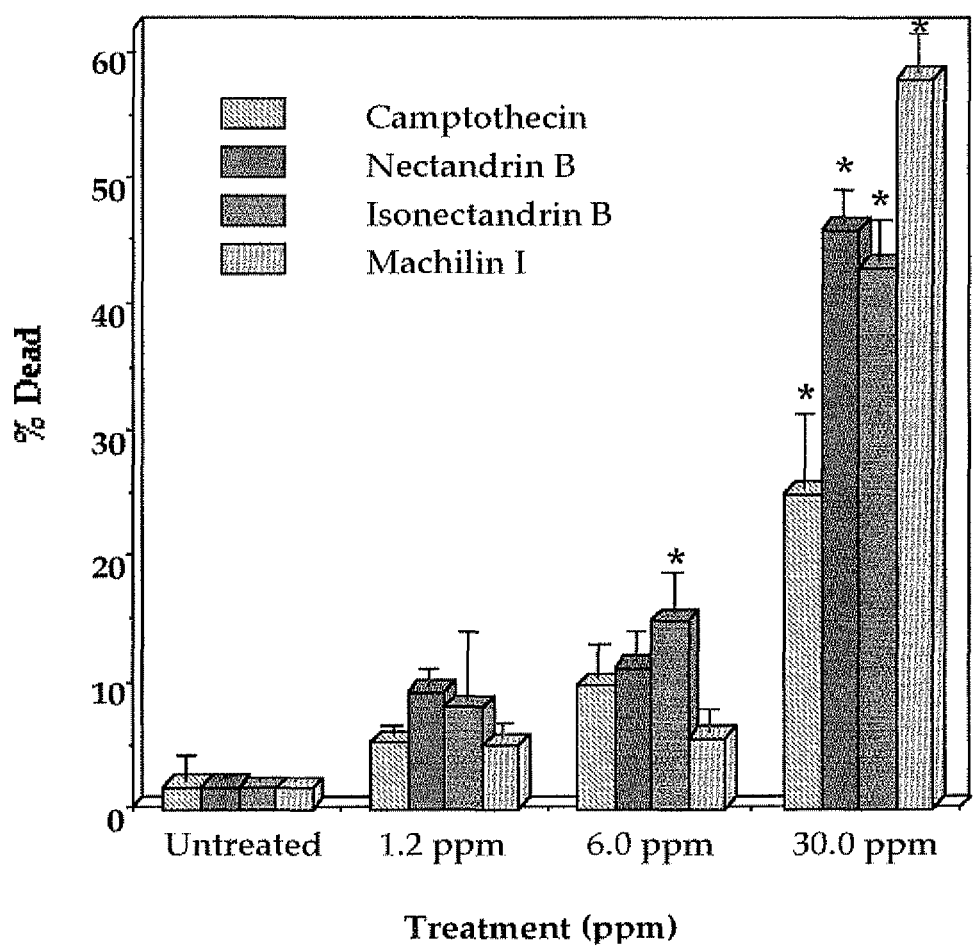
FIG. 2 shows the effect of nectandrin B, isonectandrin B and machilin I on the induction of late stage apoptosis in human breast cancer cell line MD-MBA 231. Cells were exposed at various doses for 24 hr. Analysis was determined by FACS, Annexin V_FITC and PI staining. DNA topoisomerase 1 inhibitor camptothecin was used as a positive control. Treatment means with an * are statistically different from the control group at the 5% level according to Fisher's Projected LSD (SuperANOVA 1989).
Figure 3:
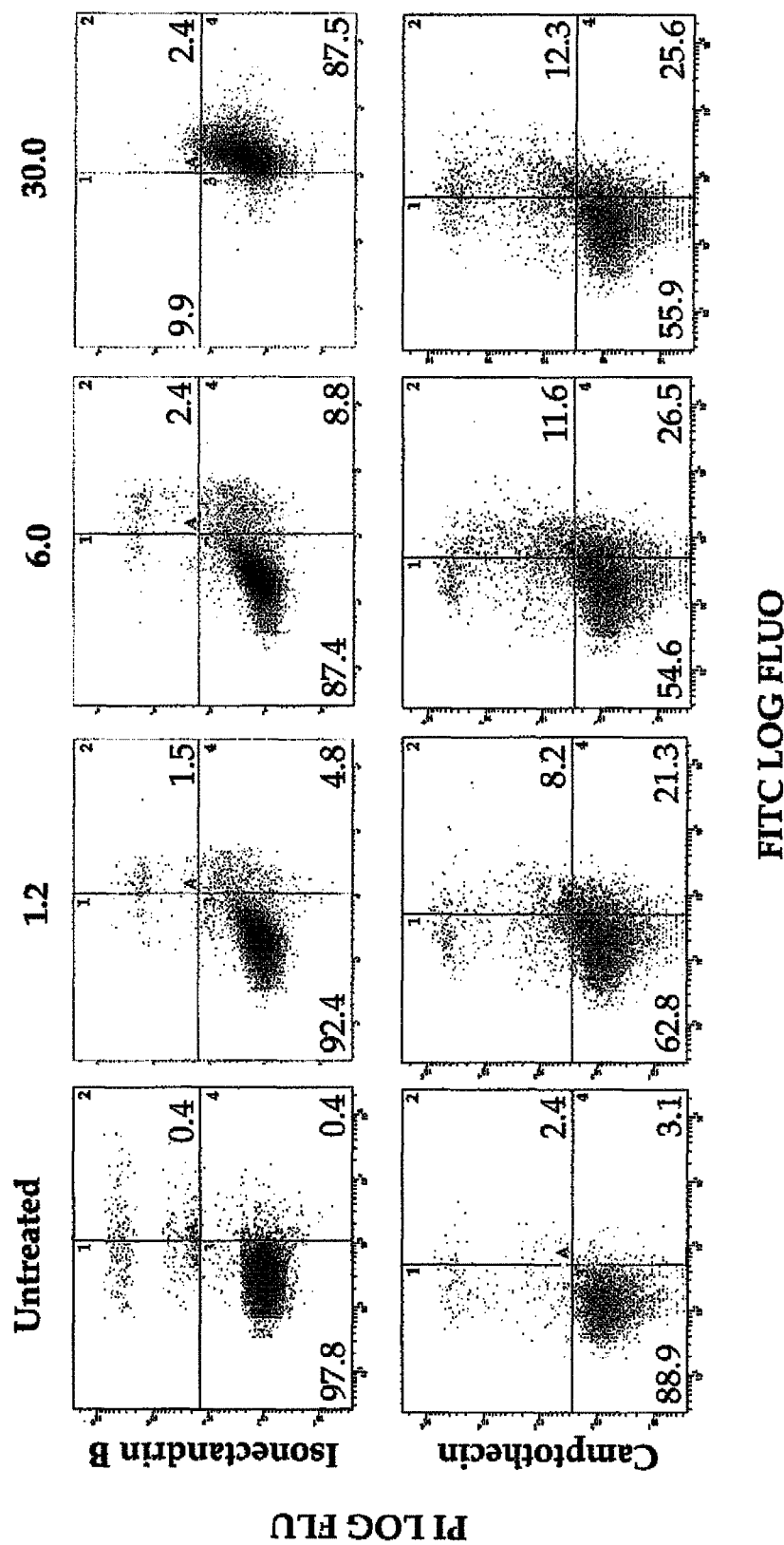
FIG. 3 shows cytograms of MD-MBA-231 cells treated with isonectandrin B and camptothecin. Cells were stained with Annexin V-FITC and PI at 24 hrs. Cells were dosed at control (untreated), 1.2, 6.0, and 30.0 ppm. DNA topoisomerase 1 inhibitor camptothecin is used as a positive control. Figures in the cytogram are indicative of the relative number of cells (%) in the quadrants, live cells [A3], early apoptotic cells [A4], advanced apoptotic or necrotic cells [A2] and isolated nuclei, cells in late necrosis or cellular debris [A1].

Because membrane disruption occurs in later stages of apoptosis, those cells staining for both Annexin V and PI were recorded (FIG. 2). Significance was shown for all compounds at 30 ppm. The cytogram resolved for isonectandrin B and campthotecin is shown in FIG. 3.

The effect of the spirocyclic lignans (I-a and I-b) and the diarylbutane-type lignans (meso-dihydroguaiaretic acid) on the early induction of apoptosis is summarized in FIG. 4. The spirocyclic lignans displayed non-significant increases in early apoptotic cell death with increasing drug concentration at all doses. However, the percent of early stage apoptotic cells was considerably milder compared to the effect produced by camptothecin. The spirocyclic lignans showed 12-14% apoptosis at the highest concentrations, whereas, CPT's activity was increased by at least 5% or more at all doses. Meso-dihydroguaiaretic acid showed similar activity to the spirocyclic lignans. All were non-significant when compared to the positive control.

In contrast, the amount of late stage apoptotic cells was significantly increased for this group (FIG. 5). That is the amount of cells staining for FITC (+)/PI (+) observed in quadrant 2. Activity increased with increasing drug concentrations for all compounds. Compound I-a showed between 48%-54% late stage apoptotic cell death at 6.0 and 30.0 ppm. The effect of 1-b increased the cell death count to 63% at the highest concentration. Camptothecin produced approximately 25%-30% cell death and meso-dihydroguaiaretic between 12%-18% at the two higher doses. This assay does not distinguish between cells that have already undergone apoptotic death and those that have died from a necrotic pathway, per se, although tracking the redistribution of these cells through the cell cycle with DNA content analysis and previous research support our conclusion that cell death did occur by an apoptotic mechanism, however, late stages of apoptosis were occurring at the time and concentrations that were studied.

Cell Cycle Analysis by DNA Content Analysis

The cell cycle comprises steps that regulate the correct temporal sequence of events that control the growth, reproduction and differentiation of cells. The cell cycle consists of 4 phases: G0/G1, S (DNA synthesis), G2, and M (mitosis). In addition, checkpoints located in the cell cycle transition ensure that cell growth and division occur in response to appropriate signals and environment. When proliferating, if cells are subjected to DNA damage the cell cycle temporarily pauses either at G1, S or G2 phase. Arrest at these checkpoints prevents DNA replication and mitosis in the presence of unrepaired DNA damage and presumably allows time for DNA repair to occur. The proportion of cells that arrest in G1, S or G2 after damage depends on cell type, growth conditions, type of damage and the checkpoints operative in the cells. Shifts in the redistribution of phases of the cell cycle in response to various stimuli can be readily assessed by flow cytometry. DNA content analysis with the use of PI is one of the most common assays. The use of intercalating dyes to measure DNA content are the most common and are usually sufficient to determine relative shifts in the phases of the cell cycle. The hypotonic solution lyses the plasma membrane and prevents many of the aggregate problems associated with fixed cells. Propidium Iodide(PI) passes through permeabilized cell membranes and intercalates with cellular DNA. Therefore, the intensity of the PI signal is directly proportional to DNA content. DNA content experiments determine the percent induction of apoptosis and relative distribution of the cell cycle phases.

Most cells spend 50-80% of their growth time in the G1 phase and the least amount of time in G2/M (less than 10% in some cell lines). It is common to have a cell line with a doubling time of 20 hrs, with 14 hrs spent in G1 and a G2/M phase that only takes 4 hrs. In cells that are not synchronized in any way and are randomly distributed throughout the cell cycle, 60% of the cells will be in G1, 20% will be in S phase and 20% will be in G2/M. In our experiment cell line MD-MBA-231 when randomly distributed has approximately 65% of cells in G1, 10-12% in S phase and 17% in G2/M.

To determine the effect on cell cycle distribution for cell line MD-MBA-231, cells were treated with *Guaiacum* lignans at 0 ppm (untreated), 1.2, 6.0, and 30.0, as previously reported for Annexin-V FITC analysis. We first analyzed the distribution of singlet count. This count distinguishes between cells undergoing apoptosis in contrast to cellular debris or dead cells. After 24 h, nectandrin B, isonectandrin B and camptothecin showed considerably fewer singlet counts overall when compared to untreated cells, data not shown. Isonectandrin showed significance decreases at all doses. Camptothecin and nectandrin B reached minimal levels at 30 ppm, although they had an overall steady decrease in cell viability throughout. Exposure to machilin I resulted in an approximately equal level of cell death as shown with untreated cells. These results are remarkably consistent with the analysis from the Annexin V-FITC data of the 2,5-diaryl-3,4-dihyrdromethlytetrahydrofuran lignans, confirming the suitability, confidence, and validity of these methods for discriminating apoptosis.

The percent of apoptotic cells (cells with fractional DNA content; sub G1 cells) were established by estimating the percentage of events showing up in sub G0. The Sub-G1 method relies on the fact that after DNA fragmentation, there are small fragments of DNA that may be eluted. However in order to be seen in the Sub G1 area, a cell must have lost enough DNA to appear there; so if cells enter apoptosis from the S or G2/M phase of the cell cycle or if there is an aneuploid population undergoing apoptosis, they may not appear in the Sub G1 peak. The number of events in sub G1 (number of nuclear fragments) provides no information on the # of cells undergoing apoptosis. The fraction of cells containing a sub G0 DNA content has been shown to correlate with apoptotic cell death and was quantitated by flow cytometry as previously described (Darzynkiewicz, 1992).

Figure 6:
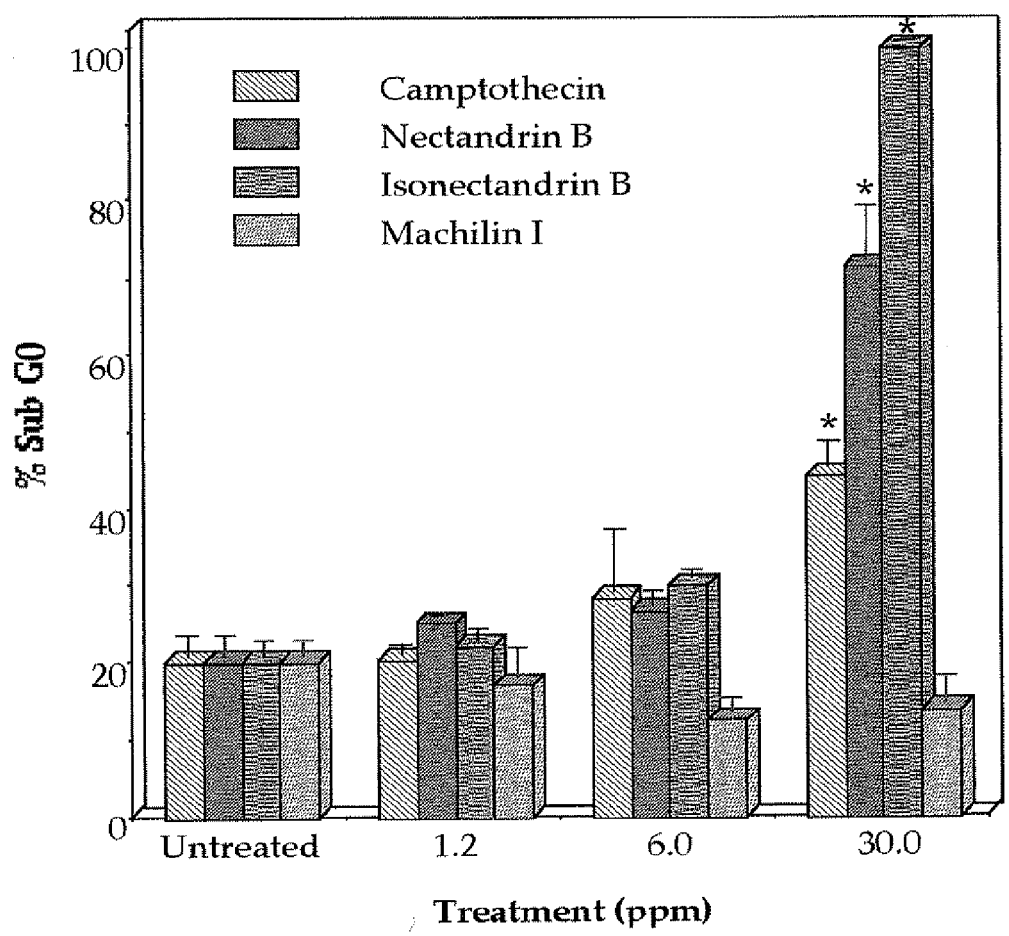
FIG. 6 shows the effect of lignans from the heartwood of *Guaiacum officinale* L. nectandrin B, isonectandrin B and machilin I on the % of cells in Sub G0. Camptothecin was used as a positive control. Treatment means with an * are statistically different from the control group at the 5% level according to Fisher's Projected LSD (SuperANOVA 1989).

To determine the populations of cells undergoing apoptosis, the percent of events in sub G0 were studied. Following 24 h exposure to the diaryltetrahydrofuran-type lignans, isonectandrin B, nectandrin B and camptothecin show increased and significantly induced apoptotic activity at 30.0 ppm (FIG. 6).

Figure 7:
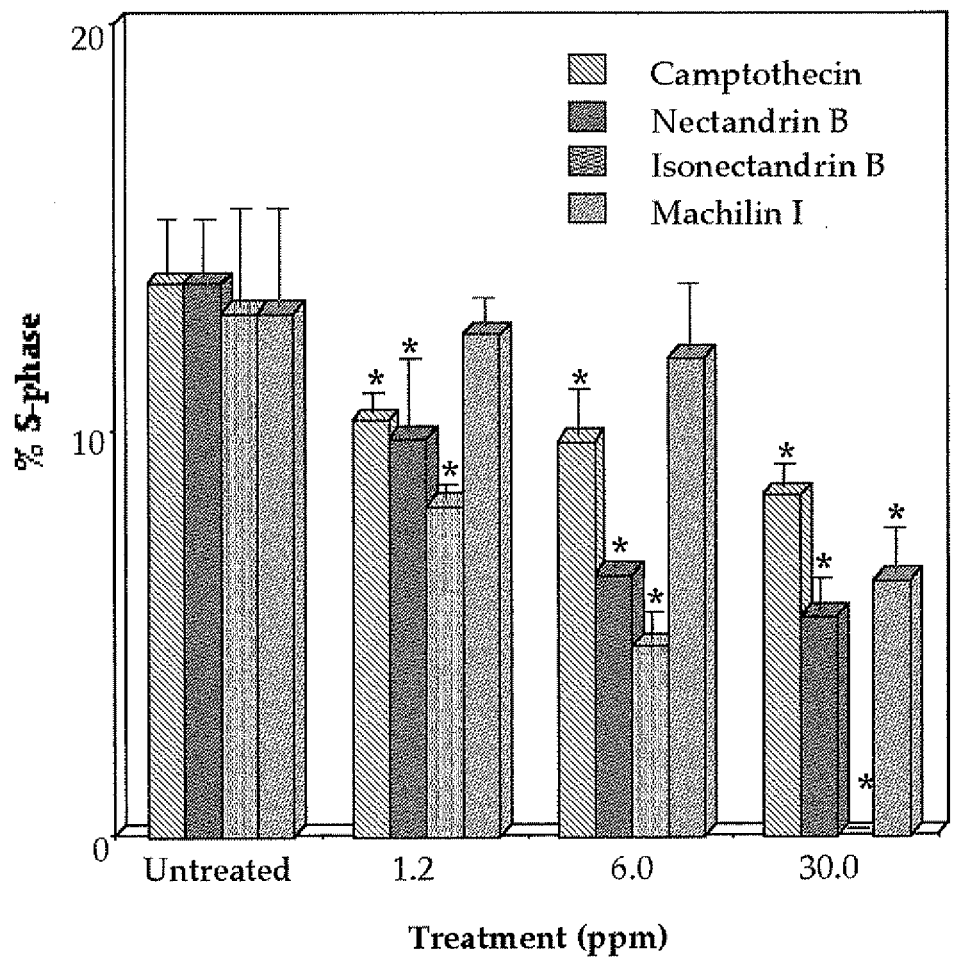
FIG. 7 shows the effect of lignans from the heartwood of *Guaiacum officinale* L. nectandrin B, isonectandrin B and machilin I on the % of cells in S-phase. Camptothecin was used as a positive control. Treatment means with an * are statistically different from the control group at the 5% level according to Fisher's Projected LSD (SuperANOVA 1989).
Figure 8:
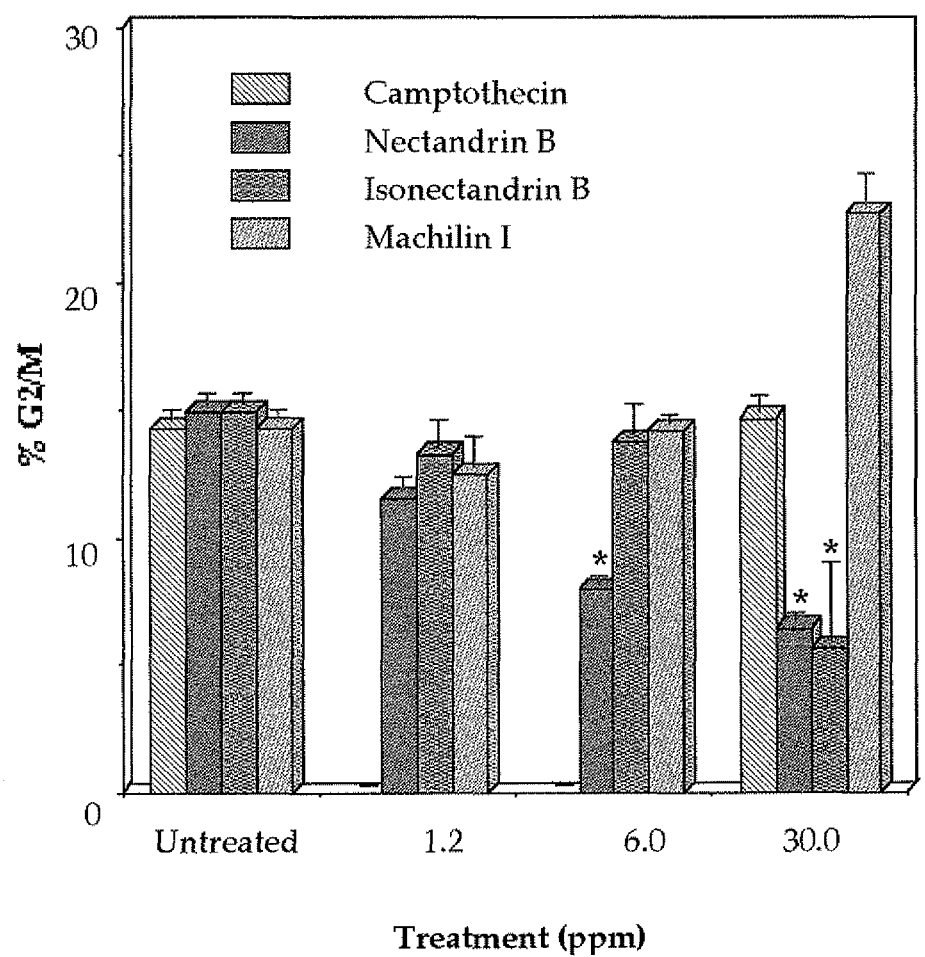
FIG. 8 shows the effect of lignans from the heartwood of *Guaiacum officinale* L. nectandrin B, isonectandrin B and machilin I on the % of cells in G2/M phase of the cell cycle. Analysis was determined by hypotonic lysis for DNA content at various doses for 24 hr. in human breast cancer cell line MD-MBA 231. Camptothecin was used as a positive control. Treatment means with an * are statistically different from the control group at the 5% level according to Fisher's Projected LSD (SuperANOVA 1989).

The relative percent events in S-phase determine those cells in the pool that are going through DNA synthesis. Isonectandrin B significantly inhibited cell populations in S-phase at all doses. When MD-MBA-231 cells are randomly distributed throughout the cell cycle, they have about 10-12% of cells in S phase. This was based on normal cell populations. The means for isonectandrin B were 8.2, 4.7 and 0 across increasing drug concentrations 1.2, 6.0, and 30.0 ppm, respectively. Nectandrin B inhibited cells from entering this stage as well in a concentration-dependent manner. Camptothecin was significant at 6.0 and 30.0 ppm and machilin I treatment showed significance at the highest concentration. Isonectandrin B showed the strongest decline of events in S-phase (FIG. 7). Of note, it appears that nectandrin B and isonectandrin B show similar S-phase arrest to camptothecin.

The data indicate that these compounds significantly reduce cell populations in S-phase with concomitant significant increases in sub G0. Without wishing to be bound by any theory, or to thereby limit the scope of the invention, it is noted that this could imply that loss of cellular integrity in a subpopulation of cells undergoing DNA synthesis after treatment with the diaryltetrahydrofuran-type lignans might be occurring. The % of events in S-phase was used as an index of G1/S arrest.

The effect on cell population in G2/M (mitosis) by nectandrin B showed significant reduction of cells at 6 and 30 ppm. Isonectandrin B showed the lowest accumulation at 30 ppm. Machilin I had the opposite effect. It showed an approximately 3-fold increase in % events at G2/M over isonectandrin B and nectandrin B and an increase of 8% over untreated cells at the highest treatment (FIG. 6.8). The effects of camptothecin remained at levels with untreated cells at all doses. Overall, the low level of events in G2/M phase for nectandrin B, isonectandrin B, and camptothecin further suggests and supports S-phase arrest. Whereas, the extent of elevated cell accumulation in G2/M with concomitant decreases in S-phase for machilin I suggests G2/M cell cycle arrest. Without being bound or limited by any theory, it appears that machilin I is having a different effect on cellular machinery. These data may suggest mitotic crisis. Whereas, isonectandrin B and nectandrin B appears to be affecting DNA synthesis.

On another note, the percent of apoptotic cell death was minimally characterized for machilin I in both the Annexin V-FITC assay and by estimating singlet and subG0 event percentages in DNA content analysis.

Similar to mitosis, apoptosis is reported being variable in duration and the characteristic biochemical and morphological changes vary and are dependent on cell line, concentration of drug induction and method of induction.

Figure 9:
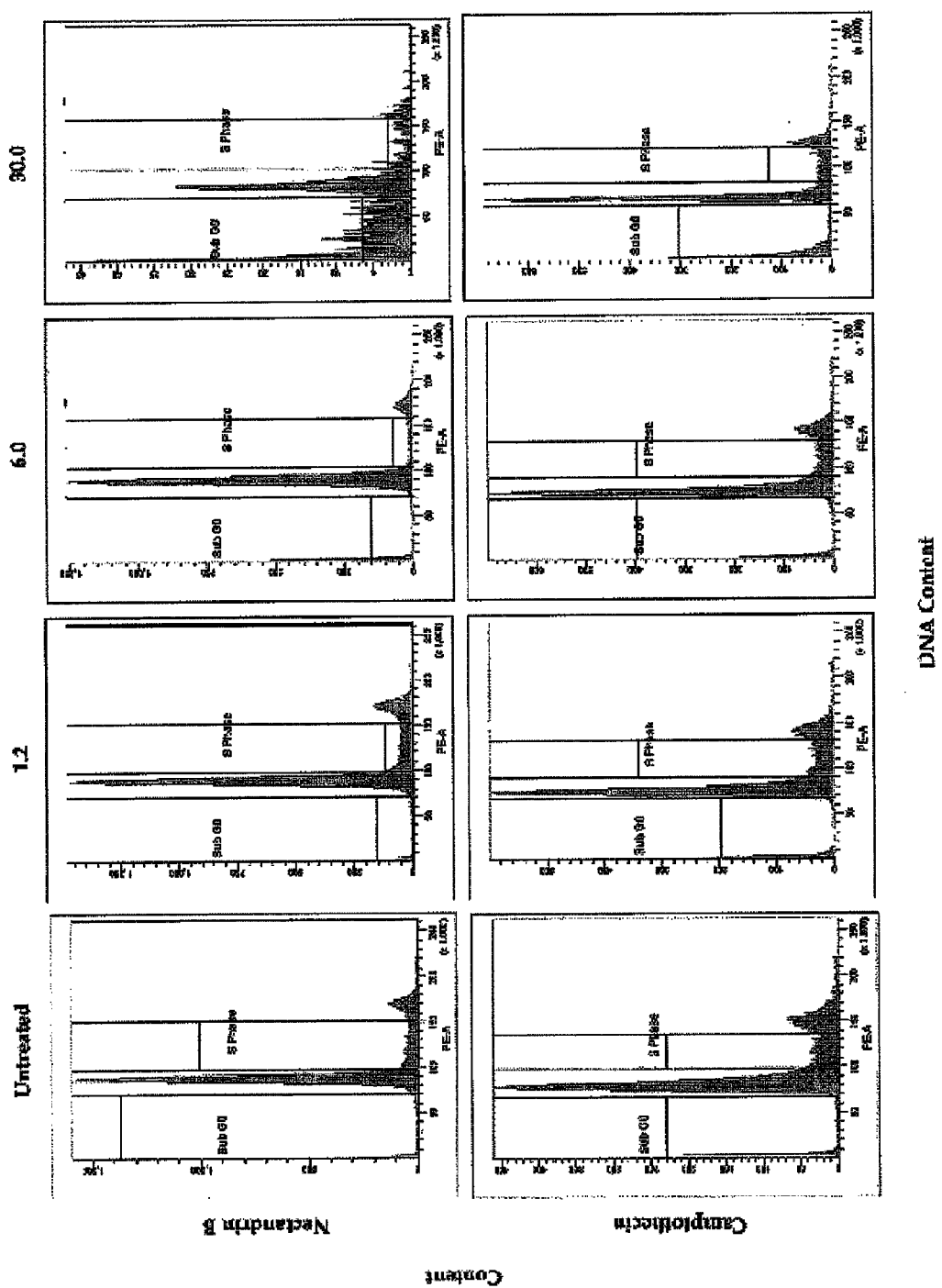
FIG. 9 shows DNA content frequency histograms of breast cancer cell line MD-MBA-231 of nectandrin B and camptothecin for 24 hr. Treatment occurred at 0, 1.2 ppm, 6.0 and 30.0 ppm.
Figure 10:
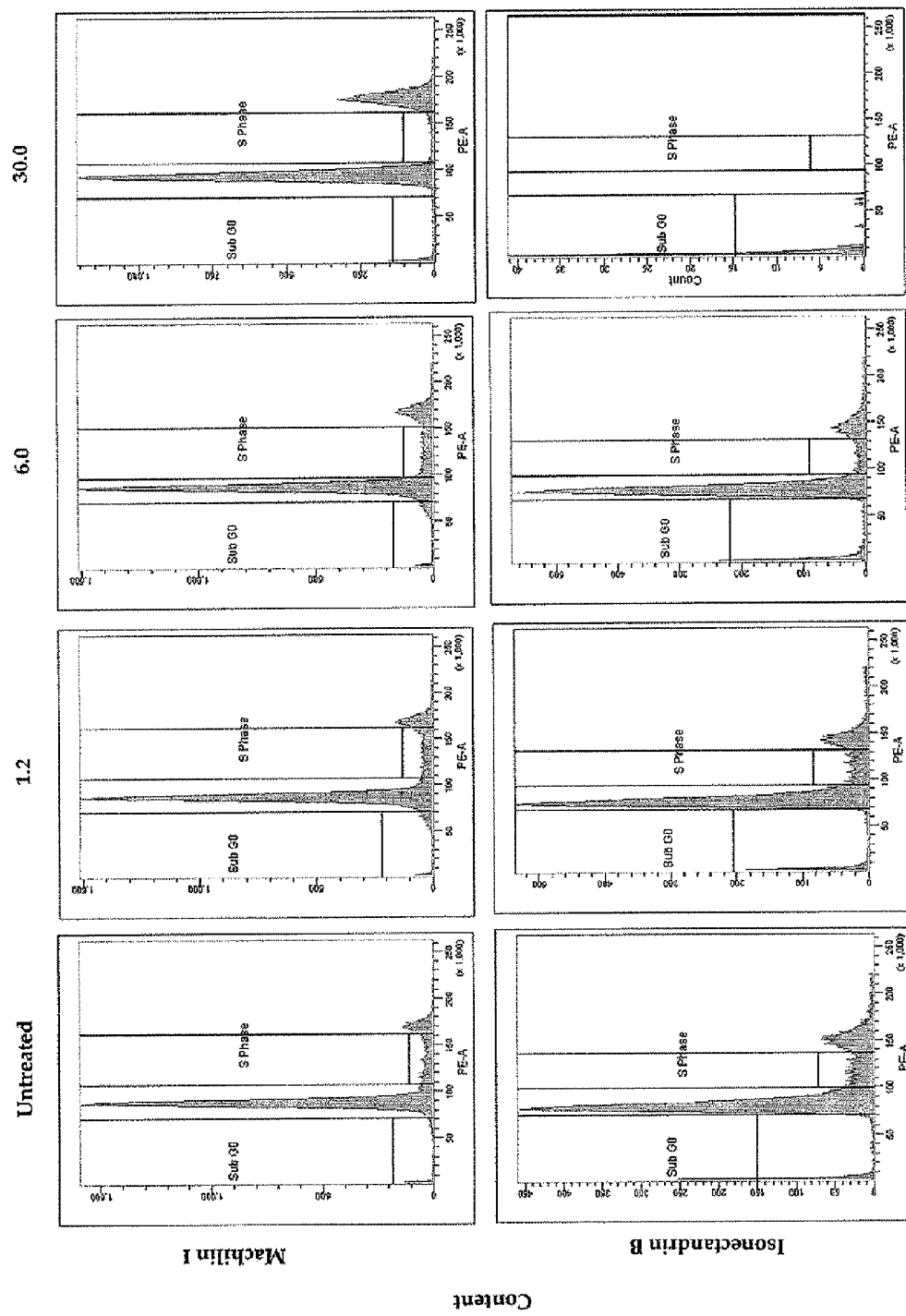
FIG. 10 shows DNA content frequency histograms of MD-MBA-231 human breast cancer cell line after treatment with isonectandrin B and machilin I. Treatment occurred at 24 hr. with 0, 1.2 ppm, 6.0 and 30.0 (ppm) of compound.

Without being bound by theory, it appears that the time window that characterizes apoptosis for machilin I was not reached or the duration of apoptosis has been prolonged in some regard, since there were not significant accumulation of cells indicating apoptotic cell death. The histograms of nectandrin B and camptothecin and isonectandrin B and machilin I can be viewed in FIGS. 9 and 10, respectively.

Figure 11:
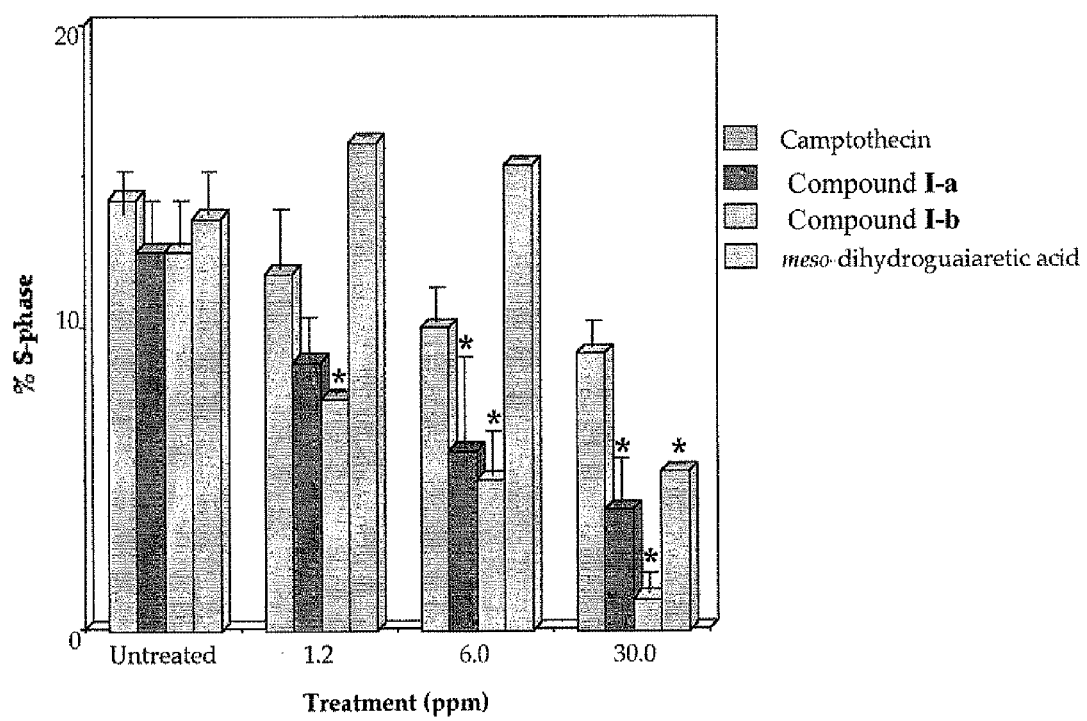
FIG. 11 shows the effect of compound I-a, compound I-b, and meso-dihydroguaiaretic acid on the % of cells in S-phase of the cell cycle. Cell line MD-MBA 231 was treated at varying doses for 24 hr. Analysis occurred by hypotonic lysis for DNA content and determined by FACS. Camptothecin was used as a positive control. Treatment means with an * are statistically different from the control group at the 5% level according to Fisher's Projected LSD (SuperANOVA, 1989).

The ability of the spirocyclic lignans (I-a and I-b) and meso-dihydroguaiaretic to hinder cell cycle progression was examined by DNA content analysis. The cells were evaluated under the same conditions as the previous studies. Compound I-a caused a progressive decrease in % S-phase events with increasing drug concentration in MD-MBA-231. Compound I-b showed a significant decrease in cell populations at the two highest doses and meso-dihydroguaiaretic acid did so at 30 ppm. Compound I-a showed less that 3% of cells in S-phase followed by Compound I-b at 4.5% and meso-dihydroguaiaretic acid at 6% at 30 ppm (FIG. 11).

Figure 12:
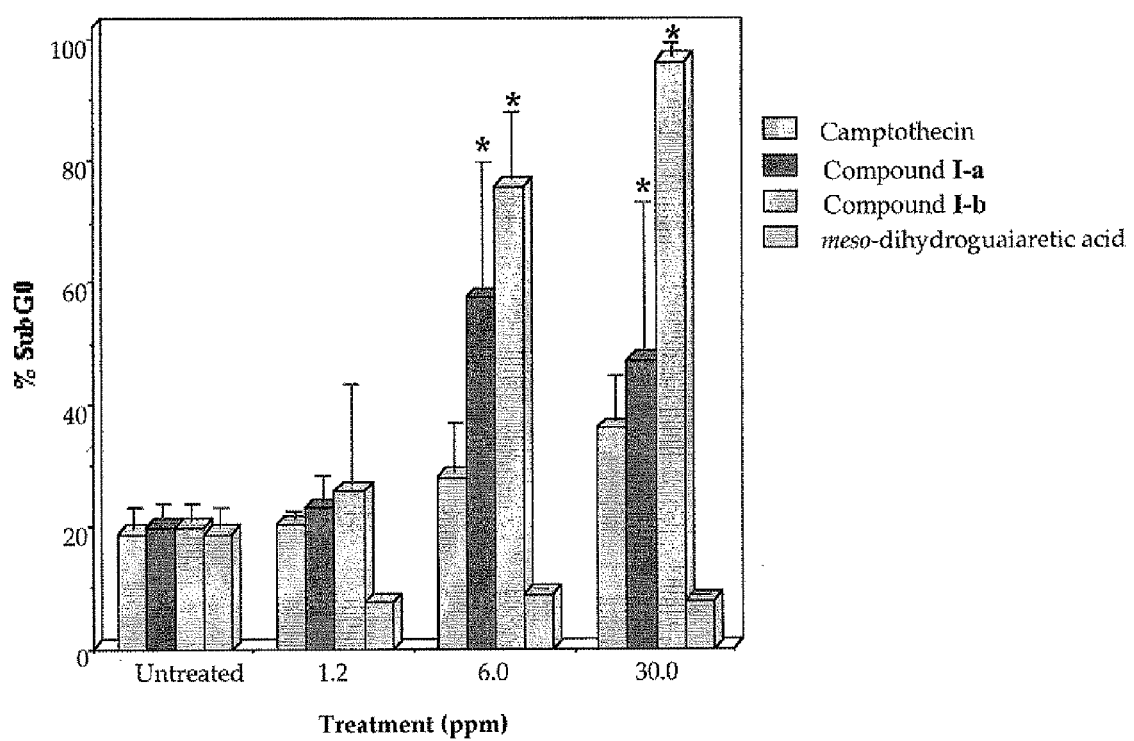
FIG. 12 shows Effect of compound I-a, compound I-b, and meso-dihydroguaiaretic acid from the heartwood of *Guaiacum officinale* L. on the % of cells in Sub G0 phase of the cell cycle. Cell line MD-MBA 231 was treated at varying doses for 24 hr. Analysis occurred by hypotonic lysis for DNA content and determined by FACS. Camptothecin was used as a positive control. Treatment means with an * are statistically different from the control group at the 5% level according to Fisher's Projected LSD (SuperANOVA, 1989).

Analysis of the decreased cell populations in S-phase appeared to accompany a progressive increase in % events in Sub G0 for compound I-a, compound I-b and camptothecin (FIG. 12). Apoptotic cell death was significance at 6 and 30 ppm for Compound I-b. Compound I-a showed strong apoptotic activity at 6.0 ppm, but then declined somewhat at 30 ppm, indicating the increased disruption in membrane integrity of dying cells. Overall, it appears that the compound I-a and I-b express similar cell cycle disruption to that shown by camptothecin and the diaryltetrahydrofuran lignans.

Meso-dihydroguaiaretic acid showed no significant increases in the percent of apoptotic events in sub G0, however, displayed a significant reduction of % cells in S-phase at 30 ppm. This is similar to the activity produced by machilin I, however, machilin I produced significant blockage in G2/M at 30 ppm without showing increased number of events in sub G0.

As defined herein, the term "active ingredient" refers to any of the compounds of Formula I through LII-d described herein or a pharmaceutically acceptable salt thereof.

It is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A method for the treatment of breast cancer in a mammal comprising administering to said mammal a composition comprising a pharmaceutically effective amount of a compound of the following formula:

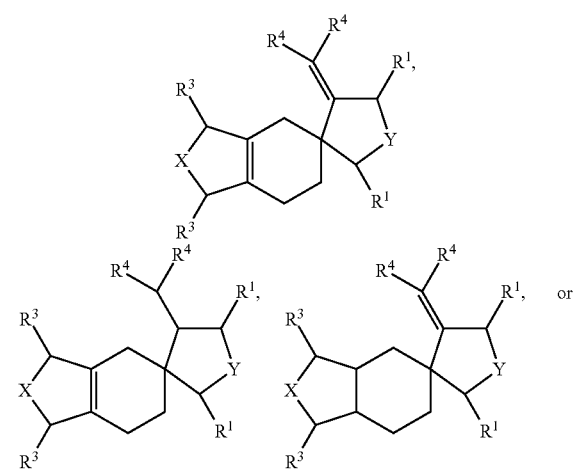

-continued

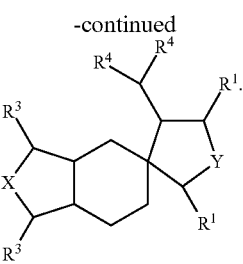

or a pharmaceutically acceptable salt thereof,
wherein:
X is —O—;
Y is —O—;
each $R^1$ and $R^3$ may be the same or different and, at each occurrence are independently an optionally substituted $C_{1-6}$ alkyl or

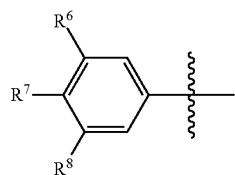

wherein: $R^6$, $R^7$, and $R^8$ are independently selected from the group consisting of: hydrogen and —$OR_y$,
$R^y$ is at each occurrence, independently selected from hydrogen and optionally substituted $C_{1-6}$ alkyl, where two or more $R^y$ groups can be taken together with their intervening atoms to form a ring; and
each $R^4$ may be the same or different and is hydrogen or optionally substituted $C_{1-6}$ alkyl, wherein said compound present in said composition is substantially pure.

2. The method according to claim 1, wherein the compound is:

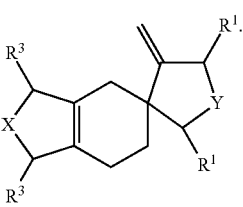

3. The method according to claim 1, wherein the compound is:

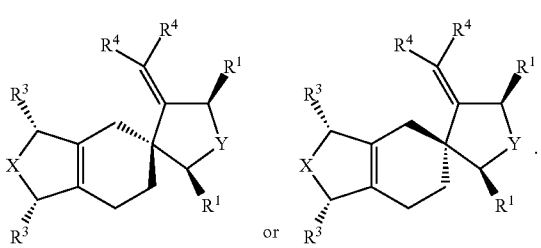

4. The method according to claim 1, wherein the compound is:

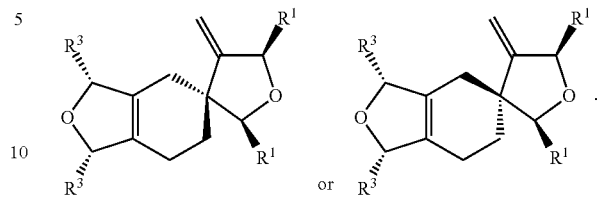

5. The method according to claim 4, wherein each $R^1$ and $R^3$ independently has a structure:

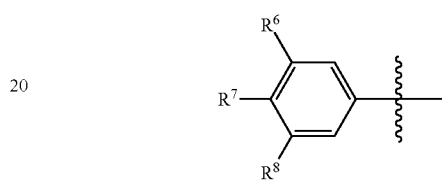

wherein:
$R^6$, $R^7$, and $R^8$ are independently selected from the group consisting of: hydrogen, and —$OR^y$, where two or more Ry groups can be taken together with their intervening atoms to form a ring.

6. The method according to claim 5, wherein each $R^1$ and $R^3$ is independently selected from the group consisting of:

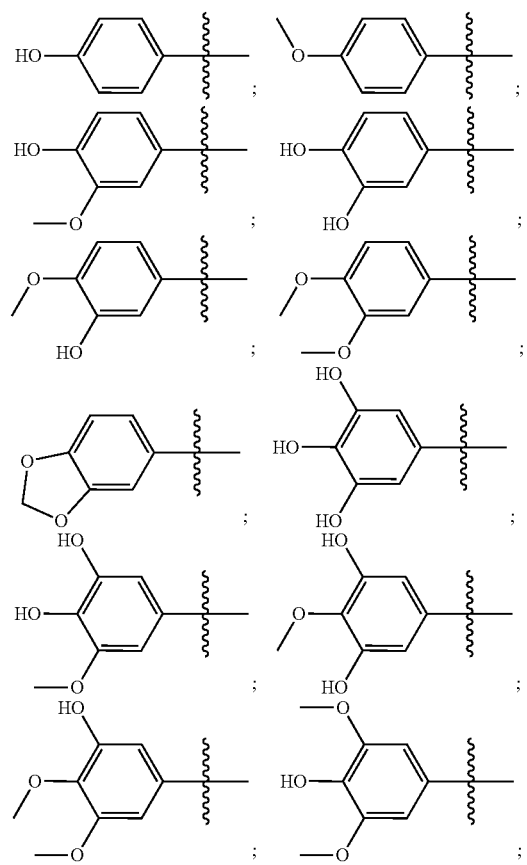

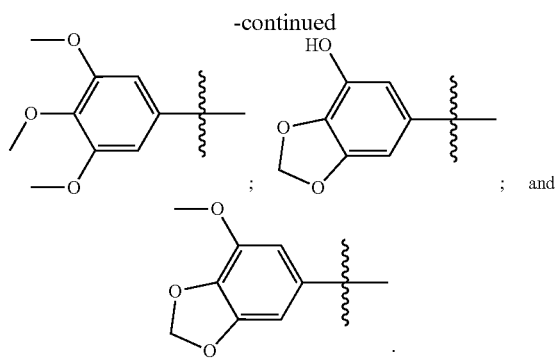

7. The method according to claim 4, wherein each $R^1$ and $R^3$ independently has the structure:

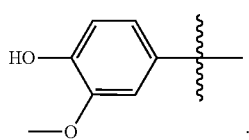 [SMILES: *c1ccc(O)c(OC)c1]

8. A substantially pure compound of the following formula,

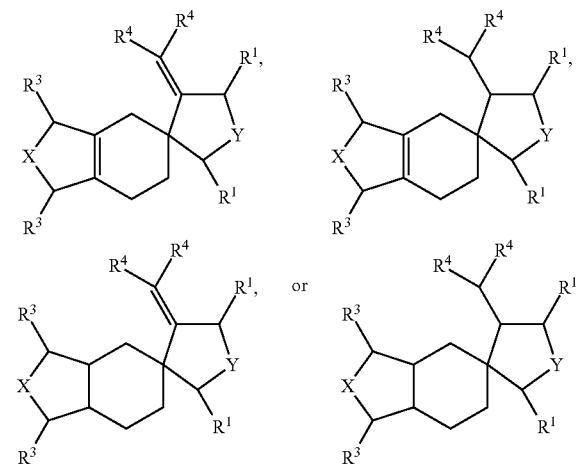

or a pharmaceutically acceptable salt thereof
wherein:
X is —O—;
Y is —O—;
each $R^1$ and $R^3$ may be the same or different and, at each occurrence are independently an optionally substituted $C_{1-6}$ alkyl or

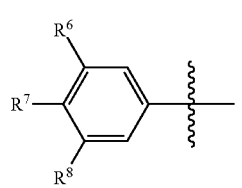

wherein: $R^6$, $R^7$, and $R^8$ are independently selected from the group consisting of: hydrogen and $-OR^y$, $R^y$ is at each occurrence, independently selected from hydrogen and optionally substituted $C_{1-6}$ alkyl, where two or more $R^y$ groups can be taken together with their intervening atoms to form a ring; and each $R^4$ may be the same or different and is hydrogen or optionally substituted $C_{1-6}$ alkyl.

9. The substantially pure compound according to claim 8, wherein the compound is:

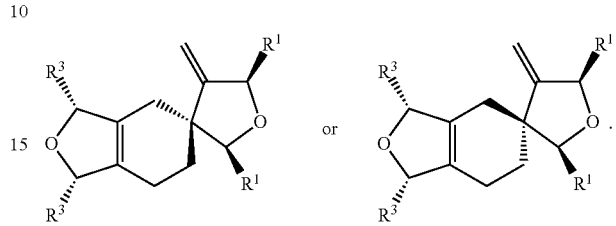

10. The substantially pure compound according to claim 9, wherein each $R^1$ and $R^3$ are independently:

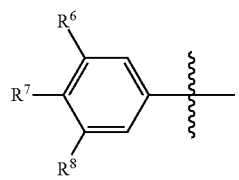

wherein:

$R^6$, $R^7$, and $R^8$ are independently selected from hydrogen, and $-OR^y$, where two or more $R^y$ groups can be taken together with their intervening atoms to form a ring.

11. The substantially pure compound according to claim 9, wherein each $R^1$ and $R^3$ is independently selected from:

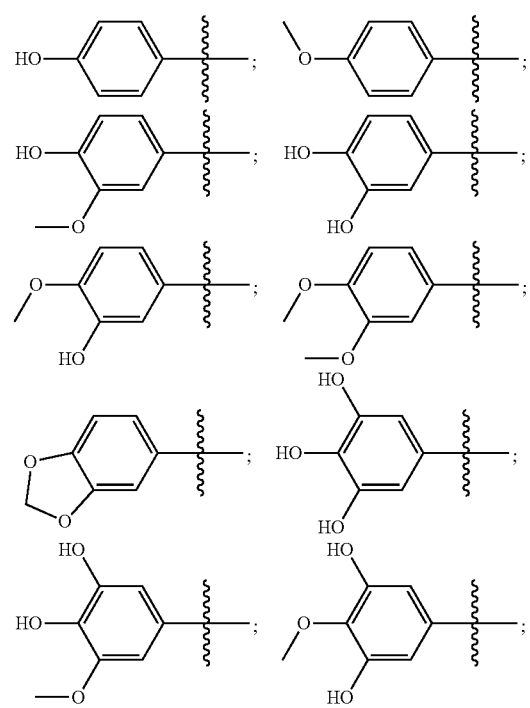

-continued

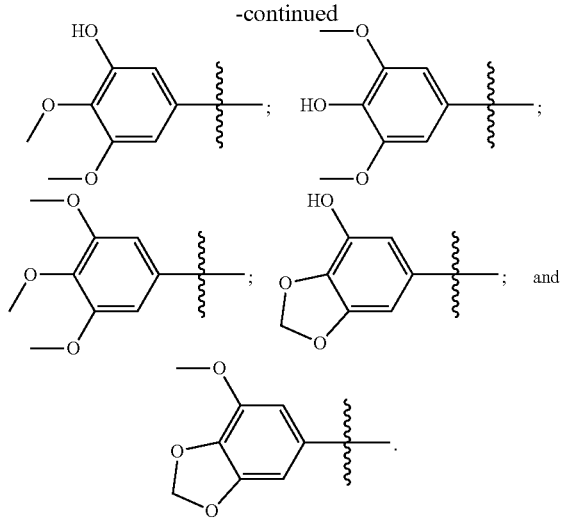

12. The substantially pure compound according to claim 9, wherein each $R^1$ and $R^3$ has the structure:

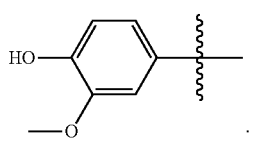 [SMILES: *c1ccc(O)c(OC)c1]

13. The method according to claim 1 wherein the compound is (I-a)

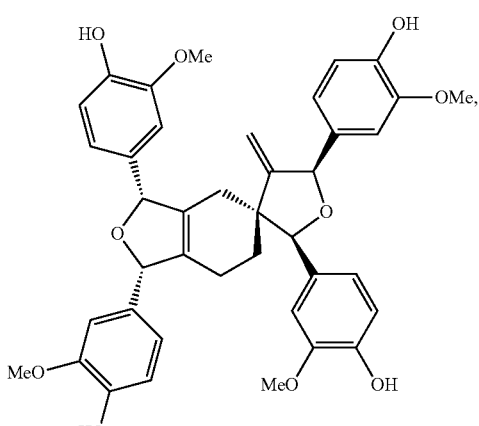

(I-b)

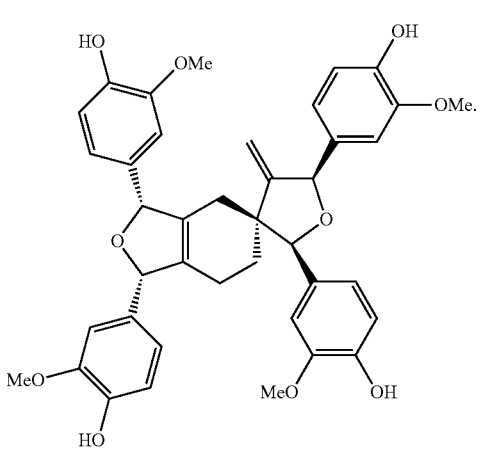

14. The substantially pure compound according to claim 8 wherein the compound is (I-a)

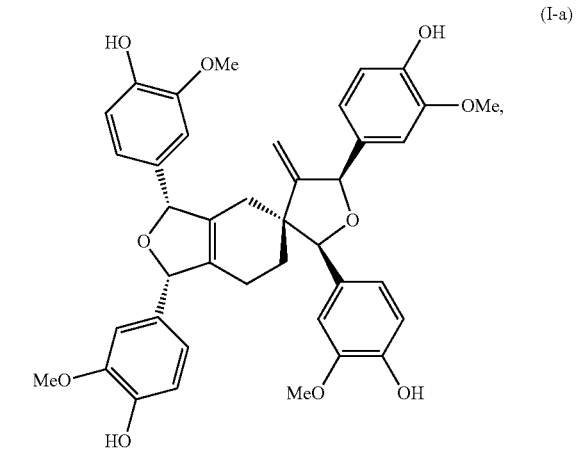

(I-b)

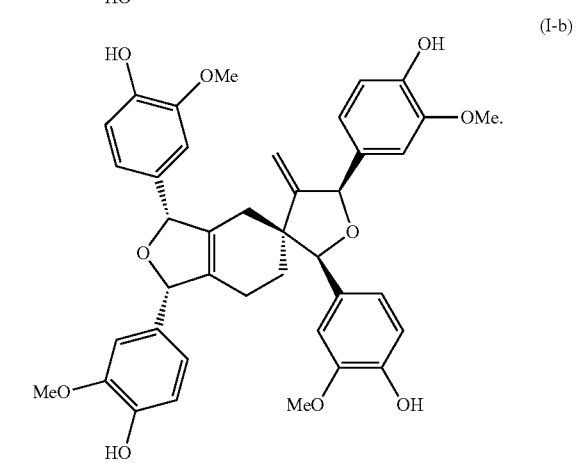

15. The substantially pure compound according to claim 8 wherein the compound is

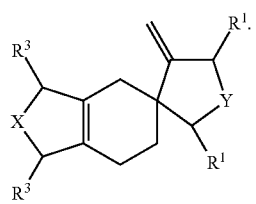

16. A composition comprising a compound of the following formula:

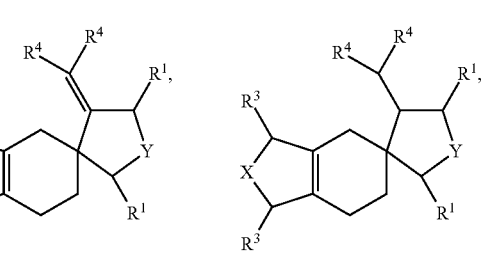

121

-continued

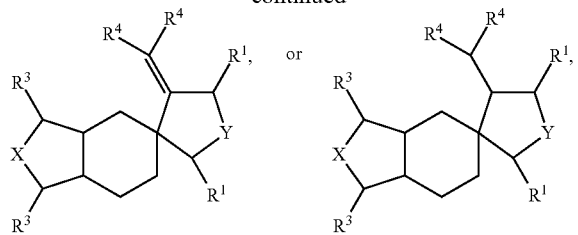

or a pharmaceutically acceptable salt thereof and one or more excipients or carriers, wherein:

X is —O—;

Y is —O—;

each $R^1$ and $R^3$ may be the same or different and, at each occurrence are independently an optionally substituted $C_{1-6}$ alkyl or

122

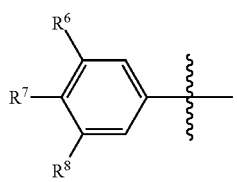

wherein: $R^6$, $R^7$, and $R^8$ are independently selected from the group consisting of: hydrogen and —$OR^y$, $R^y$ is at each occurrence, independently selected from hydrogen and optionally substituted $C_{1-6}$ alkyl, where two or more $R^y$ groups can be taken together with their intervening atoms to form a ring; and each $R^4$ may be the same or different and is hydrogen or optionally substituted $C_{1-6}$ alkyl, wherein said compound present in said composition is substantially pure.

* * * * *